(12) United States Patent
Koreth et al.

(10) Patent No.: US 10,806,773 B2
(45) Date of Patent: Oct. 20, 2020

(54) MULTIPLE-VARIABLE IL-2 DOSE REGIMEN FOR TREATING IMMUNE DISORDERS

(71) Applicant: Dana-Farber Cancer Institute, Inc., Boston, MA (US)

(72) Inventors: John Koreth, Roxbury, MA (US); Robert J. Soiffer, Waban, MA (US); Jerome Ritz, Lincoln, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 94 days.

(21) Appl. No.: 15/516,775

(22) PCT Filed: Oct. 7, 2015

(86) PCT No.: PCT/US2015/054466
§ 371 (c)(1),
(2) Date: Apr. 4, 2017

(87) PCT Pub. No.: WO2016/057651
PCT Pub. Date: Apr. 14, 2016

(65) Prior Publication Data
US 2017/0348391 A1    Dec. 7, 2017

Related U.S. Application Data

(60) Provisional application No. 62/061,952, filed on Oct. 9, 2014.

(51) Int. Cl.
*A61K 38/20* (2006.01)
*A61K 35/17* (2015.01)
*A61P 37/06* (2006.01)
*G01N 33/68* (2006.01)

(52) U.S. Cl.
CPC .......... *A61K 38/2013* (2013.01); *A61K 35/17* (2013.01); *A61P 37/06* (2018.01); *G01N 33/6893* (2013.01); *G01N 2800/52* (2013.01)

(58) Field of Classification Search
None
See application file for complete search history.

(56) References Cited

U.S. PATENT DOCUMENTS

| 6,921,530 B1 | 7/2005 | Smith |
|---|---|---|
| 2013/0071860 A1 | 3/2013 | Hale et al. |

FOREIGN PATENT DOCUMENTS

| WO | WO-2007136518 A2 | 11/2007 |
| WO | WO-2011139738 A2 | 11/2011 |
| WO | WO-2012/123381 A1 | 9/2012 |

OTHER PUBLICATIONS

The FDA Guideline for Industry Dose-response Information to Support Drug Registration (ICH-E4, Nov. 1994) (Year: 1994).*
Blaise et al (Leuk Lymphoma. May 1997;25(5-6):469-78) (Year: 1997).*
Rouse et al (Immunobiology. Apr. 2013 ; 218(4): 674-682) (Year: 2013).*
Steinman et al (Nat Med. Jan. 6, 2012;18(1):59-65) (Year: 2012).*
Blumberg et al (Nat Med. Jan. 6, 2012;18(1):35-41) (Year: 2012).*
Extended European Search Report for EP Application No. 15849237.1 dated May 22, 2018.
Whangbo et al., Individual Patient Dose-Escalated Low-Dose Interleukin-2 for Steroid-Refractory Chronic Graft-Vs.-Host Disease in Children and Adults: Safety, Efficacy and Immune Correlates, Blood, 130(Supplement 1): 3248 (2017).
Clinical Trial NCT01937468, "Trial of regulatory T-cells plus low-dose interleukin-2 for steroid-refractory chronic graft-versus-host-disease" (Aug. 30, 2013). Retrieved from the Internet at http://clinicaltrials.gov/ct2/show/NCT01937468?term=Korth&rank=1 [retrieved on Jul. 17, 2014].
Dana-Farber/Harvard Cancer Center News, "DF/HCC researchers reinvent anti-tumor IL-2 therapy for GVHD." Retrieved from the Internet at http://www.dfhcc.harvard.edu/index.php?id=1318&print=1&no_cache=1&tx _ttnews[tt_news]=4615&PHPSESSID=5b6886a9522714c5d0c741031d8147bc [retrieved on Aug. 5, 2014].
Di Ianni et al., "Tregs prevent GVHD and promote immune reconstitution in HLA-haploidentical transplantation," Blood, 117:3921-3928 (2011).
Fresenius Kabi News Release, "Fresenius Kabi scientific investigator award presented to Dana-Farber Cancer Institute" (Apr. 2, 2014). Retrieved from the Internet at http://www.fresenius-kabi.us/news-and-media/news-releases/202-fresenius-kabi-scientific-investigator-award-presented-to-dana-farber-cancer-institute.html [retrieved on Aug. 5, 2014].
Hartemann et al., "Low-dose interleukin 2 in patients with type 1 diabetes: a phase 1/2 randomised, double-blind, placebo-controlled trial," Lancet Diabetes Endocrinol, 1:295-305 (2013).
International Search Report and Written Opinion for International Application No. PCT/US15/54466 dated Feb. 23, 2016.
Koreth et al., "Interleukin-2 and regulatory T cells in graft-versus-host disease," New Engl J Med, 365:2055-2066 (2011).
Koreth et al., "Tregs, HSCT, and acute GVHD: up close and personal," Blood, 122:1690-1691 (2013).
Koreth, "Inducing peripheral tolerance via low-dose interleukin-2," Leukemia & Lymphoma Society Therapy Acceleration Program (LLS-TAP) Presentation (Jul. 18, 2014).
Long et al., "Rapamycin/IL-2 combination therapy in patients with type 1 diabetes augments Tregs yet transiently impairs β-cell function," Diabetes, 61:2340-2348 (2012).

(Continued)

*Primary Examiner* — Brian Gangle
*Assistant Examiner* — Andrea K McCollum
(74) *Attorney, Agent, or Firm* — Foley Hoag LLP

(57) ABSTRACT

The present invention is based, in part, on the identification of methods of using multiple-variable interleukin-2 (IL-2) doses for identifying, assessing, preventing, and treating immune disorders.

18 Claims, 8 Drawing Sheets
Specification includes a Sequence Listing.

(56) References Cited

OTHER PUBLICATIONS

Matsuoka et al., "Effects of daily low dose IL-2 therapy on homeostatic regulation of CD4+Foxp3+ regulatory T cells in patients with chronic graft-versus-host disease," Oral Abstract #895 presented at the 53th Annual Amer Soc Hematol (ASH) Meeting (Dec. 7, 2010).

Matsuoka et al., "Low-dose interleukin-2 therapy restores regulatory T cell homeostasis in patients with chronic graft-versus-host disease.," Sci Transl Med, 5:179ra43 (2013).

Nishimori et al., "Chronic graft-versus-host disease: disease biology and novel therapeutic strategies," Acta Med Okayama, 67:1-8 (2013).

Ritz, "Low dose IL-2 in chronic GVHD," Br Soc Blood Marrow Transplant, Spring Meeting Presentation (May 23, 2013).

Saadoun et al., "Regulatory T-cell responses to low-dose interleukin-2 in HCV-induced vasculitis," N Engl J Med, 365:2067-2077 (2011).

Zorn et al., "Combined CD4+ donor lymphocyte infusion and low-dose recombinant IL-2 expand FOXP3+ regulatory T cells following allogeneic hematopoietic stem cell transplantation," Biol Blood Marrow Transpl, 15:382-388 (2009).

Zorn et al., "Reduced frequency of FOXP3+ CD4+ CD25+ regulatory T cells in patients with chronic graft-versus-host disease," Blood 106:2903-2911 (2005).

Couriel et al., "Extracorporeal photochemotherapy for the treatment of steroid-resistant chronic GVHD," Blood, 107(8):3074-3080 (2006).

Martelli et al., "HLA-haploidentical transplantation with regulatory and conventional T-cell adoptive immunotherapy prevents acute leukemia relapse," Blood, 124(4):638-644 (2014).

Wang et al., "Research Progress on the Role of Interleukin 2 in the Pathogenesis of Autoimmune Diseases," Special Wild Economic Animal and Plant Research, Issue 4 (2011).

Holcar et al., "Age-Related Differences in Percentages of Regulatory and Effector T Lymphocytes and Their Subsets in Healthy Individuals and Characteristic STAT1/STAT5 Signalling Response in Helper T Lymphocytes," Journal of Immunology Research, 2015 (Article 113 352934): 1-13 (2015).

* cited by examiner

SEQUENCE LISTING

<160> NUMBER OF SEQ ID NOS: 12

<210> SEQ ID NO 1
<211> LENGTH: 462
<212> TYPE: DNA
<213> ORGANISM: Homo sapiens

<400> SEQUENCE: 1

```
atgtacagga tgcaactcct gtcttgcatt gcactaagtc ttgcacttgt cacaaacagt      60
gcacctactt caagttctac aaagaaaaca cagctacaac tggagcattt actgctggat     120
ttacagatga ttttgaatgg aattaataat tacaagaatc ccaaactcac caggatgctc     180
acatttaagt tttacatgcc caagaaggcc acagaactga aacatcttca gtgtctagaa     240
gaagaactca aacctctgga ggaagtgcta aatttagctc aaagcaaaaa ctttcactta     300
agacccaggg acttaatcag caatatcaac gtaatagttc tggaactaaa gggatctgaa     360
acaacattca tgtgtgaata tgctgatgag acagcaacca ttgtagaatt tctgaacaga     420
tggattacct tttgtcaaag catcatctca acactgactt ga                        462
```

<210> SEQ ID NO 2
<211> LENGTH: 153
<212> TYPE: PRT

<213> ORGANISM: Homo sapiens

<400> SEQUENCE: 2

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150

<210> SEQ ID NO 3
<211> LENGTH: 462
<212> TYPE: DNA
<213> ORGANISM: Pan troglodytes

<400> SEQUENCE: 3
atgtacagga tgcaactcct gtcttgcatt gcactaagtc ttgcacttgt cacaaacagt    60
gcacctactt caagttctac aaagaaaaca cagctacaac tggagcattt actgctggat   120
ttacagatga ttttgaatgg aattaataat tacaagaatc ccaaactcac caggatgctc   180
acatttaagt tttacatgcc caagaaggcc acagaactga acatcttca gtgtctagaa    240
gaagaactca aacctctgga ggaagtgcta aatttagctc aaagcaaaaa ctttcactta   300
agacccaggg acttaatcag caatatcaac gtaatagttc tggaactaaa gggatctgaa   360
acaacattca tgtgtgaata tgctgatgag acagcaacca ttgtagaatt tctgaacaga   420
tggattacct tttgtcaaag catcatctca acactgactt ga                      462

<210> SEQ ID NO 4
<211> LENGTH: 153
<212> TYPE: PRT
<213> ORGANISM: Pan troglodytes

<400> SEQUENCE: 4

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu

```
                65                  70                  75                  80
Glu Glu Leu Lys Pro Leu Glu Glu Val Leu Asn Leu Ala Gln Ser Lys
                    85                  90                  95

Asn Phe His Leu Arg Pro Arg Asp Leu Ile Ser Asn Ile Asn Val Ile
                100                 105                 110

Val Leu Glu Leu Lys Gly Ser Glu Thr Thr Phe Met Cys Glu Tyr Ala
                115                 120                 125

Asp Glu Thr Ala Thr Ile Val Glu Phe Leu Asn Arg Trp Ile Thr Phe
130                 135                 140

Cys Gln Ser Ile Ile Ser Thr Leu Thr
145                 150

<210> SEQ ID NO 5
<211> LENGTH: 465
<212> TYPE: DNA
<213> ORGANISM: Macaca mulatta

<400> SEQUENCE: 5
atgtacagga tgcaactcct gtcttgcatt gcactaagtc ttgcacttgt cacaaacagt    60
gcacctactt caagttctac aaagaaaaca cagctacaac tggagcattt actgctggat   120
ttacagatga ttttgaatgg aattaataat acaagaatcc caaactcac aggatgctc     180 acatttaagt tttacatgcc caagaaggcc acagaattga acatcttca gtgtctagaa    240 gaagaactca aacctctgga ggaagtgcta aatttagctc aaagcaaaaa ctttcactta   300
agagatacca aggacttaat cagcaatatc aacgtaatag ttctggaact aaagggatct   360
gaaacaacac tgatgtgtga atatgctgat gagacagcaa ccattgtaga atttctgaac   420
agatggatta ccttttgtca agcatcatc tcaacactga cctga                    465

<210> SEQ ID NO 6
<211> LENGTH: 154
<212> TYPE: PRT
<213> ORGANISM: Macaca mulatta

<400> SEQUENCE: 6

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
                20                  25                  30

Gln Leu Glu His Leu Leu Leu Asp Leu Gln Met Ile Leu Asn Gly Ile
            35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                    85                  90                  95

Asn Phe His Leu Arg Asp Thr Lys Asp Leu Ile Ser Asn Ile Asn Val
                100                 105                 110

Ile Val Leu Glu Leu Lys Gly Ser Glu Thr Thr Leu Met Cys Glu Tyr
                115                 120                 125

Ala Asp Glu Thr Ala Thr Ile Val Glu Phe Leu Asn Arg Trp Ile Thr
            130                 135                 140

Phe Cys Gln Ser Ile Ile Ser Thr Leu Thr
145                 150
```

<210> SEQ ID NO 7
<211> LENGTH: 468
<212> TYPE: DNA
<213> ORGANISM: Canis familiaris

<400> SEQUENCE: 7

```
atgtacaaaa tgcaactctt gtcttgcatc gcactgacgc ttgtacttgt cgcaaacagt    60
gcacctatta cttcaagctc tacaaaggaa acagagcaac agatggagca attactgctg   120
gatttacagt tgcttttgaa tggagttaat aattatgaga ccccccaact ctccaggatg   180
ctcacattta gttttacac gcccaagaag gccacagaat ttacacacct tcaatgtcta   240
gcagaagaac tcaaaaacct ggaggaagtg ctaggtttac ctcaaagcaa aaacgttcac   300
ttgacagaca ccaaggaatt aatcagcaat atgaatgtaa cacttctgaa actaaaggga   360
tctgaaacaa gttacaactg tgaatatgat gacgagacag caaccattac agaatttctg   420
aacaaatgga ttacctttg tcaaagcatc ttctcaacac tgacttga                 468
```

<210> SEQ ID NO 8
<211> LENGTH: 155
<212> TYPE: PRT
<213> ORGANISM: Canis familiaris

<400> SEQUENCE: 8

```
Met Tyr Lys Met Gln Leu Leu Ser Cys Ile Ala Leu Thr Leu Val Leu
  1               5                  10                  15

Val Ala Asn Ser Ala Pro Ile Thr Ser Ser Thr Lys Glu Thr Glu
             20                  25                  30

Gln Gln Met Glu Gln Leu Leu Leu Asp Leu Gln Leu Leu Leu Asn Gly
         35                  40                  45

Val Asn Asn Tyr Glu Asn Pro Gln Leu Ser Arg Met Leu Thr Phe Lys
     50                  55                  60

Phe Tyr Thr Pro Lys Lys Ala Thr Glu Phe Thr His Leu Gln Cys Leu
 65                  70                  75                  80

Ala Glu Glu Leu Lys Asn Leu Glu Glu Val Leu Gly Leu Pro Gln Ser
                 85                  90                  95

Lys Asn Val His Leu Thr Asp Thr Lys Glu Leu Ile Ser Asn Met Asn
            100                 105                 110

Val Thr Leu Leu Lys Leu Lys Gly Ser Glu Thr Ser Tyr Asn Cys Glu
        115                 120                 125

Tyr Asp Asp Glu Thr Ala Thr Ile Thr Glu Phe Leu Asn Lys Trp Ile
    130                 135                 140

Thr Phe Cys Gln Ser Ile Phe Ser Thr Leu Thr
145                 150                 155
```

<210> SEQ ID NO 9
<211> LENGTH: 510
<212> TYPE: DNA
<213> ORGANISM: Mus musculus

<400> SEQUENCE: 9

```
atgtacagca tgcagctcgc atcctgtgtc acattgacac ttgtgctcct tgtcaacagc    60
gcacccactt caagctccac ttcaagctct acagcggaag cacagcagca gcagcagcag   120
cagcagcagc agcagcagca cctggagcag ctgttgatgg acctacagga gctcctgagc   180
aggatggaga attacaggaa cctgaaactc ccaggatgc tcaccttcaa atttacttg   240
cccaagcagg ccacagaatt gaaagatctt cagtgcctag aagatgaact tggacctctg   300
```

```
cggcatgttc tggatttgac tcaaagcaaa agctttcaat tggaagatgc tgagaatttc      360
atcagcaata tcagagtaac tgttgtaaaa ctaaagggct ctgacaacac atttgagtgc      420
caattcgatg atgagtcagc aactgtggtg gactttctga ggagatggat agccttctgt      480
caaagcatca tctcaacaag ccctcaataa                                       510
```

<210> SEQ ID NO 10
<211> LENGTH: 169
<212> TYPE: PRT
<213> ORGANISM: Mus musculus

<400> SEQUENCE: 10

```
Met Tyr Ser Met Gln Leu Ala Ser Cys Val Thr Leu Thr Leu Val Leu
1               5                  10                  15

Leu Val Asn Ser Ala Pro Thr Ser Ser Thr Ser Ser Ser Thr Ala
            20                  25                  30

Glu Ala Gln Gln Gln Gln Gln Gln Gln Gln Gln Gln Gln His Leu
        35                  40                  45

Glu Gln Leu Leu Met Asp Leu Gln Glu Leu Leu Ser Arg Met Glu Asn
    50                  55                  60

Tyr Arg Asn Leu Lys Leu Pro Arg Met Leu Thr Phe Lys Phe Tyr Leu
65                  70                  75                  80

Pro Lys Gln Ala Thr Glu Leu Lys Asp Leu Gln Cys Leu Glu Asp Glu
                85                  90                  95

Leu Gly Pro Leu Arg His Val Leu Asp Leu Thr Gln Ser Lys Ser Phe
            100                 105                 110

Gln Leu Glu Asp Ala Glu Asn Phe Ile Ser Asn Ile Arg Val Thr Val
        115                 120                 125

Val Lys Leu Lys Gly Ser Asp Asn Thr Phe Glu Cys Gln Phe Asp Asp
    130                 135                 140

Glu Ser Ala Thr Val Val Asp Phe Leu Arg Arg Trp Ile Ala Phe Cys
145                 150                 155                 160

Gln Ser Ile Ile Ser Thr Ser Pro Gln
                165
```

<210> SEQ ID NO 11
<211> LENGTH: 468
<212> TYPE: DNA
<213> ORGANISM: Rattus norvegicus

<400> SEQUENCE: 11

```
atgtacagca tgcagctcgc atcctgtgtt gcactgacgc ttgtcctcct tgtcaacagc       60
gcacccactt caagccctgc aaaggaaaca cagcagcacc tggagcagct gttgctggac      120
ttacaggtgc tcctgagagg gatcgataat tacaagaatc tgaaactccc catgatgctc      180
acgtttaaat tttacttgcc caagcaggcc acagaattga acatcttca gtgcctggaa       240 aatgaactcg gagctctgca gcgtgtgttg gatttgactc aaagcaaaag ctttcacttg      300
gaagacgctg gaaatttcat cagcaatatc agagtaactg ttgtaaaact aaagggctct      360
gaaaacaaat ttgagtgcca attcgatgat gagccagcaa ctgtggtgga atttctgagg      420
agatggatag ccatctgtca agcatcatc tcaacaatga ctcagtaa                   468
```

<210> SEQ ID NO 12
<211> LENGTH: 155
<212> TYPE: PRT
<213> ORGANISM: Rattus norvegicus

```
<400> SEQUENCE: 12

Met Tyr Ser Met Gln Leu Ala Ser Cys Val Ala Leu Thr Leu Val Leu
1               5                   10                  15

Leu Val Asn Ser Ala Pro Thr Ser Ser Pro Ala Lys Glu Thr Gln Gln
            20                  25                  30

His Leu Glu Gln Leu Leu Leu Asp Leu Gln Val Leu Leu Arg Gly Ile
        35                  40                  45

Asp Asn Tyr Lys Asn Leu Lys Leu Pro Met Met Leu Thr Phe Lys Phe
        50                  55                  60

Tyr Leu Pro Lys Gln Ala Thr Glu Leu Lys His Leu Gln Cys Leu Glu
65                  70                  75                  80

Asn Glu Leu Gly Ala Leu Gln Arg Val Leu Asp Leu Thr Gln Ser Lys
                85                  90                  95

Ser Phe His Leu Glu Asp Ala Gly Asn Phe Ile Ser Asn Ile Arg Val
            100                 105                 110

Thr Val Val Lys Leu Lys Gly Ser Glu Asn Lys Phe Glu Cys Gln Phe
            115                 120                 125

Asp Asp Glu Pro Ala Thr Val Val Glu Phe Leu Arg Arg Trp Ile Ala
            130                 135                 140

Ile Cys Gln Ser Ile Ile Ser Thr Met Thr Gln
145                 150                 155
```

MULTIPLE-VARIABLE IL-2 DOSE REGIMEN FOR TREATING IMMUNE DISORDERS

CROSS-REFERENCE TO RELATED APPLICATIONS

This application is a national-stage filing under 35 U.S.C. § 371 of PCT International Application No. PCT/US15/54466, filed on Oct. 7, 2015, which claims the benefit of U.S. Provisional Application No. 62/061,952, filed on Oct. 9, 2014; the entire contents of each of said applications are incorporated herein in their entirety by this reference.

STATEMENT OF RIGHTS

This invention was made with government support under grant numbers RO1 CA183559 and RO1 CA183560 awarded by The National Institutes of Health. The government has certain rights in the invention.

BACKGROUND OF THE INVENTION

Regulatory T-cells (Tregs) are required for immune tolerance and function as dominant suppressors of adaptive and innate immune effector cells. Tregs-based therapeutics offer a homeostatic mechanism to control maladaptive immune activation noted in immune disorders such as solid organ transplantation rejections and graft-versus-host disease (GVHD), and also in other disorders of impaired peripheral tolerance where Tregs dysfunction is increasingly implicated (e.g., systemic autoimmune diseases including vasculitis, systemic lupus erythematosus (SLE), type 1 diabetes (T1D), multiple sclerosis (MS), psoriasis, rheumatoid arthritis (RA), inflammatory bowel disease (IBD), and allergic asthma) (Saadoun et al. (2011) *N. Engl. J. Med.* 365:2067-2077; Hartemann et al. (2013) *Lancet Diabetes Endocrinol.* 1:295-305; Humrich et al. (2014) *Ann. Rheum. Dis.* 73:A46; Lambrecht et al. (2013) *Eur. J. Immunol.* 43:3125-3137). However, treatment approaches based on infusion of ex vivo expanded Tregs have been difficult to implement and do not address the need to maintain the function of adoptively transferred cells for long term inflammatory control (Brunstein et al. (2011) *Blood* 117:1061-1070). Moreover, while low-dose IL-2 can enhance Tregs, half of cGVHD participants do not obtain clinical benefit (Koreth et al. (2011) *N. Engl. J. Med.* 365:2055-2066). Thus, a great need in the art exists for compositions and methods for improving the ability of Tregs to ameliorate unwanted immune reactions. In particular, advances in cGVHD therapy are urgently required, especially for children, who have many years to live with the debilitating consequences of cGVHD, such as sclerotic skin, joint contractures or pulmonary fibrosis.

SUMMARY OF THE INVENTION

The present invention is based, at least in part, on the discovery that multiple-variable dose IL-2 can significantly augment in vivo Treg numbers and activity in order to treat immune disorders, such as GVHD (e.g., active, chronic GVHD). Such treatment effects are further increased in combination with one or more additional anti-immune disorder therapies, such as administration of ECP and/or Tregs.

In one aspect, a multiple-variable IL-2 dose method of treating a subject afflicted with an immune disorder comprising: a) administering to the subject an induction regimen comprising continuously administering to the subject interleukin-2 (IL-2) at a dose that increases the subject's plasma IL-2 level and increases the subject's ratio of regulatory T lymphocytes (Tregs) to conventional T lymphocytes (Tcons) (Tregs:Tcons); and b) subsequently administering to the subject at least one maintenance regimen comprising continuously administering to the subject an IL-2 maintenance dose that is higher than the induction regimen dose and that i) further increases the subject's plasma IL-2 level and ii) further increases the ratio of Tregs to Tcons, thereby treating the subject, is provided.

Certain embodiments are applicable to any method described herein. For example, in one embodiment, the IL-2 maintenance regimen increases the subject's plasma IL-2 level beyond the peak plasma IL-2 level induced by the induction regimen. In another embodiment, the plasma IL-2 levels are determined by analyzing one or more of time after IL-2 administration, IL-2 protein levels, IL-2 protein activity, IL-2 nucleic acid levels, Tregs proliferation, Tregs activity, Tregs phosphorylated STAT5 levels, Tregs FOXP3 levels, and Tregs apoptosis. In still another embodiment, the induction regimen dose is about $0.3 \times 10^6$ IU/m$^2$/day to about $3.0 \times 10^6$ IU/m$^2$/day. In yet another embodiment, the induction regimen dose is less than about $6.0 \times 10^6$ IU/m$^2$/day. In another embodiment, the continuous administration of the induction regimen comprises administration once per day and continues indefinitely as long as the patient continues to experience clinical benefit. In still another embodiment, the continuous administration of the induction regimen comprises administration once per day during at least 1-14 consecutive days. In yet another embodiment, the Tregs:Tcons ratio in the maintenance regimen is increased by at least 20% over the maximal Tregs:Tcons during the induction regimen. In another embodiment, the maiintenance regimen dose is at least about 20% higher than the induction regimen dose. In still another embodiment, the maintenance regimen dose is about $0.3 \times 10^6$ IU/m$^2$/day to about $3.0 \times 10^6$ IU/m$^2$/day. In yet another embodiment, the maintenance regimen dose is less than about $6.0 \times 10^6$ IU/m$^2$/day. In another embodiment, the continuous administration of the maintenance regimen comprises administration indefinitely as long as the patient continues to experience clinical benefit. In still another embodiment, the continuous administration of the maintenance regimen comprises administration once per day during at least 1-42 consecutive days.

In still another embodiment, the IL-2 is administered in a pharmaceutically acceptable formulation. In another embodiment, the IL-2 is administered by an administration route selected from the group consisting of subcutaneous, intravenous, intraperitoneal, and intramuscular. In still another embodiment, the IL-2 is administered subcutaneously. In yet another embodiment, the immune disorder is selected from the group consisting of graft-versus-host disease (GVHD), solid organ transplantation rejection, vasculitis, systemic lupus erythematosus (SLE), type 1 diabetes (T1D), multiple sclerosis (MS), psoriasis, rheumatoid arthritis (RA), inflammatory bowel disease (IBD), and allergic asthma. In another embodiment, the immune disorder is cGVHD. In still another embodiment, the subject has had an inadequate response to systemic steroids. In yet another embodiment, the subject has persistent or recurrent chronic GVHD despite at least 2 prior systemic therapies including steroids. In another embodiment, the subject has had extracorporeal photopheresis (ECP) prior to IL-2 administration. In still another embodiment, the induction regimen and/or the maintenance regimen further comprises administration of one or more additional therapies to treat the immune disorder. In yet another embodiment, the one or more additional therapies is selected from the group consisting of ECP and Tregs. In another embodiment, the Tregs are administered as a composition comprising T cells other than Tregs. In still another embodiment, the composition has a Tregs:Tcons ratio of at least 1:2. In yet another embodiment, the composition is obtained from CD8+ and CD19+ co-depletion and CD25+ positive selection of biological material comprising T cells. In another embodiment, the Tregs are administered at between about $0.1 \times 10^6$ cells/kg body weight to $1.0 \times 10^6$ cells/kg body weight. In still another embodiment, the subject's own Tregs are administered to the subject. In yet another embodiment, Tregs from the same hematopoietic stem cell donor from which hematopoietic stem cell transplantation was obtained is used. In another embodiment, the Tregs composition has >70% total cell viability, a negative gram stain, ≥90% CD4+CD25+ cells, and/or ≥50% FoxP3+ cells. In still another embodiment, the Tregs are administered as an infusion. In yet another embodiment, the Tregs are administered before, concurrently with, or after IL-2 administration. In another embodiment, the Tregs are administered before IL-2 administration. In still another embodiment, the subject is a mammal, such as a human or an animal model of an immune disorder.

In another aspect, a method of stratifying subjects afflicted with an immune disorder according to benefit from a fixed daily IL-2 dose treatment method comprising obtaining a biological sample comprising T lymphocytes from a subject and determining the ratio of regulatory T lymphocytes (Tregs) to conventional T lymphocytes (Tcons) (Tregs:Tcons) in the subject sample, wherein the Tregs:Tcons ratio of greater than or equal to about 0.07 indicates that the subject would benefit from the fixed daily IL-2 dose treatment method and wherein the Tregs:Tcons ratio of less than about 0.07 indicates that the subject would not benefit from the fixed daily IL-2 dose treatment method, is provided. In one embodiment, the method further comprises recommending, prescribing, or administering a fixed daily IL-2 dose method or a method of treatment described herein if the immune disorder is determined to benefit from the fixed daily IL-2 dose treatment method. In another embodiment, the method further comprises recommending, prescribing, or administering anti-immune disorder therapy other than a fixed daily IL-2 dose treatment method if the immune disorder is determined to not benefit from a fixed daily IL-2 dose treatment method.

In still another aspect, a method of stratifying subjects afflicted with an immune disorder according to benefit from a fixed daily IL-2 dose treatment method comprising obtaining a biological sample comprising T lymphocytes from a subject after the induction regiment and determining the ratio of regulatory T lymphocytes (Tregs) to conventional T lymphocytes (Tcons) (Tregs:Tcons) in the subject sample, wherein the Tregs:Tcons ratio of greater than or equal to about 0.20 indicates that the subject would benefit from the fixed daily IL-2 dose treatment method and wherein the Tregs:Tcons ratio of less than about 0.20 indicates that the subject would not benefit from the fixed daily IL-2 dose treatment method, is provided. In one embodiment, the method further comprises recommending, prescribing, or administering a fixed daily IL-2 dose method or a method of treatment described herein if the immune disorder is determined to benefit from the fixed daily IL-2 dose treatment method. In another embodiment, the method further comprises recommending, prescribing, or administering anti-immune disorder therapy other than a fixed daily IL-2 dose treatment method if the immune disorder is determined to not benefit from a fixed daily IL-2 dose treatment method.

BRIEF DESCRIPTION OF THE DRAWINGS

FIG. 1 depicts a representative patient on Dose Level B.

DETAILED DESCRIPTION OF THE INVENTION

Figure 1:
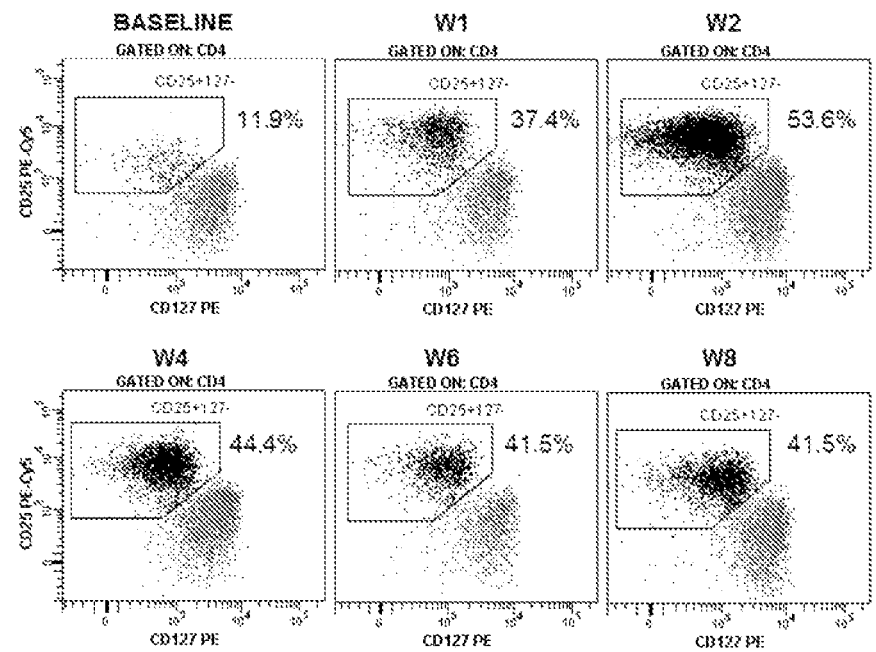
FIG. 1 in vivo expansion of CD4+ Treg during treatment with daily low-dose IL-2. The results of cell sorting analyses gated on CD3+CD4+ T are shown. Tregs are defined as CD25+CD127− and Tcons are CD25−CD127+. The % Tregs within the CD4 gate is indicated in each plot.

It has been determined that plasma IL-2 levels rise rapidly (e.g., by week 1) during fixed-dose IL-2 therapy, then, despite daily IL-2 administration, decline while Tregs count rise (Matsuoka et al. (2013) *Sci. Transl. Med.* 5:179ra43) and it is believed that the result is due to increased IL-2 sequestration via binding to high affinity IL-2 receptors (CD25) constitutively expressed on Tregs. Thereafter, as the absolute number of Treg increase and there is a further increase in CD25 expression on Tregs during IL-2 therapy (Matsuoka et al. (2013) *Sci. Transl. Med.* 5:179ra43). It has been determined herein that peak Tregs proliferation occurs by 1 week after start of an IL-2 induction regimen in all Treg subsets along with an increase in Tregs population size. Tregs proliferation, however, subsides after week 2 with a fall in Ki-67 expression (proliferation) alongside the preservation of expanded Treg subpopulations at week 12 of IL-2 treatment. A similar temporal pattern of Tregs activation is observed using pSTAT5 and FoxP3 markers, with an initial early generalized enhancement across Treg subpopulations that later subsided during IL-2 treatment despite the continued preservation of enhanced Treg population size. A fall in Treg activation marker expression and a considerable depletion of Treg populations was then observed by 4 weeks after IL-2 discontinuation. Thus, maintenance regimens involving individual patient IL-2 dose escalation, such as after peak plasma IL-2 levels with an induction regimen, restores plasma IL-2 levels and further augment Treg proliferation, activation and neogenesis without inducing Tcon activation or excess adverse events. In this manner, IL-2 induced Treg enhancement occurs in vivo and tachyphylaxis due to diminution of plasma IL-2 levels after binding by increased numbers of circulating Treg with higher CD25 expression is avoided. Accordingly, the methods of the present invention provide unexpectedly enhanced treatment of immune disorders using IL-2 and allow for Tregs and Tcons, either directly or indirectly, to be used as biomarkers of IL-2 efficacy in treating such immune disorders.

I. Definitions

The articles "a" and "an" are used herein to refer to one or to more than one (i.e. to at least one) of the grammatical object of the article. By way of example, "an element" means one element or more than one element.

The term "altered amount" or "altered level" refers to increased or decreased copy number (e.g., germline and/or somatic) of a biomarker nucleic acid, e.g., increased or decreased expression level in a biological sample, as compared to the expression level or copy number of the biomarker nucleic acid in a control sample. The term "altered amount" of a biomarker also includes an increased or decreased protein level of a biomarker protein in a sample, e.g., an immune disorder sample, as compared to the corresponding protein level in a normal, control sample. Furthermore, an altered amount of a biomarker protein may be determined by detecting posttranslational modification such as methylation status of the marker, which may affect the expression or activity of the biomarker protein.

The amount of a biomarker in a subject is "significantly" higher or lower than the normal amount of the biomarker, if the amount of the biomarker is greater or less, respectively, than the normal level by an amount greater than the standard error of the assay employed to assess amount, and preferably at least 20%, 30%, 40%, 50%, 60%, 70%, 80%, 90%, 100%, 150%, 200%, 300%, 350%, 400%, 500%, 600%, 700%, 800%, 900%, 1000% or than that amount. Alternatively, the amount of the biomarker in the subject can be considered "significantly" higher or lower than the normal amount if the amount is at least about two, and preferably at least about three, four, or five times, higher or lower, respectively, than the normal amount of the biomarker.

The term "altered level of expression" of a biomarker refers to an expression level or copy number of the biomarker in a test sample, e.g., a sample derived from a patient suffering from an immune disorder, that is greater or less than the standard error of the assay employed to assess expression or copy number, and is preferably at least twice, and more preferably three, four, five or ten or more times the expression level or copy number of the biomarker in a control sample (e.g., sample from a healthy subjects not having the associated disease) and preferably, the average expression level or copy number of the biomarker in several control samples. The altered level of expression is greater or less than the standard error of the assay employed to assess expression or copy number, and is preferably at least twice, and more preferably three, four, five or ten or more times the expression level or copy number of the biomarker in a control sample (e.g., sample from a healthy subjects not having the associated disease) and preferably, the average expression level or copy number of the biomarker in several control samples.

The term "altered activity" of a biomarker refers to an activity of the biomarker which is increased or decreased in a disease state, e.g., in an immune disorder sample, as compared to the activity of the biomarker in a normal, control sample. Altered activity of the biomarker may be the result of, for example, altered expression of the biomarker, altered protein level of the biomarker, altered structure of the biomarker, or, e.g., an altered interaction with other proteins involved in the same or different pathway as the biomarker or altered interaction with transcriptional activators or inhibitors.

The term "altered structure" of a biomarker refers to the presence of mutations or allelic variants within a biomarker nucleic acid or protein, e.g., mutations which affect expression or activity of the biomarker nucleic acid or protein, as compared to the normal or wild-type gene or protein. For example, mutations include, but are not limited to substitutions, deletions, or addition mutations. Mutations may be present in the coding or non-coding region of the biomarker nucleic acid.

Unless otherwise specified here within, the terms "antibody" and "antibodies" broadly encompass naturally-occurring forms of antibodies (e.g. IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

The term "antibody" as used herein also includes an "antigen-binding portion" of an antibody (or simply "antibody portion"). The term "antigen-binding portion", as used herein, refers to one or more fragments of an antibody that retain the ability to specifically bind to an antigen (e.g., a biomarker polypeptide or fragment thereof). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see e.g., Bird et al. (1988) *Science* 242:423-426; and Huston et al. (1988) *Proc. Natl. Acad. Sci. USA* 85:5879-5883; and Osbourn et al. 1998, Nature Biotechnology 16: 778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VII and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger et al. (1993) *Proc. Natl. Acad. Sci. U.S.A.* 90:6444-6448; Poljak et al. (1994) *Structure* 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov et al. (1995) *Human Antibodies and Hybridomas* 6:93-101) and use of a cysteine residue, biomarker peptide and a C-terminal polyhistidine tag to make bivalent and biotinylated scFv polypeptides (Kipriyanov et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

Antibodies may be polyclonal or monoclonal; xenogeneic, allogeneic, or syngeneic; or modified forms thereof (e.g. humanized, chimeric, etc.). Antibodies may also be fully human. Preferably, antibodies of the invention bind specifically or substantially specifically to a biomarker polypeptide or fragment thereof. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

Antibodies may also be "humanized," which is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the invention may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

The term "assigned score" refers to the numerical value designated for each of the biomarkers after being measured in a patient sample. The assigned score correlates to the absence, presence or inferred amount of the biomarker in the sample. The assigned score can be generated manually (e.g., by visual inspection) or with the aid of instrumentation for image acquisition and analysis. In certain embodiments, the assigned score is determined by a qualitative assessment, for example, detection of a fluorescent readout on a graded scale, or quantitative assessment. In one embodiment, an "aggregate score," which refers to the combination of assigned scores from a plurality of measured biomarkers, is determined. In one embodiment the aggregate score is a summation of assigned scores. In another embodiment, combination of assigned scores involves performing mathematical operations on the assigned scores before combining them into an aggregate score. In certain, embodiments, the aggregate score is also referred to herein as the predictive score.

The term "biomarker" refers to a measurable entity of the present invention that has been determined to be predictive of anti-immune disorder therapy and/or effect treatment of the anti-immune disorder (e.g., multiple-variable dose IL-2 therapy alone or in combination with one or more other anti-immune disorder therapies). Biomarkers can include, without limitation, cell types (e.g., Tregs and/or Tcons), cell ratios (e.g., Tregs to Tcons ratio), nucleic acids (e.g., genomic nucleic acids and/or transcribed nucleic acids) and proteins, particularly those involved shown in Table 1. Biomarkers can further include immunological targets or agents that downregulate unwanted immune reactions in order to treat the immune disorder of interest as described further herein.

A "blocking" antibody or an antibody "antagonist" is one which inhibits or reduces at least one biological activity of the antigen(s) it binds. In certain embodiments, the blocking antibodies or antagonist antibodies or fragments thereof described herein substantially or completely inhibit a given biological activity of the antigen(s).

The term "body fluid" refers to fluids that are excreted or secreted from the body as well as fluid that are normally not (e.g. amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, and vomit). In certain embodiments, body fluids comprising lymphocytes, such as T lymphocytes and subpopulations thereof, are used.

The term "coding region" refers to regions of a nucleotide sequence comprising codons which are translated into amino acid residues, whereas the term "non-coding region" refers to regions of a nucleotide sequence that are not translated into amino acids (e.g., 5' and 3' untranslated regions).

The term "complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

The term "control" refers to any reference standard suitable to provide a comparison to the expression products in the test sample. In one embodiment, the control comprises obtaining a "control sample" from which expression product levels are detected and compared to the expression product levels from the test sample. Such a control sample may comprise any suitable sample, including but not limited to a sample from a control immune disorder patient (can be stored sample or previous sample measurement) with a known outcome; normal tissue or cells isolated from a subject, such as a normal patient or the immune disorder patient, cultured primary cells/tissues isolated from a subject such as a normal subject or the immune disorder patient, adjacent normal cells/tissues obtained from the same organ or body location of the immune disorder patient, a tissue or cell sample isolated from a normal subject, or a primary cells/tissues obtained from a depository. In another preferred embodiment, the control may comprise a reference standard expression product level from any suitable source, including but not limited to housekeeping genes, an expression product level range from normal tissue (or other previously analyzed control sample), a previously determined expression product level range within a test sample from a group of patients, or a set of patients with a certain outcome (for example, survival for one, two, three, four years, etc.) or receiving a certain treatment (for example, standard of care immune disorder therapy). It will be understood by those of skill in the art that such control samples and reference standard expression product levels can be used in combination as controls in the methods of the present invention. In one embodiment, the control may comprise normal or non-immune disorder cell/tissue sample. In another preferred embodiment, the control may comprise an expression level for a set of patients, such as a set of immune disorder patients, or for a set of immune disorder patients receiving a certain treatment, or for a set of patients with one outcome versus another outcome. In the former case, the specific expression product level of each patient can be assigned to a percentile level of expression, or expressed as either higher or lower than the mean or average of the reference standard expression level. In another preferred embodiment, the control may comprise normal cells, cells from patients treated with combination chemotherapy, and cells from patients having an immune disorder that has responded to a treatment of interest. In another embodiment, the control may also comprise a measured value for example, average level of expression of a particular gene in a population compared to the level of expression of a housekeeping gene in the same population. Such a population may comprise normal subjects, immune disorder patients who have not undergone any treatment (i.e., treatment naive), immune disorder patients undergoing standard of care therapy, or patients having an immune disorder that has responded to a treatment of interest. In another preferred embodiment, the control comprises a ratio transformation of expression product levels, including but not limited to determining a ratio of expression product levels of two cell types and/or genes in the test sample and comparing it to any suitable ratio of the same two cell types and/or genes in a reference standard; determining expression product levels of the two or more cell types and/or genes in the test sample and determining a difference in expression product levels in any suitable control; and determining expression product levels of the two or more cell types and/or genes in the test sample, normalizing their expression to expression of housekeeping cell types and/or genes in the test sample, and comparing to any suitable control. In particularly preferred embodiments, the control comprises a control sample which is of the same lineage and/or type as the test sample. In another embodiment, the control may comprise expression product levels grouped as percentiles within or based on a set of patient samples, such as all patients with the immune disorder. In one embodiment a control expression product level is established wherein higher or lower levels of expression product relative to, for instance, a particular percentile, are used as the basis for predicting outcome. In another preferred embodiment, a control expression product level is established using expression product levels from immune disorder control patients with a known outcome, and the expression product levels from the test sample are compared to the control expression product level as the basis for predicting outcome. As demonstrated by the data below, the methods of the invention are not limited to use of a specific cut-point in comparing the level of expression product in the test sample to the control.

The "copy number" of a biomarker nucleic acid refers to the number of DNA sequences in a cell (e.g., germline and/or somatic) encoding a particular gene product. Generally, for a given gene, a mammal has two copies of each gene. The copy number can be increased, however, by gene amplification or duplication, or reduced by deletion. For example, germline copy number changes include changes at one or more genomic loci, wherein said one or more genomic loci are not accounted for by the number of copies in the normal complement of germline copies in a control (e.g., the normal copy number in germline DNA for the same species as that from which the specific germline DNA and corresponding copy number were determined). Somatic copy number changes include changes at one or more genomic loci, wherein said one or more genomic loci are not accounted for by the number of copies in germline DNA of a control (e.g., copy number in germline DNA for the same subject as that from which the somatic DNA and corresponding copy number were determined).

The "normal" copy number (e.g., germline and/or somatic) of a biomarker nucleic acid or "normal" level of expression of a biomarker nucleic acid, or protein is the activity/level of expression or copy number in a biological sample, e.g., a sample containing tissue, whole blood, serum, plasma, buccal scrape, saliva, cerebrospinal fluid, urine, stool, and bone marrow, from a subject, e.g., a human, not afflicted with an immune disorder, or from a corresponding non-immune disorder tissue in the same subject who has an immune disorder.

The term "determining a suitable treatment regimen for the subject" is taken to mean the determination of a treatment regimen (i.e., a single therapy or a combination of different therapies that are used for the prevention and/or treatment of an immune disorder in the subject) for a subject that is started, modified and/or ended based or essentially based or at least partially based on the results of the analysis according to the present invention. One example is determining whether to provide targeted therapy against the immune disorder to provide anti-immune disorder therapy (e.g., multiple-variable dose IL-2 therapy alone or in combination with one or more other anti-immune disorder therapies). The determination can, in addition to the results of the analysis according to the present invention, be based on personal characteristics of the subject to be treated. In most cases, the actual determination of the suitable treatment regimen for the subject will be performed by the attending physician or doctor.

The term "expression signature" or "signature" refers to a group of two or more coordinately expressed biomarkers. For example, the genes, proteins, and the like making up this signature may be expressed in a specific cell lineage, stage of differentiation, or during a particular biological response. The biomarkers can reflect biological aspects of the cell types in which they are expressed. Expression data and gene expression levels can be stored on computer readable media, e.g., the computer readable medium used in conjunction with a microarray or chip reading device. Such expression data can be manipulated to generate expression signatures.

A molecule or cell is "fixed" or "affixed" to a substrate if it is covalently or non-covalently associated with the substrate such that the substrate can be rinsed with a fluid (e.g. standard saline citrate, pH 7.4) without a substantial fraction of the molecule or cell dissociating from the substrate.

The term "homologous" refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATT-GCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

The term "immune disorders" refers to conditions characterized by an unwanted immune response such that a desired anti-immune disorder response suppresses the immune response. Such conditions in which downregulation of an immune response is desired are well known in the art and include, without limitation, situations of tissue, skin and organ transplantation, in graft-versus-host disease (GVHD), inflammation, or in autoimmune diseases, such as systemic lupus erythematosus, multiple sclerosis, allergy, hypersensitivity response, parasitic and viral infections, a disorder requiring increased CD4+ T cell production or function, a disorder requiring improved vaccination efficiency, and a disorder requiring increased regulatory T cell production or function, as described further herein.

The term "inhibit" includes the decrease, limitation, or blockage, of, for example a particular action, function, or interaction. In some embodiments, an immune disorder is "inhibited" if at least one symptom of the immune disorder is alleviated, terminated, slowed, or prevented. As used herein, an immune disorder is also "inhibited" if recurrence or spread of the immune disorder is reduced, slowed, delayed, or prevented.

The term "interaction", when referring to an interaction between two molecules, refers to the physical contact (e.g., binding) of the molecules with one another. Generally, such an interaction results in an activity (which produces a biological effect) of one or both of said molecules.

An "isolated protein" refers to a protein that is substantially free of other proteins, cellular material, separation medium, and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the antibody, polypeptide, peptide or fusion protein is derived, or substantially free from chemical precursors or other chemicals when chemically synthesized. The language "substantially free of cellular material" includes preparations of a biomarker polypeptide or fragment thereof, in which the protein is separated from cellular components of the cells from which it is isolated or recombinantly produced. In one embodiment, the language "substantially free of cellular material" includes preparations of a biomarker protein or fragment thereof, having less than about 30% (by dry weight) of non-biomarker protein (also referred to herein as a "contaminating protein"), more preferably less than about 20% of non-biomarker protein, still more preferably less than about 10% of non-biomarker protein, and most preferably less than about 5% non-biomarker protein. When antibody, polypeptide, peptide or fusion protein or fragment thereof, e.g., a biologically active fragment thereof, is recombinantly produced, it is also preferably substantially free of culture medium, i.e., culture medium represents less than about 20%, more preferably less than about 10%, and most preferably less than about 5% of the volume of the protein preparation.

A "kit" is any manufacture (e.g. a package or container) comprising at least one reagent, e.g. a therapeutic, probe, small molecule, and the like, for specifically detecting and/or therapeutically affecting the expression of a marker of the present invention. The kit may be promoted, distributed, or sold as a unit for performing the methods of the present invention. The kit may comprise one or more reagents necessary to express a composition useful in the methods of the present invention. In certain embodiments, the kit may further comprise a reference standard, e.g., a nucleic acid encoding a protein that does not affect or regulate signaling pathways controlling immunological responses, cell growth, division, migration, survival, or apoptosis. One skilled in the art can envision many such control proteins, including, but not limited to, common molecular tags (e.g., green fluorescent protein and beta-galactosidase), proteins not classified in any of pathway encompassing cell growth, division, migration, survival or apoptosis by GeneOntology reference, or ubiquitous housekeeping proteins. Reagents in the kit may be provided in individual containers or as mixtures of two or more reagents in a single container. In addition, instructional materials which describe the use of the compositions within the kit can be included.

The "normal" level of expression of a biomarker is the level of expression of the biomarker in cells of a subject, e.g., a human patient, not afflicted with an immune disorder. An "over-expression" or "significantly higher level of expression" of a biomarker refers to an expression level in a test sample that is greater than the standard error of the assay employed to assess expression, and is preferably at least 10%, and more preferably 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the biomarker in a control sample (e.g., sample from a healthy subject not having the biomarker associated disease) and preferably, the average expression level of the biomarker in several control samples. A "significantly lower level of expression" of a biomarker refers to an expression level in a test sample that is at least 10%, and more preferably 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the biomarker in a control sample (e.g., sample from a healthy subject not having the biomarker associated disease) and preferably, the average expression level of the biomarker in several control samples. Such "significance" levels can also be applied to any other measured parameter described herein, such as for expression, inhibition, cytotoxicity, cell growth, and the like.

The term "predictive" includes the use of a biomarker for determining the likelihood of response of an immune disorder to anti-immune disorder therapy, such as multiple-variable dose IL-2 therapy alone or in combination with one or more other anti-immune disorder therapies. Such predictive use of the biomarker may be confirmed by, e.g., (1) increased or decreased copy number (e.g., by FISH, FISH plus SKY, single-molecule sequencing, e.g., as described in the art at least at J. Biotechnol., 86:289-301, or qPCR), overexpression or underexpression of a biomarker nucleic acid (e.g., by ISH, Northern Blot, or qPCR), increased or decreased biomarker cells or cell ratios (e.g., by cell sorting and/or counting), protein (e.g., by IHC) and/or biomarker target, or increased or decreased activity, e.g., in more than about 5%, 6%, 7%, 8%, 9%, 10%, 11%, 12%, 13%, 14%, 15%, 20%, 25%, 30%, 40%, 50%, 60%, 70%, 80%, 90%, 95%, 100%, or more of assayed immune disorder samples; (2) its absolute or relatively modulated presence or absence in a biological sample, e.g., a sample containing tissue, whole blood, serum, plasma, buccal scrape, saliva, cerebrospinal fluid, urine, stool, or bone marrow, from a subject, e.g. a human, afflicted with an immune disorder; (3) its absolute or relatively modulated presence or absence in clinical subset of patients with an immune disorder (e.g., those responding to a particular anti-immune disorder therapy (e.g., multiple-variable dose IL-2 therapy alone or in combination with one or more other anti-immune disorder therapies) or those developing resistance thereto).

The terms "prevent," "preventing," "prevention," "prophylactic treatment," and the like refer to reducing the probability of developing a disease, disorder, or condition in a subject, who does not have, but is at risk of or susceptible to developing a disease, disorder, or condition.

The term "probe" refers to any molecule which is capable of selectively binding to a specifically intended target molecule, for example, a nucleotide transcript or protein encoded by or corresponding to a biomarker nucleic acid. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic molecules.

The term "prognosis" includes a prediction of the probable course and outcome of an immune disorder or the likelihood of recovery from the disease. In some embodiments, the use of statistical algorithms provides a prognosis of the immune disorder in an individual. For example, the prognosis can be surgery, development of a clinical subtype of the immune disorder (e.g., GVHD subtype such as chronic GVHD), development of one or more clinical factors, or recovery from the disease.

The term "response to anti-immune disorder therapy (e.g., multiple-variable dose IL-2 therapy alone or in combination with one or more other anti-immune disorder therapies)" relates to any response of the immune disorder (e.g., GVHD) to an anti-immune disorder therapy (e.g., multiple-variable dose IL-2 therapy alone or in combination with one or more other anti-immune disorder therapies). Anti-immune disorder response may be assessed according to well-known methods in the art, including those criteria described in the Examples. Response may be recorded in a quantitative fashion like percentage change or in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of response may be done early after the onset of neoadjuvant or adjuvant therapy, e.g., after a few hours, days, weeks or preferably after a few months. In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular anti-immune disorder therapeutic regimen is at least 25%, 30%, 35%, 40%, 45%, 50%, 55%, 60%, 65%, 70%, 75%, 80%, 85%, or more. Additional criteria for evaluating the response to anti-immune disorder therapies are related to "survival," which includes all of the following: survival until mortality, also known as overall survival (wherein said mortality may be either irrespective of cause or tumor related); "recurrence-free survival" (wherein the term recurrence shall include both localized and distant recurrence); disease free survival (wherein the term disease shall include immune disorders and diseases associated therewith). The length of said survival may be calculated by reference to a defined start point (e.g., time of diagnosis or start of treatment) and end point (e.g., death or recurrence). In addition, criteria for efficacy of treatment can be expanded to include probability of survival, probability of recurrence within a given time period, and the like. For example, in order to determine appropriate threshold values, a particular therapeutic regimen can be administered to a population of subjects and the outcome can be correlated to biomarker measurements that were determined prior to administration of any therapy. The outcome measurement may be pathologic response to therapy given in the neoadjuvant setting. Alternatively, outcome measures, such as overall survival and disease-free survival can be monitored over a period of time for subjects following therapy for whom biomarker measurement values are known. The period of time for which subjects are monitored can vary. For example, subjects may be monitored for at least 0.25, 0.5, 0.75, 1, 2, 3, 4, 5, 6, 7, 8, 9, 10, 12, 14, 16, 18, 20, 25, 30, 35, 40, 45, 50, 55, or 60 months. Biomarker measurement threshold values that correlate to outcome of an anti-immune disorder therapy can be determined using well-known methods in the art, such as those described in the Examples section.

The terms can also refer to an improved prognosis, for example, as reflected by an increased time to recurrence, which is the period to first recurrence censoring for second independent immune disorders as a first event or death without evidence of recurrence, or an increased overall survival, which is the period from treatment to death from any cause. To respond or to have a response means there is a beneficial endpoint attained when exposed to a stimulus. Alternatively, a negative or detrimental symptom is minimized, mitigated or attenuated on exposure to a stimulus. It will be appreciated that evaluating the likelihood that a tumor or subject will exhibit a favorable response is equivalent to evaluating the likelihood that the tumor or subject will not exhibit favorable response (i.e., will exhibit a lack of response or be non-responsive).

An "RNA interfering agent" as used herein, is defined as any agent which interferes with or inhibits expression of a target biomarker gene by RNA interference (RNAi). Such RNA interfering agents include, but are not limited to, nucleic acid molecules including RNA molecules which are homologous to the target biomarker gene of the invention, or a fragment thereof, short interfering RNA (siRNA), and small molecules which interfere with or inhibit expression of a target biomarker nucleic acid by RNA interference (RNAi).

"RNA interference (RNAi)" is an evolutionarily conserved process whereby the expression or introduction of RNA of a sequence that is identical or highly similar to a target biomarker nucleic acid results in the sequence specific degradation or specific post-transcriptional gene silencing (PTGS) of messenger RNA (mRNA) transcribed from that targeted gene (see Coburn, G. and Cullen, B. (2002) *J. of Virology* 76(18):9225), thereby inhibiting expression of the target biomarker nucleic acid. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex that recognizes and cleaves target mRNAs. RNAi can also be initiated by introducing nucleic acid molecules, e.g., synthetic siRNAs, shRNAs, or other RNA interfering agents, to inhibit or silence the expression of target biomarker nucleic acids. As used herein, "inhibition of target biomarker nucleic acid expression" or "inhibition of marker gene expression" includes any decrease in expression or protein activity or level of the target biomarker nucleic acid or protein encoded by the target biomarker nucleic acid. The decrease may be of at least 30%, 40%, 50%, 60%, 70%, 80%, 90%, 95% or 99% or more as compared to the expression of a target biomarker nucleic acid or the activity or level of the protein encoded by a target biomarker nucleic acid which has not been targeted by an RNA interfering agent.

The term "sample" used for detecting or determining the presence or level of at least one biomarker is typically whole blood, plasma, serum, saliva, urine, stool (e.g., feces), tears, and any other bodily fluid (e.g., as described above under the definition of "body fluids"), or a tissue sample (e.g., biopsy) such as a small intestine, colon sample, or surgical resection tissue. In certain instances, the method of the present invention further comprises obtaining the sample from the individual prior to detecting or determining the presence or level of at least one marker in the sample. In some embodiments, any sample comprising T lymphocytes or subsets thereof are useful according to the present invention.

The term "synergistic effect" refers to the combined effect of two or more anti-immune disorder agents or therapies can be greater than the sum of the separate effects of each such agent or therapy alone.

The term "subject" refers to any healthy animal, mammal or human, or any animal, mammal or human afflicted with an immune disorder. The term "subject" is interchangeable with "patient."

The term "survival" includes all of the following: survival until mortality, also known as overall survival (wherein said mortality may be either irrespective of cause or tumor related); "recurrence-free survival" (wherein the term recurrence shall include both localized and distant recurrence); disease free survival (wherein the term disease shall include immune disorders and diseases associated therewith). The length of said survival may be calculated by reference to a defined start point (e.g. time of diagnosis or start of treatment) and end point (e.g. death, recurrence or metastasis). In addition, criteria for efficacy of treatment can be expanded to include response to therapy, probability of survival, probability of recurrence within a given time period, and the like.

The term "therapeutic effect" refers to a local or systemic effect in animals, particularly mammals, and more particularly humans, caused by a pharmacologically active substance. The term thus means any substance intended for use in the diagnosis, cure, mitigation, treatment or prevention of disease or in the enhancement of desirable physical or mental development and conditions in an animal or human. The phrase "therapeutically-effective amount" means that amount of such a therapy or substance that produces some desired local or systemic effect at a reasonable benefit/risk ratio applicable to any treatment. In certain embodiments, a therapeutically effective amount of a compound will depend on its therapeutic index, solubility, and the like. For example, certain compounds discovered by the methods of the present invention may be administered in a sufficient amount to produce a reasonable benefit/risk ratio applicable to such treatment.

A "transcribed polynucleotide" or "nucleotide transcript" is a polynucleotide (e.g. an mRNA, hnRNA, a cDNA, or an analog of such RNA or cDNA) which is complementary to or homologous with all or a portion of a mature mRNA made by transcription of a biomarker nucleic acid and normal post-transcriptional processing (e.g. splicing), if any, of the RNA transcript, and reverse transcription of the RNA transcript.

I. Tregs, Tcons, the Tregs/Tcons Ratio

Regulatory T-cells (Tregs) are naturally occurring CD4+ CD25+FOXP3+ T lymphocytes that comprise ~5-10% of the circulating CD4+ T cell population, act to dominantly suppress autoreactive lymphocytes, and control innate and adaptive immune responses (Piccirillo and Shevach (2004) Semin. Immunol. 16:81-88; Fehervari and Sakaguchi (2004) Curr. Opin. Immunol. 16:203-208; Azuma et al. (2003) Cancer Res. 63:4516-4520; Cederbom et al. (2000) Eur. J. Immunol. 30:1538-1543; Maloy et al. (2003) J. Exp. Med. 197:111-119; Serra et al. (2003) Immunity 19:877-889; Thornton and Shevach (1998) J. Exp. Med. 188:287-296; Janssens et al. (2003) J. Immunol. 171:4604-4612; Gasteiger et al. (2013) J. Exp. Med. 210:1167-1178; Sitrin et al. (2013) J. Exp. Med. 210:1153-1165). Tregs achieve this suppressing, at least in part, by inhibiting the proliferation, expansion, and effector activity of conventional T cells (Tcons). They also suppress effector T cells from destroying their (self-)target, either through cell-cell contact by inhibiting T cell help and activation, or through release of immunosuppressive cytokines such as IL-10 or TGF-β. Depletion of $T_{reg}$ cells was shown to enhance IL-2 induced anti-tumor immunity (Imai et al. (2007) Cancer Sci. 98:416-23).

Tcons are conventional T cells, also known as Tconv, that have effector functions (e.g., cytokine secretion, cytotoxic activity, and the like) to increase immune responses by virtue of their expression of one or more T cell receptors. Tcons are defined as any T cell population that is not a Treg and include, for example, naive T cells, activated T cells, memory T cells, resting Tcons, or Tcons that have differentiated toward, for example, the Th1 or Th2 lineages. "Naïve Tcons" are CD4+ T cells that have differentiated in bone marrow, and successfully underwent a positive and negative processes of central selection in a thymus, but have not yet been activated by exposure to an antigen. Naive Tcons are commonly characterized by surface expression of L-selectin (CD62L), absence of activation markers such as CD25, CD44 or CD69, and absence of memory markers such as CD45RO. Naïve Tcons are therefore believed to be quiescent and non-dividing, requiring interleukin-7 (IL-7) and interleukin-15 (IL-15) for homeostatic survival (see, at least WO 2010/101870). The presence and activity of such cells are undesired in the context of suppressing immune responses. Unlike Tregs, Tcons are not anergic and can proliferate in response to antigen-based T cell receptor activation (Lechler et al. (2001) Philos. Trans. R. Soc. Lond. Biol. Sci. 356:625-637).

Thus, increasing the number of Tregs, increasing Treg activity, and/or decreasing Treg cell death (e.g., apoptosis) is useful for suppressing unwanted immune reactions associated with a range of immune disorders (e.g., cGVHD). For example, in a murine model a 1:1 mix of CD4+CD25+ Tregs and CD25− effector T cells added to donor bone marrow stem cells suppressed alloimmune activation and GVHD without increasing malignant relapse post-transplant (Edinger et al. (2003) Nat. Med. 9:1144-1150). In humans, impaired Treg reconstitution in HSCT recipients occurs with active cGVHD (Zorn et al. (2005) Blood 106:2903-2911). In participants with active cGVHD, impaired Tregs reconstitution, low levels of telomerase, and shortened telomeres, are believed to contribute to decreased survival of Tregs (Zorn et al. (2005) Blood 106:2903-2911; Matsuoka et al. (2010) J. Clin. Invest. 120:1479-1493; Kawano et al. (2011) Blood 118:5021-5030). The role of IL-2 in Tregs homeostasis and function is believed to account for its limited efficacy as an anti-immune disorder therapy, and explain in part the finding that in vivo administration of IL-2 plus syngeneic T-cell-depleted donor marrow prevents GVHD after MHC-mismatched murine allo-SCT, without impacting GVL responses (Sykes et al. (1990) Proc. Natl. Acad. Sci. U.S.A. 87:5633-5647; Sykes et al. (1990) J. Exp. Med. 171:645-658). In murine allo-HSCT models, co-infusion of Treg expanded ex-vivo with IL-2 also resulted in suppression of GVHD, with improved immune reconstitution and preserved GVL responses (Taylor et al. (2002) Blood 99:3493-3499; Trenado et al. (2003) J. Clin. Invest. 112: 1688-1696).

Tregs are also important in suppressing inflammation as well. In the context of ongoing inflammation, it is critical that treatments preferentially enhance Tregs without activating conventional T cells (Tcons) or other effectors that may worsen GVHD. Effective augmentation of Tregs in vivo is also directly relevant to other disorders of impaired peripheral tolerance (e.g., autoimmune diseases like SLE, T1D, MS, psoriasis, RA, IBD, vasculitis), where Treg dysfunction is increasingly implicated (Grinberg-Bleyer et al. (2010) J. Exp. Med. 207:1871-1878; Buckner (2010) Nat. Rev. Immunol. 10:849-859; Humrich et al. (2010) Proc. Natl. Acad. Sci. U.S.A. 107:204-209; Carbone et al. (2014) Nat. Med. 20:69-74).

II. Interleukin-2 (IL-2)

The term "interleukin-2 (IL-2)" or "T cell growth factor (TCGF)" refers to a 15.5 kDa globular glycoprotein playing a central role in lymphocyte generation, survival and homeostasis. The term includes any purified or recombinant IL-2 molecule that possesses an immune inhibiting effect (e.g., by way of an increase in Tregs, an increase in the ratio of Tregs to Tcons, an increase in Treg proliferation, an increase in Treg function, and the like), including, but not limited to, modified native IL-2 molecules, truncated IL-2 molecules, variant IL-2 molecules, and covalently modified IL-2 molecules (e.g., glycosylated or fusion protein forms).

IL-2 consists of four antiparallel, amphiphatic α-helices that form a quaternary structure important for its function (Smith (1988) Science 240:1169-1176; Bazan (1992) Science 257:410-413). Nucleic acid and polypeptide sequences of human IL-2 are well known in the art. For example, the cDNA sequence of NM_000586.3 available on the GenBank database maintained by the U.S. National Center for Biotechnology Information encodes precursor IL-2 protein (NP_000577.2), wherein residues 1-20 represent the signal peptide and the remaining residues represent the mature cytokine. In some embodiments, the first 20, 21, 22, or more amino acids can be removed as the signal peptide in order to produce the mature cytokine. Nucleic acid and pro-polypeptide sequences of IL-2 orthologs in species other than humans are also well known and include, for example, chimpanzee IL-2 (XM_517425.3 and XP_517425.1), monkey IL-2 (NM_001047130.1 and NP_001040595.1), dog IL-2 (NM_001003305.1 and NP_001003305.1), mouse IL-2 (NM_008366.3 and NP_032392.1), and rat IL-2 (NM_053836.1 and NP_446288.1). Residues 1-20 of each pro-polypeptide represent the signal peptide and the remaining residues represent the mature cytokine.

Representative sequences of IL-2 orthologs are presented below in Table 1. It is to be noted that the term can further be used to refer to any combination of features described herein regarding IL-2 molecules. For example, any combination of sequence composition, percentage identify, sequence length, domain structure, functional activity, etc. can be used to describe an IL-2 molecule of the present invention.

In still other embodiments, the term "IL-2" comprises des-alanyl-1, serine-125 human IL-2 (PROLEUKIN® (aldesleukin); Novartis Inc., & Prometheus Laboratories, Inc.) and/or a recombinant human IL-2 produced in yeast (RONCOLEUKIN®). Aldesleukin is supplied as a sterile, white to off-white, lyophilized cake in single-use vials containing 22 MIU of aldesleukin. For the 22 million international unit (MIU) vial, when reconstituted with 1.2 mL Sterile Water for Injection (SWFI), each mL contains 18 MIU (1.1 mg) IL-2, 50 mg mannitol and ~180 mcg sodium dodecyl sulphate, buffered with ~170 mcg sodium phosphate monobasic and 890 mcg sodium phosphate dibasic to a pH of 7.5 (range: 7.2-7.8). In contrast to native IL-2, recombinant IL-2 is non-glycosylated and differs at two amino acid positions. There are no discernable functional differences between native and recombinant forms of IL-2.

Exemplary IL-2 variants, recombinant IL-2, methods of IL-2 production, methods of IL-2 purification, methods of formulation, and the like are well known in the art and can be found, for example, at least in U.S. Pat. Nos. 4,530,787, 4,569,790, 4,572,798, 4,604,377, 4,748,234, 4,853,332, 4,959,314, 5,464,939, RE33,653, 5,229,109, 7,514,073, and 7,569,215, each of which is herein incorporated by reference in their entirety for all purposes.

For example, a biomarker nucleic acid molecules that differ, due to degeneracy of the genetic code, from the nucleotide sequence of nucleic acid molecules encoding a protein which corresponds to the biomarker, and thus encode the same protein, are contemplated. There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
| --- | --- |
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (GlU, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Praline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA encoding a biomarker nucleic acid (or any portion thereof) can be used to derive the polypeptide amino acid sequence, using the genetic code to translate the DNA or RNA into an amino acid sequence. Likewise, for polypeptide amino acid sequence, corresponding nucleotide sequences that can encode the polypeptide can be deduced from the genetic code (which, because of its redundancy, will produce multiple nucleic acid sequences for any given amino acid sequence). Thus, description and/or disclosure herein of a nucleotide sequence which encodes a polypeptide should be considered to also include description and/or disclosure of the amino acid sequence encoded by the nucleotide sequence. Similarly, description and/or disclosure of a polypeptide amino acid sequence herein should be considered to also include description and/or disclosure of all possible nucleotide sequences that can encode the amino acid sequence.

In addition, it will be appreciated by those skilled in the art that DNA sequence polymorphisms that lead to changes in the amino acid sequence can exist within a population (e.g., the human population). Such genetic polymorphisms can exist among individuals within a population due to natural allelic variation. An allele is one of a group of genes which occur alternatively at a given genetic locus. In addition, it will be appreciated that DNA polymorphisms that affect RNA expression levels can also exist that may affect the overall expression level of that gene (e.g., by affecting regulation or degradation).

The term "allele," which is used interchangeably herein with "allelic variant," refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene or allele. For example, biomarker alleles can differ from each other in a single nucleotide, or several nucleotides, and can include substitutions, deletions, and insertions of nucleotides. An allele of a gene can also be a form of a gene containing one or more mutations.

The term "allelic variant of a polymorphic region of gene" or "allelic variant", used interchangeably herein, refers to an alternative form of a gene having one of several possible nucleotide sequences found in that region of the gene in the population. As used herein, allelic variant is meant to encompass functional allelic variants, non-functional allelic variants, SNPs, mutations and polymorphisms.

The term "single nucleotide polymorphism" (SNP) refers to a polymorphic site occupied by a single nucleotide, which is the site of variation between allelic sequences. The site is usually preceded by and followed by highly conserved sequences of the allele (e.g., sequences that vary in less than $1/100$ or $1/1000$ members of a population). A SNP usually arises due to substitution of one nucleotide for another at the polymorphic site. SNPs can also arise from a deletion of a nucleotide or an insertion of a nucleotide relative to a reference allele. Typically the polymorphic site is occupied by a base other than the reference base. For example, where the reference allele contains the base "T" (thymidine) at the polymorphic site, the altered allele can contain a "C" (cytidine), "G" (guanine), or "A" (adenine) at the polymorphic site. SNP's may occur in protein-coding nucleic acid sequences, in which case they may give rise to a defective or otherwise variant protein, or genetic disease. Such a SNP may alter the coding sequence of the gene and therefore specify another amino acid (a "missense" SNP) or a SNP may introduce a stop codon (a "nonsense" SNP). When a SNP does not alter the amino acid sequence of a protein, the SNP is called "silent." SNP's may also occur in noncoding regions of the nucleotide sequence. This may result in defective protein expression, e.g., as a result of alternative splicing, or it may have no effect on the function of the protein.

As used herein, the terms "gene" and "recombinant gene" refer to nucleic acid molecules comprising an open reading frame encoding a polypeptide corresponding to a marker of the invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

In another embodiment, a biomarker nucleic acid molecule is at least 7, 15, 20, 25, 30, 40, 60, 80, 100, 150, 200, 250, 300, 350, 400, 450, 550, 650, 700, 800, 900, 1000, 1100, 1200, 1300, 1400, 1500, 1600, 1700, 1800, 1900, 2000, 2200, 2400, 2600, 2800, 3000, 3500, 4000, 4500, or more nucleotides in length and hybridizes under stringent conditions to a nucleic acid molecule corresponding to a marker of the invention or to a nucleic acid molecule encoding a protein corresponding to a marker of the invention. As used herein, the term "hybridizes under stringent conditions" is intended to describe conditions for hybridization and washing under which nucleotide sequences at least 60% (65%, 70%, 75%, 80%, preferably 85%) identical to each other typically remain hybridized to each other. Such stringent conditions are known to those skilled in the art and can be found in sections 6.3.1-6.3.6 of *Current Protocols in Molecular Biology*, John Wiley & Sons, N.Y. (1989). A preferred, non-limiting example of stringent hybridization conditions are hybridization in 6× sodium chloride/sodium citrate (SSC) at about 45° C., followed by one or more washes in 0.2×SSC, 0.1% SDS at 50-65° C.

In addition to naturally-occurring allelic variants of a nucleic acid molecule of the invention that can exist in the population, the skilled artisan will further appreciate that sequence changes can be introduced by mutation thereby leading to changes in the amino acid sequence of the encoded protein, without altering the biological activity of the protein encoded thereby. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologs of various species may be non-essential for activity and thus would be likely targets for alteration. Alternatively, amino acid residues that are conserved among the homologs of various species (e.g., murine and human) may be essential for activity and thus would not be likely targets for alteration.

Accordingly, another aspect of the present invention pertains to nucleic acid molecules encoding a polypeptide of the invention that contain changes in amino acid residues that are not essential for activity. Such polypeptides differ in amino acid sequence from the naturally-occurring proteins which correspond to the markers of the invention, yet retain biological activity. In one embodiment, a biomarker protein has an amino acid sequence that is at least about 40% identical, 50%, 60%, 70%, 75%, 80%, 83%, 85%, 87.5%, 90%, 91%, 92%, 93%, 94%, 95%, 96%, 97%, 98%, 99% or identical to the amino acid sequence of a biomarker protein described herein.

An isolated nucleic acid molecule encoding a variant protein can be created by introducing one or more nucleotide substitutions, additions or deletions into the nucleotide sequence of nucleic acids of the invention, such that one or more amino acid residue substitutions, additions, or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

Another aspect of the present invention pertains to the use of biomarker proteins and biologically active portions thereof. In one embodiment, the native polypeptide corresponding to a marker can be isolated from cells or tissue sources by an appropriate purification scheme using standard protein purification techniques. In another embodiment, polypeptides corresponding to a marker of the invention are produced by recombinant DNA techniques. Alternative to recombinant expression, a polypeptide corresponding to a marker of the invention can be synthesized chemically using standard peptide synthesis techniques.

Biologically active portions of a biomarker polypeptide include polypeptides comprising amino acid sequences sufficiently identical to or derived from a biomarker protein amino acid sequence described herein, but which includes fewer amino acids than the full length protein, and exhibit at least one activity of the corresponding full-length protein. Typically, biologically active portions comprise a domain or motif with at least one activity of the corresponding protein. A biologically active portion of a protein of the invention can be a polypeptide which is, for example, 50, 55, 60, 65, 70, 75, 80, 85, 90, 95, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, or more amino acids in length. Moreover, other biologically active portions, in which other regions of the protein are deleted, can be prepared by recombinant techniques and evaluated for one or more of the functional activities of the native form of a polypeptide of the invention.

Preferred polypeptides have an amino acid sequence of a biomarker protein encoded by a nucleic acid molecule described herein. Other useful proteins are substantially identical (e.g., at least about 40%, preferably 50%, 60%, 70%, 75%, 80%, 83%, 85%, 88%, 90%, 91%, 92%, 93%, 94%, 95%, 96%, 97%, 98%, or 99%) to one of these sequences and retain the functional activity of the protein of the corresponding naturally-occurring protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul, et al. (1990) *J. Mol. Biol.* 215:403-410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al. (1997) *Nucleic Acids Res.* 25:3389-3402. Alternatively, PSI-Blast can be used to perform an iterated search which detects distant relationships between molecules. When utilizing BLAST, Gapped BLAST, and PSI-Blast programs, the default parameters of the respective programs (e.g., XBLAST and NBLAST) can be used. See the National Center for Biotechnology Information (NCBI) website at ncbi.nlm.nih.gov. Another preferred, non-limiting example of a mathematical algorithm utilized for the comparison of sequences is the algorithm of Myers and Miller, (1988) *Comput Appl Biosci,* 4:11-7. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Natl. Acad. Sci. USA* 85:2444-2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

The invention also provides chimeric or fusion proteins corresponding to a biomarker protein. As used herein, a "chimeric protein" or "fusion protein" comprises all or part (preferably a biologically active part) of a polypeptide corresponding to a marker of the invention operably linked to a heterologous polypeptide (i.e., a polypeptide other than the polypeptide corresponding to the marker). Within the fusion protein, the term "operably linked" is intended to indicate that the polypeptide of the invention and the heterologous polypeptide are fused in-frame to each other. The heterologous polypeptide can be fused to the amino-terminus or the carboxyl-terminus of the polypeptide of the invention.

One useful fusion protein is a GST fusion protein in which a polypeptide corresponding to a marker of the invention is fused to the carboxyl terminus of GST sequences. Such fusion proteins can facilitate the purification of a recombinant polypeptide of the invention.

In another embodiment, the fusion protein contains a heterologous signal sequence, immunoglobulin fusion protein, toxin, or other useful protein sequence. Chimeric and fusion proteins of the invention can be produced by standard recombinant DNA techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, e.g., Ausubel et al., supra). Moreover, many expression vectors are commercially available that already encode a fusion moiety (e.g., a GST polypeptide). A nucleic acid encoding a polypeptide of the invention can be cloned into such an expression vector such that the fusion moiety is linked in-frame to the polypeptide of the invention.

A signal sequence can be used to facilitate secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the invention pertains to the described polypeptides having a signal sequence, as well as to polypeptides from which the signal sequence has been proteolytically cleaved (i.e., the cleavage products). In one embodiment, a nucleic acid sequence encoding a signal sequence can be operably linked in an expression vector to a protein of interest, such as a protein which is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

The present invention also pertains to variants of the biomarker polypeptides described herein. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Another aspect of the present invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., E. coli) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

TABLE 1

```
SEQ ID NO: 1 Human IL-2 cDNA Sequence
   1 atgtacagga tgcaactcct gtcttgcatt gcactaagtc ttgcacttgt cacaaacagt
  61 gcacctactt caagttctac aaagaaaaca cagctacaac tggagcattt actgctggat
 121 ttacagatga ttttgaatgg aattaataat tacaagaatc ccaaactcac caggatgctc
 181 acatttaagt tttacatgcc caagaaggcc acagaactga aacatcttca gtgtctagaa
 241 gaagaactca aacctctgga ggaagtgcta aatttagctc aaagcaaaaa ctttcactta
 301 agacccaggg acttaatcag caatatcaac gtaatagttc tggaactaaa gggatctgaa
 361 acaacattca tgtgtgaata tgctgatgag acagcaacca ttgtagaatt tctgaacaga
 421 tggattacct tttgtcaaag catcatctca acactgactt ga SEQ ID NO: 2 Human IL-2 Amino Acid Sequence
   1 myrmqllsci alslalvtns aptssstkkt qlqlehllld lqmilnginn yknpkltrml
  61 tfkfympkka telkhlqcle eelkpleevl nlaqsknfhl rprdlisnin vivlelkgse
 121 ttfmceyade tativeflnr witfcqsiis tlt SEQ ID NO: 3 Chimpanzee IL-2 cDNA Sequence
   1 atgtacagga tgcaactcct gtcttgcatt gcactaagtc ttgcacttgt cacaaacagt
  61 gcacctactt caagttctac aaagaaaaca cagctacaac tggagcattt actgctggat
 121 ttacagatga ttttgaatgg aattaataat tacaagaatc ccaaactcac caggatgctc
 181 acatttaagt tttacatgcc caagaaggcc acagaactga aacatcttca gtgtctagaa
 241 gaagaactca aacctctgga ggaagtgcta aatttagctc aaagcaaaaa ctttcactta
 301 agacccaggg acttaatcag caatatcaac gtaatagttc tggaactaaa gggatctgaa
 361 acaacattca tgtgtgaata tgctgatgag acagcaacca ttgtagaatt tctgaacaga
 421 tggattacct tttgtcaaag catcatctca acactgactt ga SEQ ID NO: 4 Chimpanzee IL-2 Amino Acid Sequence
   1 myrmqllsci alslalvtns aptssstkkt qlqlehllld lqmilnginn yknpkltrml
  61 tfkfympkka telkhlqcle eelkpleevl nlaqsknfhl rprdlisnin vivlelkgse
 121 ttfmceyade tativeflnr witfcqsiis tlt SEQ ID NO: 5 Monkey IL-2 cDNA Sequence
   1 atgtacagga tgcaactcct gtcttgcatt gcactaagtc ttgcacttgt cacaaacagt
  61 gcacctactt caagttctac aaagaaaaca cagctacaac tggagcattt actgctggat
 121 ttacagatga ttttgaatgg aattaataat tacaagaatc ccaaactcac caggatgctc
 181 acatttaagt tttacatgcc caagaaggcc acagaattga aacatcttca gtgtctagaa
```

TABLE 1-continued

```
241 gaagaactca aacctctgga ggaagtgcta aatttagctc aaagcaaaaa ctttcactta
301 agagatacca aggacttaat cagcaatatc aacgtaatag ttctggaact aaagggatct
361 gaaacaacac tgatgtgtga atatgctgat gagacagcaa ccattgtaga atttctgaac
421 agatggatta ccttttgtca aagcatcatc tcaacactga cctga SEQ ID NO: 6 Monkey IL-2 Amino Acid Sequence
  1 myrmqllsci alslalvtns aptssstkkt qlqlehllld lqmilnginn yknpkitrml
 61 tfkfympkka telkhlqcle eelkpleevl nlaqsknfhl rdtkdlisni nvivlelkgs
121 ettlmceyad etativefln rwitfcqsii stlt SEQ ID NO: 7 Dog IL-2 cDNA Sequence
  1 atgtacaaaa tgcaactctt gtcttgcatc gcactgacgc ttgtacttgt cgcaaacagt
 61 gcacctatta cttcaagctc tacaaaggaa acagagcaac agatgggaca attactgctg
121 gatttacagt tgcttttgaa tggagttaat aattatgaga accccaact ctccaggatg
181 ctcacattta agttttacac gcccaagaag gccacagaat ttacacacct tcaatgtcta
241 gcagaagaac tcaaaaacct ggaggaagtg ctaggtttac ctcaaagcaa aaacgttcac
301 ttgacagaca ccaaggaatt aatcagcaat atgaatgtaa cacttctgaa actaaaggga
361 tctgaaacaa gttacaactg tgaatatgat gacgagacag caaccattac agaatttctg
421 aacaaatgga ttaccttttg tcaaagcatc ttctcaaacac tgacttga SEQ ID NO: 8 Dog IL-2 Amino Acid Sequence
  1 mykmqllsci altlvlvans apitssstke teqqmeqlll dlqlllngvn nyenpqlsrm
 61 ltfkfytpkk atefthlqcl aeelknleev lglpqsknvh ltdtkelisn mnvtllklkg
121 setsynceyd detatitefl nkwitfcqsi fstlt SEQ ID NO: 9 Mouse IL-2 cDNA Sequence
  1 atgtacagca tgcagctcgc atcctgtgtc acattgacac ttgtgctcct tgtcaacagc
 61 gcacccactt caagctccac ttcaagctct acagcggaag cacagcagca gcagcagcag
121 cagcagcagc agcagcagca cctggagcag ctgttgatgg acctacagga gctcctgagc
181 aggatggaga attacaggaa cctgaaactc cccaggatgc tcaccttcaa attttacttg
241 cccaagcagg ccacagaatt gaaagatctt cagtgcctag aagatgaact tggacctctg
301 cggcatgttc tggatttgac tcaaagcaaa agctttcaat tggaagatgc tgagaatttc
361 atcagcaata tcagagtaac tgttgtaaaa ctaaagggct ctgacaacac atttgagtgc
421 caattcgatg atgagtcagc aactgtggtg gactttctga ggagatggat agccttctgt
481 caaagcatca tctcaacaag ccctcaataa SEQ ID NO: 10 Mouse IL-2 Amino Acid Sequence
  1 mysmqlascv tltlvllvns aptssstsss taeaqqqqqq qqqqqqhleq llmdlqells
 61 rmenyrnlkl prmltfkfyl pkqatelkdl qcledelgpl rhvldltqsk sfqledaenf
121 lsnirvtvvk lkgsdnrfec qfddesatvv dflrrwiafc qsiistspq SEQ ID NO: 11 Rat IL-2 cDNA Sequence
  1 atgtacagca tgcagctcgc atcctgtgtt gcactgacgc ttgtcctcct tgtcaacagc
 61 gcacccactt caagccctgc aaaggaaaca cagcagcacc tggagcagct gttgctggac
121 ttacaggtgc tcctgagagg gatcgataat tacaagaatc tgaaactccc catgatgctc
181 acgtttaaat tttacttgcc caagcaggcc acagaattga aacatcttca gtgcctggaa
241 aatgaactcg gagctctgca gcgtgtgttg gatttgactc aaagcaaaag ctttcacttg
301 gaagacgctg gaaatttcat cagcaatatc agagtaactg ttgtaaaact aaagggctct
361 gaaaacaaat ttgagtgcca attcgatgat gagccagcaa ctgtggtgga atttctgagg
421 agatggatag ccatctgtca aagcatcatc tcaacaatga ctcagtaa SEQ ID NO: 12 Rat IL-2 Amino Acid Sequence
  1 mysmqlascv altlvllvns aptsspaket qqhleqllld lqvllrgidn yknlklpmml
 61 tfkfylpkqa telkhlqcle nelgalqrvl dltqsksfhl edagnfisni tvtvvklkgs
121 enkfecqfdd epatvveflr rwiaicqsii stmtq
```

Included in Table 1 are RNA nucleic acid molecules (e.g., thymines replaced with uredines), nucleic acid molecules encoding orthologs of the encoded proteins, as well as DNA or RNA nucleic acid sequences comprising a nucleic acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with the nucleic acid sequence of any SEQ ID NO listed in Table 1, or a portion thereof. Such nucleic acid molecules can have a function of the full-length nucleic acid as described further herein.

Included in Table 1 are orthologs of the proteins, as well as polypeptide molecules comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with an amino acid sequence of any SEQ ID NO listed in Table 1, or a portion thereof. Such polypeptides can have a function of the full-length polypeptide as described further herein.

IL-2 mediates its action by binding to IL-2 receptors (IL-2R), which consist of up to three individual subunits, the different association of which can produce receptor forms that differ in their affinity to IL-2. Association of the α (CD25), β (CD122), and γ ($γ_c$, CD132) subunits results in a trimeric, high-affinity receptor for IL-2. Dimeric IL-2 receptor consisting of the β and γ subunits is termed intermediate-affinity IL-2R. The a subunit forms the monomeric low affinity IL-2 receptor. Although the dimeric intermediate-affinity IL-2 receptor binds IL-2 with approximately 100-fold lower affinity than the trimeric high-affinity receptor, both the dimeric and the trimeric IL-2 receptor variants are able to transmit signal upon IL-2 binding (Minami et al. (1993) *Annu. Rev. Immunol.* 11:245-268). Hence, the α-subunit, CD25, is not essential for IL-2 signaling. It confers high-affinity binding to its receptor, whereas the τ3 subunit, CD122, and the γ-subunit are crucial for signal transduction (Krieg et al. (2010) *Proc. Natl. Acad. Sci. U.S.A.* 107:11906-11911). Trimeric IL-2 receptors including CD25, are expressed by (resting) $CD4^+$ forkhead box P3 $(FoxP3)^+$ regulatory T cells (Tregs). They are also transiently induced on conventional activated T cells, whereas in the resting state these cells express only dimeric IL-2 receptors. Tregs consistently express the highest level of CD25 in vivo (Fontenot et al. (2005) *Nat. Immunol.* 6:1142-1151).

Native IL-2 was first identified in 1976 as a growth factor for T lymphocytes. It is produced by human cluster designation (CD) 4+ and some CD8+ T-cells and is synthesized mainly by activated T-cells, in particular $CD4^+$ helper T cells. It stimulates the proliferation and differentiation of T cells, induces the generation of cytotoxic T lymphocytes (CTLs) and the differentiation of peripheral blood lymphocytes to cytotoxic cells and lymphokine-activated killer (LAK) cells, promotes cytokine and cytolytic molecule expression by T cells, facilitates the proliferation and differentiation of B-cells and the synthesis of immunoglobulin by B-cells, and stimulates the generation, proliferation and activation of natural killer (NK) cells (see, for example, Waldmann (2009) *Nat. Rev. Immunol.* 6:595-601; Olejniczak and Kasprzak (2008) *Med. Sci. Monit.* 14:ra179-189; Malek (2008) *Annu. Rev. Immunol.* 26:453-479).

IL-2 is known to play a central role in the generation of immune responses. In cancer clinical trials, high-dose recombinant IL-2 (e.g., IV bolus dose of 600,000 international units (IU)/kg every 8 hours for up to 14 doses) demonstrated antitumor activity in metastatic renal cell carcinoma (RCC) and metastatic melanoma. Accordingly, such high-dose IL-2 was approved for the treatment of metastatic RCC in Europe in 1989 and in the US in 1992. In 1998, approval was obtained to treat patients with metastatic melanoma. Recombinant human IL-2 (Aldesleukin) (PROLEUKIN®-Novartis Inc. & Prometheus Labs Inc.) is currently approved by the United States Food and Drug Administration (US FDA).

However, IL-2 has a dual function in the immune response in that it not only mediates expansion and activity of effector cells, but also is crucially involved in maintaining peripheral immune tolerance. A major mechanism underlying peripheral self-tolerance is IL-2 induced activation-induced cell death (AICD) in T cells. AICD is a process by which fully activated T cells undergo programmed cell death through engagement of cell surface-expressed death receptors such as CD95 (also known as Fas) or the TNF receptor. When antigen-activated T cells expressing a high-affinity IL-2 receptor (after previous exposure to IL-2) during proliferation are re-stimulated with antigen via the T cell receptor (TCR)/CD3 complex, the expression of Fas ligand (FasL) and/or tumor necrosis factor (TNF) is induced, making the cells susceptible for Fas-mediated apoptosis. This process is IL-2 dependent (Lenardo (1991) *Nature* 353:858-861) and mediated via STAT5. By the process of AICD in T lymphocytes tolerance can not only be established to self-antigens, but also to persistent antigens that are clearly not part of the host's makeup, such as tumor antigens.

Moreover, IL-2 is also involved in the maintenance of peripheral Tregs (Fontenot et al. (2005) *Nat. Immunol.* 6:1142-1151; D'Cruz and Klein (2005) *Nat. Immunol.* 6:1152-1159; Maloy and Powrie (2005) *Nat. Immunol.* 6:1171-1172). At physiologic concentrations in vivo, IL-2 is required for Tregs development, expansion and survival (Malek and Bayer (2004) *Nat. Rev. Immunol.* 4:665-674; Nelson (2004) *J. Immunol.* 172:3983-3988). In fact, low-dose IL-2 administration early after HSCT, intended to stimulate immune effector cells, actually preferentially expanded Tregs in vivo (Zorn et al. (2006) *Blood* 108:1571-1579) due to the greater expression of high affinity IL-2 receptor a (CD25) on Tregs than on Tcons, which typically express low and intermediate affinity receptors. In humans, IL-2 regulates FOXP3 expression in Tregs and induces Treg expansion in vivo (Zorn et al. (2006) *Blood* 108:1571-1579). Patients having steroid refractory cGVHD respond to low dose IL-2 by preferentially increasing functional Treg in vivo (e.g., a >7-fold rise in Tregs count without impacting CD4+ Tcons count and a median Tregs:Tcons ratio increase of >5 times from baseline (p<0.001)), and ~50% of evaluable patients had objective partial responses (PR) per NIH criteria at sites of cGVHD involvement that included skin, joint/fascia/muscle, liver and peripheral nerves (Koreth et al. (2011) *N. Engl. J. Med.* 365:2055-2066; Pavletic et al. (2006) *Biol. Blood Marrow Transplant.* 12:252-266). For example, 12 of 15 patients with PR or stable disease (SD) with minor response continued on extended-duration IL-2 and 10 of the 12 patients on long-term IL-2 had continued clinical response during a mean 60% glucocorticoid taper (range, 25-100%) over a median 13 month follow-up. Tregs count and Tregs:Tcons ratio remained elevated at 8 weeks (p<0.001 for both vs. baseline), then declined after cessation of IL-2. Moreover IL-2 enhanced Tregs expressed high levels of FoxP3 and were functionally capable of inhibition of autologous Tcons. Tregs immune responses were sustained during extended-duration IL-2 therapy (Koreth et al. (2011) *N. Engl. J. Med.* 365:2055-2066).

Plasma IL-2 levels rose rapidly by week 1, then, despite continued daily IL-2 administration, declined while the Tregs count rose (Matsuoka et al. (2013) *Sci. Transl. Med.* 5:179ra43). As the absolute number of Treg increased, and as there was further increase in CD25 expression on Tregs during IL-2 therapy, IL-2 levels fell. Treg homeostasis was profoundly enhanced, with rapid induction of Treg proliferation within 1 week of initiating IL-2; increase in thymic Treg neogenesis that peaked at week 4-6; and rise in cell survival marker Bcl-2 in Treg from week 4 onwards, that were reversible upon IL-2 discontinuation at week 8 (Matsuoka et al. (2013) *Sci. Transl. Med.* 5:179ra43). The impact on Tcons homeostasis was limited in comparison. Examination of immune function revealed that cGVHD is characterized by constitutive Stat5 activation of CD4 Tcons due to elevated levels of IL-7 and IL-15, with a relative functional deficiency of IL-2 and Treg pSTAT5 activation (Matsuoka et al. (2013) *Sci. Transl. Med.* 5:179ra43). Low-dose IL-2 therapy preferentially enhanced Treg Stat5 phosphorylation in cGVHD patients within 1 week of starting IL-2. The Tregs:Tcons pSTAT5 activation ratio was restored by 2 weeks to the normal range, where it remained for the duration of IL-2 therapy. Apoptosis resistance assessed by spontaneous and Fas-induced assays was also preferentially induced in Tregs compared to Tcons. Low-dose IL-2 could restore the homeostatic balance in favor of Treg versus Tcon, and promote immune tolerance (Matsuoka et al. (2013) *Sci. Transl. Med.* 5:179ra43).

Similar Treg enhancement and clinical benefit was also documented in HCV-induced vasculitis (Saadoun et al. (2011) *N. Engl. J. Med.* 365:2067-2077). Although low-dose IL-2 has not been used for treatment of GVHD in children, it has been used safely for other indications in children following both allogeneic and autologous HSCT. Two studies used SC IL-2 at doses ranging from $1-2 \times 10^6$ IU/m²/d in post-transplant patients with high risk leukemia and/or relapsed metastatic Ewing's sarcoma as a strategy to prevent relapse by inducing natural killer (NK) cells (Liu et al. (2008) *Bone Marrow Transplant* 42:535-539; Schlegel et al. (2011) *Best Pract. Res. Clin. Haematol.* 24:443-452). In one study, the median age of patients was 11 years (range 4-16 years) and the duration of therapy ranged from 15 to 250 days (Schlegel et al. (2011) *Best Pract. Res. Clin. Haematol.* 24:443-452). Similarly, a dose escalation study in patients with neuroblastoma gave SC IL-2 at doses of 3, 6, and 9×10$^6$ IU/m$^2$/d in six 5-day cycles every 2 weeks to augment NK cell numbers (Ladenstein et al. (2011) *J. Clin. Oncol.* 29:441-448). The median age of patients in this study was 4.1 years (range 1.8-7.4 years). In all 3 studies, the major adverse effects were fevers and local inflammation at the injection sites.

The term "IL-2 immunotherapy" or "IL-2 therapy" includes administration of IL-2 to a subject in need thereof via any known route, such as intravenous administration, e.g., as a bolus or by continuous infusion over a period of time, by intramuscular, intraperitoneal, intracerobrospinal, subcutaneous, intra-articular, intrasynovial, intrathecal, oral, topical, inhalation, and other known routes. In general, the pharmacokinetics of IL-2 appear to be linear across humans, mice, rats, rabbits, sheep, pigs, and cynomolgus monkeys. After subcutaneous administration, absorption of IL-2 was relatively slow and the mean resident time was prolonged compared with IV administration.

IL-2 administration by the subcutaneous (SC) route has been evaluated in several multiple-dose studies in rats for up to 13 weeks of daily administration. They confirmed that the SC high-dose toxicity profile in rats was comparable to the high-dose toxicity profile after IV administration. IL-2-related findings included lymphocytosis, eosinophilia, slight anemia, extramedullary hematopoiesis, lymphoid hyperplasia, hepatomegaly and splenomegaly. Infiltrative and proliferative changes were seen in many organs, including liver, lung, lymph nodes, kidney, spleen and bone marrow. In rabbit, SC tolerability studies, after 7 days of dosing, local inflammatory responses at the injection site were consistent with the known effects of IL-2 and with injection-site reactions reported in human trials.

Thus, the toxicity of IL-2 in animals has been shown to be dose- and duration-related, with all toxic effects being directly or secondarily related to IL-2 pharmacological activity. In all species, treatment-related effects were fully or partially reversible after a treatment-free period of 2-4 weeks. Findings were comparable after repeated IV or SC administration of IL-2. The severity of target organ toxicity has been correlated with the extent of inflammatory cell infiltration into these organs. Biological effects in animals were generally similar to effects reported in clinical trials. However, these MTD studies relate to the high-dose IL-2 used for treatment of metastatic RCC and melanoma, rather than the low-dose IL-2 proposed for in vivo Treg enhancement.

IL-2 pharmacokinetics has been evaluated in patients with cancer and with HIV. Following a short IV infusion, the pharmacokinetic profile of IL-2 was characterized by high plasma concentrations, rapid distribution into the extravascular space, and elimination from the body with a half-life of 1-2 hours. After SC administration absorption of IL-2 was slow and the mean resident time was prolonged compared with IV administration. Maximum plasma concentration of IL-2 in HIV patients was achieved within 2-5 hours after SC dosing and the terminal phase half-life was estimated at 5 hours, suggesting prolonged absorption.

The clearance rates for bolus infusion and continuous IV infusions are approximately equal. As expected from its short half-life, steady state is expected to be reached approximately 6 hours after infusion. Data on SC IL-2 administration suggest that approximately 35% is absorbed into the bloodstream, with greater bioavailability (>60%) reported in a study involving HIV-infected participants. Five days of treatment by either SC or continuous IV administration in cancer or HIV patients resulted in a time-dependent increase in IL-2 clearance. This was associated with an increase in serum levels of soluble IL-2 receptor. Drug-free days between dosing cycles restored clearance of IL-2 to its initial value.

There are at least 3 mechanisms for the systemic removal of IL-2: glomerular filtration, peritubular extraction, and an inducible receptor-mediated mechanism (in man). Peritubular extraction of small peptides and proteins from the postglomerular capillaries into the renal tubules and subsequent intracellular catabolism is a renal mechanism of elimination that occurs independent of glomerular filtration. Receptor-mediated clearance is primarily a function of IL-2 engaging its specific cellular receptor on responsive cells. The majority of IL-2 receptors are on T cells, and natural killer (NK) cells, though other cell types such as B cells have functional IL-2 receptors.

In metastatic melanoma or renal cell cancer treated with high-dose bolus IL-2, nearly 6 fold increase in CD4+CD25+ Treg cells was observed, with 4 fold increase in the frequency of circulating CD4+FOXP3+ Treg cells (Ahmadzadeh and Rosenberg (2006) *Blood* 107:2409-2414). Considerable clinical data on the effects of IL-2 in patients with metastatic cancer have been accumulated over the past two decades. At the high doses of IL-2 used in most cancer trials, considerable toxicity has been documented, with only occasional tumor responses. Fever, hypotension, jaundice, and azotemia have been frequent complications, often necessitating admission to intensive care units. Hematopoietic stem cell transplantation (HSCT) patients are unlikely to tolerate high-dose IL-2.

Low-dose SC IL-2 for extended periods has been evaluated in patients with HIV infection and cancer. In one study of 'ultra-low-dose' IL-2, seven patients with HIV and Non-Hodgkin's Lymphoma in first remission received 1×10$^6$ IU/m$^2$/d of IL-2 (Chiron) (Shah et al. (2006) *Clin. Cancer Res.* 12:3993-3996). After ~8 weeks of treatment, single-agent IL-2 therapy led to statistically significant, proportional increases in NK cells (1.6-fold) and Tregs (9-fold). Other lymphocyte subsets were not significantly changed. Toxicity was mild (fatigue, local pruritus, myalgia, increased transaminases etc.), with no Grade 3 adverse events.

Low-dose IL-2 has also been used after allogeneic HSCT. In one study, IL-2 (Amgen, Roche) was administered by continuous IV infusion for periods of up to 3 months to 29 asymptomatic hematologic malignancy patients after CD6+ T-cell depleted (TCD) transplants at doses ranging from 2-6×10$^5$ IU/m$^2$/d, (≈0.6–1.8×10$^6$ U/m$^2$/d of IL-2 (Chiron)) in order to enhance immunologic graft-versus-leukemia (GVL) effects (Soiffer et al. (1994) *Blood* 84:964-971). Low-dose IL-2 was well tolerated with only 4 participants withdrawn early due to toxicity. Acute GVHD developed in only 1 of the 29 participants. In addition to the anticipated NK cell expansion, in 7 of 8 evaluated, a 45% median increase in CD4+CD25+ T lymphocytes occurred, likely representing Treg. Further, a median~8.5 fold increase of FOXP3 expression was noted, indicating substantial Treg enhancement (Zorn et al. (2006) *Blood* 108:1571-1579).

Low-dose IL-2 appeared well tolerated with significant Treg expansion post allogeneic HSCT.

Non-limiting examples of IL-2 immunotherapy are well known in the art and can be found, for example, at least in Rosenberg et al. (1993) *J. Natl. Cancer Inst.* 85:622-632; Guirguis et al. (2002) *J. Immunother.* 25:82-87; Griffiths and Mellon (2004) *Postgrad Med. J.* 80:320-327; Yang et al. (2003) *J. Clin. Oncol.* 21:3127-2132; McDermott et al. (2005) *J. Clin. Oncol.* 23:133-141; Negrier et al. (2007) *Cancer* 110:2468-2477; McDermott (2009) *Med. Oncol.* 26:13-17; U.S. Pat. Nos. 5,419,900, 5,696,079, 6,045,788, and 6,548,055, each of which is herein incorporated by reference in their entirety for all purposes.

III. Subjects

In one embodiment, the subject for whom anti-immune disorder treatment is administered or who is predicted to efficaciously respond to anti-immune disorder therapy (e.g., multiple-variable dose IL-2 alone or in combination with one or more other anti-immune disorder therapies) is determined, is a mammal (e.g., mouse, rat, primate, non-human mammal, domestic animal such as dog, cat, cow, horse), and is preferably a human. Adult subjects, as well as pediatric subjects, are contemplated. Pediatric subjects can be treated as described herein, as well as using doses of therapeutic agents up to those used for adult subjects.

In another embodiment of the methods of the present invention, the subject has not undergone treatment, such as anti-immune disorder therapy (e.g., multiple-variable dose IL-2 alone or in combination with one or more other anti-immune disorder therapies). In still another embodiment, the subject has undergone such treatment, such as with steroids.

The methods of the present invention can be used to treat and/or determine the responsiveness to anti-immune disorder therapy (e.g., multiple-variable dose IL-2 alone or in combination with one or more other anti-immune disorder therapies) of many different immune disorders in which suppressing or otherwise downregulating immune responses is desired. The functions of activated immune cells can be inhibited by down-regulating immune cell responses, by inducing specific anergy in immune cells, or both.

For example, the methods of the present invention can be used to induce tolerance against specific antigens by co-administering an antigen with the therapeutic compositions of such methods. Tolerance can be induced to specific proteins. In one embodiment, immune responses to allergens (e.g., food allergens), or to foreign proteins to which an immune response is undesirable, can be inhibited. For example, patients that receive Factor VIII frequently generate antibodies against this clotting factor. Co-administration of recombinant factor VIII (or by physically linked to Factor VIII, e.g., by cross-linking) in the methods of the present invention can result in downmodulation of immune responses. In similar manners, reduced clonal deletion and/ or increased exhaustion (e.g., T cell exhaustion) can be induced.

Downregulating immune responses is useful for treating a number of other "immune disorders" according to the present invention including, without limitation, situations of tissue, skin and other solid organ transplantation (e.g., kidney, liver, heart, and vascularized composite allotransplantation transplants), in hematopoietic stem cell transplantation rejection (e.g., graft-versus-host disease (GVHD)), in autoimmune diseases such as systemic lupus erythematosus, multiple sclerosis, allergy, a transplant, hypersensitivity response, in a disorder requiring increased CD4+ T cell production or function, in a disorder requiring improved vaccination efficiency, and in a disorder requiring increased regulatory T cell production or function. For example, blockage of immune cell function results in reduced tissue destruction in tissue transplantation. Typically, in tissue transplants, rejection of the transplant is initiated through its recognition as foreign by immune cells, followed by an immune reaction that destroys the transplant. The administration of an agent described herein prior to or at the time of transplantation can promote the generation of an inhibitory signal. Moreover, inhibition may also be sufficient to anergize the immune cells, thereby inducing tolerance in a subject. Induction of long-term tolerance avoids the necessity of repeated administration of these blocking reagents.

Downmodulation of immune responses are also useful in treating autoimmune disease, such as type 1 diabetes (T1D) and multiple sclerosis. Many autoimmune disorders are the result of inappropriate activation of immune cells that are reactive against self-tissue and which promote the production of cytokines and autoantibodies involved in the pathology of the diseases. Preventing the activation of autoreactive immune cells may reduce or eliminate disease symptoms. Administration of agents described herein are useful for preventing the generating of autoantibodies or cytokines which may be involved in the disease process. Additionally, the methods of the present invention can induce antigen-specific tolerance of autoreactive immune cells, which could lead to long-term relief from the disease. The efficacy of reagents in preventing or alleviating autoimmune disorders can be determined using a number of well-characterized animal models of human autoimmune diseases. Examples include murine experimental autoimmune encephalitis, systemic lupus erythematosus in MRL/lpr/lpr mice or NZB hybrid mice, murine autoimmune collagen arthritis, diabetes mellitus in NOD mice and BB rats, and murine experimental myasthenia gravis (see, e.g., Paul ed., Fundamental Immunology, Raven Press, New York, Third Edition 1993, chapter 30).

Inhibition of immune cell activation is also useful therapeutically in the treatment of allergy and allergic reactions, e.g., by inhibiting IgE production. Allergic reactions can be systemic or local in nature, depending on the route of entry of the allergen and the pattern of deposition of IgE on mast cells or basophils. Thus, inhibition of immune cell mediated allergic responses (e.g., to food) locally or systemically according to the methods of the present invention. In one embodiment, the allergy is allergic asthma.

Inhibition of immune cell activation may also be important therapeutically in parasitic and viral infections of immune cells. For example, in the acquired immune deficiency syndrome (AIDS), viral replication is stimulated by immune cell activation. Modulation of these interactions may result in inhibition of viral replication and thereby ameliorate the course of AIDS. Modulation of these interactions may also be useful in promoting the maintenance of pregnancy. Females at risk for spontaneous abortion (e.g., those who have previously had a spontaneous abortion or those who have had difficulty conceiving) because of immunologic rejection of the embryo or fetus can be treated with agents that modulate these interactions.

Downregulation of an immune response according to the methods of the present invention may also be useful in treating an autoimmune attack of autologous tissues. It is therefore within the scope of the invention to modulate conditions exacerbated by autoimmune attack, such as autoimmune disorders, as well as conditions such as heart disease, myocardial infarction, and atherosclerosis.

In a preferred embodiment, the immune disorder is graft-versus-host-disease (e.g., chronic GVHD). For many patients with hematologic malignancies, allogeneic hematopoietic stem cell transplant (HSCT) offers the only opportunity for cure. Unfortunately, significant obstacles remain, most notably disease recurrence and GVHD. Over 40% of patients undergoing HSCT relapse while more than 50% will develop cGVHD, a debilitating condition with multi-system immune manifestations associated with a considerable morbidity and mortality (Kahl et al. (2007) *Blood* 110:2744-2748; Perez-Simon et al. (2008) *Biol. Blood Marrow Transplant.* 14:1163-1171). Although the incidence in the pediatric population is lower, cGVHD remains a leading cause of non-relapse morbidity and mortality following allogeneic HSCT for malignant disease, occurring in 20 to 50% of children surviving greater than 100 days post-HSCT (Baird et al. (2010) *Pediatr. Clin. North Am.* 57:297-322). Donor cell-mediated immune responses are responsible for GVL and GVHD reactions. Inadequate recognition and destruction of residual tumor cells by a newly engrafted donor immune system permits recurrence of a patient's malignancy, while uncontrolled reactions against host antigens lead to GVHD (Antin (1993) *Blood* 82:2273-2277; Ferrara et al. (2009) *Lancet* 373:1550-1561). Chronic GVHD pathogenesis involves inflammatory T- and B-cell responses to allogeneic (donor/recipient polymorphic) and autologous (donor/recipient non-polymorphic) antigens and it remains a common problem and major therapeutic challenge after allogeneic HSCT, and long-term survivors often experience impaired quality of life and increased late mortality (Subramaniam et al. (2007) *Leukemia* 21:853-859). The increasing use of mobilized peripheral blood progenitor cells rather than bone marrow as a source of stem cells for HCT has resulted in a clear increase in the incidence of cGVHD (Cutler et al. (2001) *J. Clin. Oncol.* 19:3685-3691; Lee et al. (2007) *Blood* 110:4576-4583). The incidence of cGVHD in pediatric patients is expected to rise as allogeneic HSCT is increasingly being performed for non-malignant indications such as sickle cell anemia, immunodeficiency and congenital metabolic diseases. In both adults and children, the inflammatory or fibrotic changes associated with cGVHD most commonly involve the skin, eyes, mouth, liver and respiratory tract.

Systemic steroids are routinely used to treat cGVHD, but have limited efficacy and considerable toxicity. The effects of prolonged steroid therapy on growth and bone density are particularly significant in children (*Canalis* et al. (2002) *J. Pediatr. Endocrinol. Metab.* 15:1341-1345). In children, the use of most salvage agents is extrapolated from the adult experience, and only a few therapies, including mycophenolate mofetil (MMF), extracorporeal photopheresis (ECP) and pentostatin, have been tested in pediatric trials (Bucca et al. (2000) *Bone Marrow Transplant* 25:1067-1071; Berger et al. (2007) *J. Pediatr. Hematol. Oncol.* 29:678-687; Jacobsohn et al. (2009) *Blood* 114:4354-4360). There is no established second-line therapy for cGVHD. Additional immunosuppressive agents are often utilized for steroid-refractory cGVHD, despite their limited efficacy. Thus, second line treatment options are limited and steroid-refractory cGVHD presents a major therapeutic challenge.

IV. Anti-Immune Disorder Therapies

The methods of the present invention (e.g., multiple-variable dose IL-2 alone or in combination with one or more other anti-immune disorder therapies) can be administered to a desired subject or once a subject is indicated as being a likely responder to such therapy. In another embodiment, the therapeutic methods of the present invention can be avoided if a subject is indicated as not being a likely responder to the therapy and an alternative treatment regimen, such as targeted and/or untargeted anti-immune therapies, can be administered.

In one embodiment, a multiple-variable IL-2 dose method of treating a subject afflicted with an immune disorder comprising a) administering to the subject an induction regimen comprising continuously administering to the subject interleukin-2 (IL-2) at a dose that increases the subject's plasma IL-2 level and increases the subject's ratio of regulatory T lymphocytes (Tregs) to conventional T lymphocytes (Tcons) (Tregs:Tcons); and b) subsequently administering to the subject at least one maintenance regimen comprising continuously administering to the subject an IL-2 maintenance dose that is higher than the induction regimen dose and that i) further increases the subject's plasma IL-2 level and ii) further increases the ratio of Tregs to Tcons, thereby treating the subject, is provided. In one embodiment, the level of plasma IL-2 resulting from the induction regimen is depleted below that of the prior peak plasma IL-2 level before the induction regimen. The IL-2 maintainence regimen can, in certain embodiments, increase the subject's plasma IL-2 level beyond the peak plasma IL-2 level induced by the induction regimen. The term "multiple-variable IL-2 dose method" refers to a therapeutic intervention comprising more than one IL-2 administration, wherein the more than one IL-2 administration uses more than one IL-2 dose. Such a method is contrasted from a "fixed" dosing method wherein a fixed amount of IL-2 is administered in a scheduled manner, such as daily.

The term "induction regimen" refers to the continuous administration of IL-2 at a dose that increases the subject's plasma IL-2 level and increases the subject's Tregs:Tcons ratio. In some embodiments, the regimen occurs until a peak level of plasma IL-2 is achieved. The subject's plasma IL-2 level and/or Tregs:Tcons ratio can be increased by at least 5%, 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, 200% or more relative to the baseline ratio prior to initiation of therapy. At certain doses and methods according to FDA-approved uses, Tcons are preferentially activated relative to Tregs such that the Tregs:Tcons ratio actually decreases. By contrast, the methods of the present invention increase the Tregs:Tcons ratio by using "low-dose IL-2" in a range determined herein to preferentially promote Tregs over Tcons and that are safe and efficacious in subjects having an immune disorder. The term "low-dose IL-2" refers to the dosage range wherein Tregs are preferentially enhanced relative to Tcons. In one embodiment, low-dose IL-2 refers to IL-2 doses that are less than or equal to 50% of the "high-dose IL-2" doses (e.g., 18 million IU per $m^2$ per day to 20 million IU per $m^2$ per day, or more) used for anti-cancer immunotherapy. The upper limit of "low-dose IL-2" can further be limited by treatement adverse events, such as fever, chills, asthenia, and fatigue. IL-2 is generally dosed according to an amount measured in international units (IU) administered in comparison to body surface area (BSA) per given time unit. BSA can be calculated by direct measurement or by any number of well-known methods (e.g., the Dubois & Dubois formula), such as those described in the Examples. Generally, IL-2 is administered according in terms of IU per $m^2$ of BSA per day. Exemplary low-dose IL-2 doses according to the methods of the present invention include, in terms of $10^6$ IU/m$^2$/day, any one of 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, and 3.0×$10^6$ IU/m$^2$/day, including any values in between and/or ranges in between. For example, an induction regimen dose can range between 0.3×$10^6$ IU/m$^2$/day and 3.0×$10^6$ IU/m$^2$/day with any value or range in between.

The term "continuous administration" refers to administration of IL-2 at regular intervals without any intermittent breaks in between. Thus, no interruptions in IL-2 occur. For example, the induction dose can be administered every day (e.g., once or more per day) during at least 1-14 consecutive days or any range in between (e.g., at least 4-7 consecutive days). As described herein, longer acting IL-2 agents and/or IL-2 agents administered by routes other than subcutaneous administration are contemplated. Intermittent intravenous administration of IL-2 described in the art results in short IL-2 half lives incompatible with increasing plasma IL-2 levels and increasing the Tregs:Tcons ratio according to the present invention. However, once-daily subcutaneous IL-2 dosing, continuous IV infusion, long-acting subcutaneous IL-2 formulations, and the like are contemplated for achieving a persistent steady state IL-2 level.

Plasma IL-2 levels and peak values thereof can be assessed either directly or indirectly. For example, IL-2 nucleic acids and protein levels and/or activity can be directly analyzed using well known methods and reagents in the art, such as by using nucleic acid probes, ELISA kits, IL-2 receptor activation assays, and the like (see, for example, Sigma-Aldrich human IL-2 ELISA kit RAB-0286 and U.S. Pat. Nos. 4,530,787, 4,569,790, 4,572,798, 4,604,377, 4,748,234, 4,853,332, 4,959,314, 5,464,939, RE33,653, 5,229,109, 5,419,900, 5,696,079, 6,045,788, 6,548,055, 7,514,073, and 7,569,215, each of which is herein incorporated by reference in their entirety for all purposes).

In another embodiment, plasma IL-2 levels and/or activity can be indirectly analyzed by analyzing IL-2 effects such as on Tregs proliferation, Tregs activity, Tregs apoptosis, and the like. Methods for determining Tregs proliferation, Tregs activity, and/or Tregs apoptosis are well known in the art and as exemplified in the Examples described herein. For example, biomarkers of Tregs and/or Tcons cell differentiation and/or activation can be analyzed, such as by analyzing the status of CD25, phosphorylated STAT5 (pSTAT5), FOXP3, KI67, TUNEL, and the like. Moreover, phenotypic analyses of lymphocyte subsets, functional assays of immunomodulation leading to reduced immune responses, plasma cytokines, and the like can be analyzed as described further herein.

In still another embodiment, plasma IL-2 levels and/or activity can be indirectly determined according to time after initiation of the induction regimen. For example, it has been determined herein that peak plasma IL-2 levels are reached within approximately 7 days after initiation of the induction regimen. In some embodiments of the present invention, plasma IL-2 levels, such as peak plasma IL-2 levels, are determined according to 1, 2, 3, 4, 5, 6, 7, 8, 9, 10, 11, 12, 13, 14, or more days after initiation of the induction regimen.

At any point after the induction regimen, such as after peak plasma IL-2 levels and/or activity, although preferably as close in time to peak plasma IL-2 levels and/or activity as possible, a maintenance regimen can be initiated. The term "maintenance regimen" refers to the continuous administration to the subject IL-2 at a dose that is higher than the induction regimen dose and that i) further increases the subject's plasma IL-2 level and ii) further increases the ratio of Tregs to Tcons. In one embodiment, the maintenance regimen begins at or after the point at which the level of plasma IL-2 resulting from the induction regimen is depleted below that of the prior peak plasma IL-2 level before the induction regimen. As described above, this can be measured in terms of days after initiation of the induction regimen, such as 1, 2, 3, 4, 5, 6, 7, 8, 9, 10, 11, 12, 13, 14, or more days after initiation of the induction regimen.

In order to increase the level of plasma IL-2, IL-2 is administered to the subject at a dose that is higher than the induction regimen dose. In one embodiment, in terms of $10^6$ IU/m$^2$/day, the dose is any one of 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, and 3.0×$10^6$ IU/m$^2$/day, including any values in between and/or range in between. For example, an induction regimen dose can range between 0.3×$10^6$ IU/m$^2$/day and 3.0×$10^6$ IU/m$^2$/day with any value or range in between. The maintenance regimen dose can be at least about 5%, 10%, 15%, 20%, 25%, 30%, 35%, 40%, 45%, 50%, 55%, 60%, 65%, 70%, 75%, 80%, 85%, 90%, 95%, 100%, or more, or any value in between and/or range in between. The increased level of plasma IL-2 also increases the Tregs:Tcons ratio relative to the induction regimen Tregs:Tcons, such as by increasing the ratio by at least about 5%, 10%, 15%, 20%, 25%, 30%, 35%, 40%, 45%, 50%, 55%, 60%, 65%, 70%, 75%, 80%, 85%, 90%, 95%, 100%, or more, or any value in between and/or range in between.

Consistent with the induction regimen, the term "continuous administration" refers to administration of IL-2 at regular intervals without any intermittent breaks in between. Thus, no interruptions in IL-2 occur. Although this can be achieved by using IL-2 administration protocols without intermittent breaks, IL-2 continuous administration can also be achieved by using IL-2 agents that provide steady-state plasma IL-2 levels. For example, the maintenance dose can be administered every day (e.g., once or more per day) on a long-term therapeutic basis, such as indefinitely. In some embodiments, the during at least 1-42 consecutive days or any range in between (e.g., at least 14-42 consecutive days).

As described above, IL-2 can be administered in a pharmaceutically acceptable formulation and by any suitable administration route, such as by subcutaneous, intravenous, intraperitoneal, oral, nasal, transdermal, or intramuscular administration. In one embodiment, the present invention provides pharmaceutically acceptable compositions which comprise IL-2 at a therapeutically-effective amount, formulated together with one or more pharmaceutically acceptable carriers (additives) and/or diluents. The pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "pharmaceutically acceptable" is employed herein to refer to those agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

IL-2 formulations suitable for in vivo administration are well known in the art (see, for example, U.S. Pat. Nos. 4,530,787, 4,569,790, 4,572,798, 4,604,377, 4,748,234, 4,853,332, 4,959,314, 5,464,939, RE33,653, 5,229,109, 5,419,900, 5,696,079, 6,045,788, 6,548,055, 7,514,073, and 7,569,215, each of which is herein incorporated by reference in their entirety for all purposes).

In some embodiments, IL-2 or other useful biomarker nucleic acid molecules are useful and can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054 3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

Any means for the introduction of a polynucleotide into mammals, human or non-human, or cells thereof may be adapted to the practice of this invention for the delivery of the various constructs of the invention into the intended recipient. In one embodiment of the invention, the DNA constructs are delivered to cells by transfection, i.e., by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system of this invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Felgner, et al., *Ann NY Acad Sci* 126-139, 1995). Formulation of DNA, e.g. with various lipid or liposome materials, may then be effected using known methods and materials and delivered to the recipient mammal. See, e.g., Canonico et al, *Am J Respir Cell Mol Biol* 10:24-29, 1994; Tsan et al, *Am J Physiol* 268; Alton et al., *Nat Genet.* 5:135-142, 1993 and U.S. Pat. No. 5,679,647 by Carson et al.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs, which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Naked DNA or DNA associated with a delivery vehicle, e.g., liposomes, can be administered to several sites in a subject (see below).

Nucleic acids can be delivered in any desired vector. These include viral or non-viral vectors, including adenovirus vectors, adeno-associated virus vectors, retrovirus vectors, lentivirus vectors, and plasmid vectors. Exemplary types of viruses include HSV (herpes simplex virus), AAV (adeno associated virus), HIV (human immunodeficiency virus), BIV (bovine immunodeficiency virus), and MLV (murine leukemia virus). Nucleic acids can be administered in any desired format that provides sufficiently efficient delivery levels, including in virus particles, in liposomes, in nanoparticles, and complexed to polymers.

The nucleic acids encoding a protein or nucleic acid of interest may be in a plasmid or viral vector, or other vector as is known in the art. Such vectors are well known and any can be selected for a particular application. In one embodiment of the invention, the gene delivery vehicle comprises a promoter and a demethylase coding sequence. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter. A promoter may be constitutive or inducible.

In another embodiment, naked polynucleotide molecules are used as gene delivery vehicles, as described in WO 90/11092 and U.S. Pat. No. 5,580,859. Such gene delivery vehicles can be either growth factor DNA or RNA and, in certain embodiments, are linked to killed adenovirus. Curiel et al., *Hum. Gene. Ther.* 3:147-154, 1992. Other vehicles which can optionally be used include DNA-ligand (Wu et al., *J. Biol. Chem.* 264:16985-16987, 1989), lipid-DNA combinations (Feigner et al., *Proc. Natl. Acad. Sci. USA* 84:7413 7417, 1989), liposomes (Wang et al., *Proc. Natl. Acad. Sci.* 84:7851-7855, 1987) and microprojectiles (Williams et al., *Proc. Natl. Acad. Sci.* 88:2726-2730, 1991).

A gene delivery vehicle can optionally comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the growth factor gene delivery vehicle is a recombinant retroviral vector. Recombinant retroviruses and various uses thereof have been described in numerous references including, for example, Mann et al., *Cell* 33:153, 1983, Cane and Mulligan, *Proc. Nat'l. Acad. Sci. USA* 81:6349, 1984, Miller et al., *Human Gene Therapy* 1:5-14, 1990, U.S. Pat. Nos. 4,405,712, 4,861,719, and 4,980,289, and PCT Application Nos. WO 89/02,468, WO 89/05,349, and WO 90/02,806. Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart, *Cancer Res.* 53:3860-3864, 1993; Vile and Hart, *Cancer Res.* 53:962-967, 1993; Ram et al., *Cancer Res.* 53:83-88, 1993; Takamiya et al., *J. Neurosci. Res.* 33:493-503, 1992; Baba et al., *J. Neurosurg.* 79:729-735, 1993 (U.S. Pat. No. 4,777,127, GB 2,200,651, EP 0,345,242 and WO91/02805).

Other viral vector systems that can be used to deliver a polynucleotide of the invention have been derived from herpes virus, e.g., Herpes Simplex Virus (U.S. Pat. No. 5,631,236 by Woo et al., issued May 20, 1997 and WO 00/08191 by Neurovex), vaccinia virus (Ridgeway (1988) Ridgeway, "Mammalian expression vectors," In: Rodriguez R L, Denhardt D T, ed. Vectors: A survey of molecular cloning vectors and their uses. Stoneham: Butterworth; Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) Gene, 68:1-10), and several RNA viruses. Preferred viruses include an alphavirus, a poxivirus, an arena virus, a vaccinia virus, a polio virus, and the like. They offer several attractive features for various mammalian cells (Friedmann (1989) Science, 244:1275-1281; Ridgeway, 1988, supra; Baichwal and Sugden, 1986, supra; Coupar et al., 1988; Horwich et al. (1990) J. Virol., 64:642-650).

In other embodiments, target DNA in the genome can be manipulated using well-known methods in the art. This can be useful for recombinantly engineering subject T cell populations ex vivo prior to infusion into the subject. For example, the target DNA in the genome can be manipulated by deletion, insertion, and/or mutation are retroviral insertion, artificial chromosome techniques, gene insertion, random insertion with tissue specific promoters, gene targeting, transposable elements and/or any other method for introducing foreign DNA or producing modified DNA/modified nuclear DNA. Other modification techniques include deleting DNA sequences from a genome and/or altering nuclear DNA sequences. Nuclear DNA sequences, for example, may be altered by site-directed mutagenesis.

In other embodiments, recombinant biomarker polypeptides, and fragments thereof, can be administered to subjects. In some embodiments, fusion proteins can be constructed and administered which have enhanced biological properties. In addition, the biomarker polypeptides, and fragment thereof, can be modified according to well-known pharmacological methods in the art (e.g., pegylation, glycosylation, oligomerization, etc.) in order to further enhance desirable biological activities, such as increased bioavailability and decreased proteolytic degradation.

In some aspects, multiple-variable dose IL-2 therapy can be combined with one or more other anti-immune disorder therapies.

In one embodiment, extracorporeal photopheresis (ECP) is useful. ECP is an apheresis procedure that consists of UVA irradiation of apheresis-collected, autologous leukocytes that are sensitized with 8-methoxypsoralen (8-MOP) and subsequently reinfused to increase Tregs (Gatza et al. (2008) *Blood* 112:1515-1521; Capitini et al. (2011) *Biol. Blood Marrow Transplant.* 17:790-799; Maeda et al. (2008) *J. Immunol.* 181:5956-5962) and induce immature and plasmacytoid dendritic cells (DCs) through apoptotic T cells before such Treg increases (Perez et al. (1991) *Transplantation* 51:1283-1289; Stenger et al. (2012) *Blood* 119:5088-5103; Albert et al. (1998) *Nature* 392:86-89; Yoo et al. (1996) *J. Invest. Dermatol.* 107:235-242). Human data on ECP mechanisms selectively report Tregs (Schmitt et al. (2009) *Transplantation* 88:411-416; Biagi et al. (2007) *Transplantation* 84:31-39) or DC phenotype (Shiue et al. (2013) *J. Invest. Dermatol.* 133:2098-2100), but in heterogeneous populations, often without inclusion criteria or pre-ECP baseline data. ECP is a routinely recommended and CMS-approved second-line treatment for cGVHD (Dignan et al. (2012) *Br. J. Haematol.* 158:62-78). Although safe in practice, ECP alone provides limited clinical benefit. Approximately half of treated patients do not have a clinical response; partial response is the norm for responders; and taper of immune suppressants during extended ECP is slow and often incomplete.

In another embodiment, regulatory T-cell infusion is useful. Infusion of Tregs has been well tolerated in the HSCT context. A trial in 23 double umbilical cord blood (DUCB) HSCT recipients evaluated the safety of infusing UCB Treg expanded ex vivo with IL-2. No IL-2 was administered in vivo. Patients received a dose of $0.1\text{-}30 \times 10^5$ Treg cells/kg after transplantation. No infusional toxicities were observed. Compared with identically treated 108 historical controls without UCB Treg infusion, there was a lower incidence of grade II-IV acute GVHD (43% vs. 61%, P=0.05) with no deleterious effect on infection, relapse, or early mortality (Brunstein et al. (2011) *Blood* 117:1061-1070). However, infused UCB Tregs could only be detected in vivo for 14 days. In another trial of 28 hematologic malignancy patients who underwent high-risk HLA-haploidentical HSCT, peri-transplant infusion of donor Treg-enriched cells, followed thereafter by Tcon infusion, prevented GVHD even in the absence of post-transplantation immunosuppression, promoted lymphoid reconstitution, improved immunity to opportunistic pathogens, and did not weaken the graft-versus-leukemia effect (Di Ianni et al. (2011) *Blood* 117:3921-3928). The study utilized 2-step donor Treg-cell enrichment via CLINIMACS® (cell processing platform) (Miltenyi Biotec) immunomagnetic bead separation: a) clinical-grade CD8+/CD19+co-depletion (2.1 depletion program, CLINIMACS® (cell processing platform)) followed by and b) CD25+ positive selection (3.1 enrichment program, CLINIMACS® (cell processing platform)). The Treg-enriched cell product was suppressive in vitro at a Treg:Tcon ratio of 1:2. No toxicity was reported after infusion of up to $4\times10^6$ Treg-enriched cells/kg, despite the subsequent infusion of up to $2\times10^6$ Tcon cells/kg (CLINIMACS® (cell processing platform) CD19+ depleted donor lymphocytes).

Unlike known methods of regulatory T-cell infusion involving cumbersome and expensive Treg expansion and purification procedures, it has been determined herein that direct collection and infusion of an HSCT donor or a subject's own Tregs without the need for expansion of the cells in a laboratory offers a simple, effective, and durable means to treat immune disorders. This effect occurs because the combination with low-dose IL-2 creates in vivo conditions for expanding the infused Tregs directly in the body in order to durably enhance Tregs in patients for a durable control of immune disorders.

The Tregs can be purified or can be enriched. "Enriched Tregs" refer to a composition comprising Tregs in addition to other T cells in a proportion where the composition has at least a 1:2, 1:1.9, 1:1.8, 1:1.7, 1:1.6, 1:1.5, 1:1.4, 1:1.3, 1:1.2, 1:1.1, 1:1, 1:0.9, 1:0.8, 1:0.7, 1:0.6, 1:0.5, 1:0.4, 1:0.3, 1:0.2, 1:0.1, or more, or any range in between or any value in between, ratio of Tregs to Tcons. Such ratios can be achieved by purifying a composition comprising T cells with CD8+ and CD19+co-depletion in combination with positive selection for CD25+ cells. The cell populations comprising enriched Tregs can be administered at $0.1\times10^6$, $0.2\times10^6$, $0.3\times10^6$, $0.4\times10^6$, $0.5\times10^6$, $0.6\times10^6$, $0.7\times10^6$, $0.8\times10^6$, $0.9\times10^6$, $1.0\times10^6$, or more, or any range in between or any value in between, cells per kilogram of subject body weight. Such enriched Tregs can further be defined in terms of cell markers and/or viability. For example, an enriched Tregs cell composition can have greater than 40%, 45%, 50%, 55%, 60%, 65%, 70%, 75%, 80%, 85%, 90%, 95%, 99%, or more, or any range in between or any value in between, total cell viability. It can have a negative gram stain. It can comprise greater than 40%, 45%, 50%, 55%, 60%, 65%, 70%, 75%, 80%, 85%, 90%, 95%, 99%, or more, or any range in between or any value in between, CD4+CD25+ cells. It can comprise greater than 40%, 45%, 50%, 55%, 60%, 65%, 70%, 75%, 80%, 85%, 90%, 95%, 99%, or more, or any range in between or any value in between, FoxP3+ cells. Tregs can be administered in any suitable route as described herein, such as by infusion. Tregs can also be administered before, concurrently with, or after, IL-2 administration.

In still another embodiment, treatment methods may further use agents that block an activity of costimulatory pathways, such as that of other B lymphocyte antigen like B7-1, B7-2, or B7-3) to further downmodulate immune responses. Two separate agents that downmodulate immune responses can be combined as a single composition or administered separately (simultaneously or sequentially) to more effectively downregulate immune cell mediated immune responses in a subject. Furthermore, a therapeutically active amount of one or more of the subject agents, can be used in conjunction with other downmodulating reagents to influence immune responses. Examples of other immunomodulating reagents include, without limitation, antibodies that block a costimulatory signal, (e.g., against CD28 or ICOS), antibodies that act as agonists of CTLA4, and/or antibodies against other immune cell markers (e.g., against CD40, against CD40 ligand, or against cytokines), fusion proteins (e.g., CTLA4-Fc), and immunosuppressive drugs, (e.g., rapamycin, cyclosporine A or FK506).

Moreover, agents that promote the activity of immune checkpoint proteins are useful. The term "immune checkpoint protein" refers to a group of molecules on the cell surface of CD4+ and/or CD8+ T cells that fine-tune immune responses by downmodulating or inhibiting an anti-tumor immune response. Immune checkpoint proteins are well known in the art and include, without limitation, CTLA-4 as described above, as well as PD-1, VISTA, B7-H2, B7-H3, PD-L1, B7-H4, B7-H6, 2B4, ICOS, HVEM, PD-L2, CD160, gp49B, PIR-B, KIR family receptors, TIM-1, TIM-3, TIM-4, LAG-3, BTLA, SIRPalpha (CD47), CD48, 2B4 (CD244), B7.1, B7.2, ILT-2, ILT-4, TIGIT, and A2aR (see, for example, WO 2012/177624). Agents useful for promoting immune checkpoint protein levels and activity are well known in the art.

In yet another embodiment, any first- or second-line immune disorder treatment can be combined with the methods of the present invention. Representative examples include, but are not limited to, steroidal, mycophenolate mofetil (MMF), and pentostatin (see, for example, Busca et al. (2000) *Bone Marrow Transplant* 25:1067-1071; Berger et al. (2007) *J. Pediatr. Hematol. Oncol.* 29:678-687; Jacobsohn et al. (2009) *Blood* 114:4354-4360).

V. Clinical Efficacy

Clinical efficacy can be measured by any method known in the art. For example, response may be recorded in a quantitative fashion like percentage change in affected area or using a semi-quantitativ in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of tumor response may be performed at any time after the onset of therapy, e.g., after a few hours, days, weeks or preferably after a few months.

In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular therapeutic regimen is at least 25%, 30%, 35%, 40%, 45%, 50%, 55%, 60%, 65%, 70%, 75%, 80%, 85%, or more.

Additional criteria for evaluating a response are related to "survival," which includes all of the following: survival until mortality, also known as overall survival (wherein said mortality may be either irrespective of cause); "recurrence-free survival" (wherein the term recurrence shall include both localized and distant recurrence); disease free survival (wherein the term disease shall include immune disorders and diseases associated therewith). The length of said survival may be calculated by reference to a defined start point (e.g., time of diagnosis or start of treatment) and end point (e.g., death or recurrence).

For example, in order to determine appropriate threshold values, a particular therapeutic regimen can be administered to a population of subjects and the outcome can be correlated to biomarker measurements that were determined prior to administration of any therapy. The outcome measurement may be pathologic response to therapy given in the neoadjuvant setting. Alternatively, outcome measures, such as overall survival and disease-free survival can be monitored over a period of time for subjects following anti-immune disorder therapy for whom biomarker measurement values are known. In certain embodiments, the same doses of active agents are administered to each subject. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Biomarker measurement threshold values that correlate to outcome of an anti-immune disorder therapy can be determined using methods such as those described in the Examples section.

V. Further Methods of the Present Invention

Biomarker nucleic acids and/or biomarker polypeptides can be analyzed according to the methods described herein and techniques known to the skilled artisan to identify such genetic or expression alterations useful for diagnostic and prognostic purposes. For example, biomarkers identifying Tregs and/or Tcons can be detected, as well as cellular biomarkers of activity thereof. Such methods include, but are not limited to, 1) an alteration in the level of a biomarker transcript or polypeptide, 2) a deletion or addition of one or more nucleotides from a biomarker gene, 4) a substitution of one or more nucleotides of a biomarker gene, 5) aberrant modification of a biomarker gene, such as an expression regulatory region, and the like.

a. Sample Collection, Preparation and Separation

In some embodiments, biomarker presence, absence, amount, and/or activity measurement(s) in a sample from a subject is compared to a predetermined control (standard) sample. The sample from the subject is typically from a diseased tissue, such as immune disorder cells or tissues. The control sample can be from the same subject or from a different subject. The control sample is typically a normal, non-diseased sample. However, in some embodiments, such as for staging of disease or for evaluating the efficacy of treatment, the control sample can be from a diseased tissue. The control sample can be a combination of samples from several different subjects. In some embodiments, the biomarker amount and/or activity measurement(s) from a subject is compared to a pre-determined level. This pre-determined level is typically obtained from normal samples, such as the normal copy number, amount, or activity of a biomarker in the cell or tissue type of a member of the same species as from which the test sample was obtained or a non-diseased cell or tissue from the subject from which the test samples was obtained. As described herein, a "predetermined" biomarker amount and/or activity measurement(s) may be a biomarker amount and/or activity measurement(s) used to, by way of example only, evaluate a subject that may be selected for treatment, evaluate a response to an anti-immune disorder therapy (e.g., multiple-variable dose IL-2 therapy alone or in combination with one or more other anti-immune disorder therapies). A pre-determined biomarker amount and/or activity measurement(s) may be determined in populations of patients with or without an immune disorder. The pre-determined biomarker amount and/or activity measurement(s) can be a single number, equally applicable to every patient, or the pre-determined biomarker amount and/or activity measurement(s) can vary according to specific subpopulations of patients. Age, weight, height, and other factors of a subject may affect the pre-determined biomarker amount and/or activity measurement(s) of the individual. Furthermore, the pre-determined biomarker amount and/or activity can be determined for each subject individually. In one embodiment, the amounts determined and/or compared in a method described herein are based on absolute measurements. In another embodiment, the amounts determined and/or compared in a method described herein are based on relative measurements, such as ratios (e.g., biomarker expression normalized to the expression of a housekeeping gene, or gene expression at various time points).

The pre-determined biomarker amount and/or activity measurement(s) can be any suitable standard. For example, the pre-determined biomarker amount and/or activity measurement(s) can be obtained from the same or a different human for whom a patient selection is being assessed. In one embodiment, the pre-determined biomarker amount and/or activity measurement(s) can be obtained from a previous assessment of the same patient. In such a manner, the progress of the selection of the patient can be monitored over time. In addition, the control can be obtained from an assessment of another human or multiple humans, e.g., selected groups of humans, if the subject is a human. In such a manner, the extent of the selection of the human for whom selection is being assessed can be compared to suitable other humans, e.g., other humans who are in a similar situation to the human of interest, such as those suffering from similar or the same condition(s) and/or of the same ethnic group.

In some embodiments of the present invention the change of biomarker amount and/or activity measurement(s) and/or ratio from the pre-determined level is about 0.5 fold, about 1.0 fold, about 1.5 fold, about 2.0 fold, about 2.5 fold, about 3.0 fold, about 3.5 fold, about 4.0 fold, about 4.5 fold, or about 5.0 fold or greater. In some embodiments, the fold change is less than about 1, less than about 5, less than about 10, less than about 20, less than about 30, less than about 40, or less than about 50. In other embodiments, the fold change in biomarker amount and/or activity measurement(s) compared to a predetermined level is more than about 1, more than about 5, more than about 10, more than about 20, more than about 30, more than about 40, or more than about 50.

Biological samples can be collected from a variety of sources from a patient including a body fluid sample, cell sample, or a tissue sample comprising nucleic acids and/or proteins. "Body fluids" refer to fluids that are excreted or secreted from the body as well as fluids that are normally not (e.g., amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit). In a preferred embodiment, the subject and/or control sample is selected from the group consisting of cells, cell lines, histological slides, paraffin embedded tissues, biopsies, whole blood, nipple aspirate, serum, plasma, buccal scrape, saliva, cerebrospinal fluid, urine, stool, and bone marrow. In one embodiment, the sample is serum, plasma, or urine. In another embodiment, the sample is serum. In still other embodiments, biological samples comprising T lymphocytes are useful including, but not limited to, whole blood, purified blood, spleen tissue, lymph fluid, lymph node tissue, and the like.

The samples can be collected from individuals repeatedly over a longitudinal period of time (e.g., once or more on the order of days, weeks, months, annually, biannually, etc.). Obtaining numerous samples from an individual over a period of time can be used to verify results from earlier detections and/or to identify an alteration in biological pattern as a result of, for example, disease progression, drug treatment, etc. For example, subject samples can be taken and monitored every month, every two months, or combinations of one, two, or three month intervals according to the invention. In addition, the biomarker amount and/or activity measurements of the subject obtained over time can be conveniently compared with each other, as well as with those of normal controls during the monitoring period, thereby providing the subject's own values, as an internal, or personal, control for long-term monitoring.

Sample preparation and separation can involve any of the procedures, depending on the type of sample collected and/or analysis of biomarker measurement(s). Such procedures include, by way of example only, concentration, dilution, adjustment of pH, removal of high abundance polypeptides (e.g., albumin, gamma globulin, and transferrin, etc.), addition of preservatives and calibrants, addition of protease inhibitors, addition of denaturants, desalting of samples, concentration of sample proteins, extraction and purification of lipids.

The sample preparation can also isolate molecules that are bound in non-covalent complexes to other protein (e.g., carrier proteins). This process may isolate those molecules bound to a specific carrier protein (e.g., albumin), or use a more general process, such as the release of bound molecules from all carrier proteins via protein denaturation, for example using an acid, followed by removal of the carrier proteins.

Removal of undesired proteins (e.g., high abundance, uninformative, or undetectable proteins) from a sample can be achieved using high affinity reagents, high molecular weight filters, ultracentrifugation and/or electrodialysis. High affinity reagents include antibodies or other reagents (e.g., aptamers) that selectively bind to high abundance proteins. Sample preparation could also include ion exchange chromatography, metal ion affinity chromatography, gel filtration, hydrophobic chromatography, chromatofocusing, adsorption chromatography, isoelectric focusing and related techniques. Molecular weight filters include membranes that separate molecules on the basis of size and molecular weight. Such filters may further employ reverse osmosis, nanofiltration, ultrafiltration and microfiltration.

Ultracentrifugation is a method for removing undesired polypeptides from a sample. Ultracentrifugation is the centrifugation of a sample at about 15,000-60,000 rpm while monitoring with an optical system the sedimentation (or lack thereof) of particles. Electrodialysis is a procedure which uses an electromembrane or semipermeable membrane in a process in which ions are transported through semi-permeable membranes from one solution to another under the influence of a potential gradient. Since the membranes used in electrodialysis may have the ability to selectively transport ions having positive or negative charge, reject ions of the opposite charge, or to allow species to migrate through a semipermable membrane based on size and charge, it renders electrodialysis useful for concentration, removal, or separation of electrolytes.

Separation and purification in the present invention may include any procedure known in the art, such as capillary electrophoresis (e.g., in capillary or on-chip) or chromatography (e.g., in capillary, column or on a chip). Electrophoresis is a method which can be used to separate ionic molecules under the influence of an electric field. Electrophoresis can be conducted in a gel, capillary, or in a microchannel on a chip. Examples of gels used for electrophoresis include starch, acrylamide, polyethylene oxides, agarose, or combinations thereof. A gel can be modified by its cross-linking, addition of detergents, or denaturants, immobilization of enzymes or antibodies (affinity electrophoresis) or substrates (zymography) and incorporation of a pH gradient. Examples of capillaries used for electrophoresis include capillaries that interface with an electrospray.

Capillary electrophoresis (CE) is preferred for separating complex hydrophilic molecules and highly charged solutes. CE technology can also be implemented on microfluidic chips. Depending on the types of capillary and buffers used, CE can be further segmented into separation techniques such as capillary zone electrophoresis (CZE), capillary isoelectric focusing (LIEF), capillary isotachophoresis (cITP) and capillary electrochromatography (CEC). An embodiment to couple CE techniques to electrospray ionization involves the use of volatile solutions, for example, aqueous mixtures containing a volatile acid and/or base and an organic such as an alcohol or acetonitrile.

Capillary isotachophoresis (cITP) is a technique in which the analytes move through the capillary at a constant speed but are nevertheless separated by their respective mobilities. Capillary zone electrophoresis (CZE), also known as free-solution CE (FSCE), is based on differences in the electrophoretic mobility of the species, determined by the charge on the molecule, and the frictional resistance the molecule encounters during migration which is often directly proportional to the size of the molecule. Capillary isoelectric focusing (CIEF) allows weakly-ionizable amphoteric molecules, to be separated by electrophoresis in a pH gradient. CEC is a hybrid technique between traditional high performance liquid chromatography (HPLC) and CE.

Separation and purification techniques used in the present invention include any chromatography procedures known in the art. Chromatography can be based on the differential adsorption and elution of certain analytes or partitioning of analytes between mobile and stationary phases. Different examples of chromatography include, but not limited to, liquid chromatography (LC), gas chromatography (GC), high performance liquid chromatography (HPLC), etc.

b. Methods for Detection of Copy Number and/or Genomic Nucleic Acid Mutations

Methods of evaluating the copy number and/or genomic nucleic acid status (e.g., mutations) of a biomarker nucleic acid are well known to those of skill in the art. The presence or absence of chromosomal gain or loss can be evaluated simply by a determination of copy number of the regions or markers identified herein.

In one embodiment, a biological sample is tested for the presence of copy number changes in genomic loci containing the genomic marker.

Methods of evaluating the copy number of a biomarker locus include, but are not limited to, hybridization-based assays. Hybridization-based assays include, but are not limited to, traditional "direct probe" methods, such as Southern blots, in situ hybridization (e.g., FISH and FISH plus SKY) methods, and "comparative probe" methods, such as comparative genomic hybridization (CGH), e.g., cDNA-based or oligonucleotide-based CGH. The methods can be used in a wide variety of formats including, but not limited to, substrate (e.g. membrane or glass) bound methods or array-based approaches.

In one embodiment, evaluating the biomarker gene copy number in a sample involves a Southern Blot. In a Southern Blot, the genomic DNA (typically fragmented and separated on an electrophoretic gel) is hybridized to a probe specific for the target region. Comparison of the intensity of the hybridization signal from the probe for the target region with control probe signal from analysis of normal genomic DNA (e.g., a non-amplified portion of the same or related cell, tissue, organ, etc.) provides an estimate of the relative copy number of the target nucleic acid. Alternatively, a Northern blot may be utilized for evaluating the copy number of encoding nucleic acid in a sample. In a Northern blot, mRNA is hybridized to a probe specific for the target region. Comparison of the intensity of the hybridization signal from the probe for the target region with control probe signal from analysis of normal RNA (e.g., a non-amplified portion of the same or related cell, tissue, organ, etc.) provides an estimate of the relative copy number of the target nucleic acid. Alternatively, other methods well known in the art to detect RNA can be used, such that higher or lower expression relative to an appropriate control (e.g., a non-amplified portion of the same or related cell tissue, organ, etc.) provides an estimate of the relative copy number of the target nucleic acid.

An alternative means for determining genomic copy number is in situ hybridization (e.g., Angerer (1987) *Meth. Enzymol* 152: 649). Generally, in situ hybridization comprises the following steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application. In a typical in situ hybridization assay, cells are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained. The probes are typically labeled, e.g., with radioisotopes or fluorescent reporters. In one embodiment, probes are sufficiently long so as to specifically hybridize with the target nucleic acid(s) under stringent conditions. Probes generally range in length from about 200 bases to about 1000 bases. In some applications it is necessary to block the hybridization capacity of repetitive sequences. Thus, in some embodiments, tRNA, human genomic DNA, or Cot-I DNA is used to block non-specific hybridization.

An alternative means for determining genomic copy number is comparative genomic hybridization. In general, genomic DNA is isolated from normal reference cells, as well as from test cells (e.g., tumor cells) and amplified, if necessary. The two nucleic acids are differentially labeled and then hybridized in situ to metaphase chromosomes of a reference cell. The repetitive sequences in both the reference and test DNAs are either removed or their hybridization capacity is reduced by some means, for example by prehybridization with appropriate blocking nucleic acids and/or including such blocking nucleic acid sequences for said repetitive sequences during said hybridization. The bound, labeled DNA sequences are then rendered in a visualizable form, if necessary. Chromosomal regions in the test cells which are at increased or decreased copy number can be identified by detecting regions where the ratio of signal from the two DNAs is altered. For example, those regions that have decreased in copy number in the test cells will show relatively lower signal from the test DNA than the reference compared to other regions of the genome. Regions that have been increased in copy number in the test cells will show relatively higher signal from the test DNA. Where there are chromosomal deletions or multiplications, differences in the ratio of the signals from the two labels will be detected and the ratio will provide a measure of the copy number. In another embodiment of CGH, array CGH (aCGH), the immobilized chromosome element is replaced with a collection of solid support bound target nucleic acids on an array, allowing for a large or complete percentage of the genome to be represented in the collection of solid support bound targets. Target nucleic acids may comprise cDNAs, genomic DNAs, oligonucleotides (e.g., to detect single nucleotide polymorphisms) and the like. Array-based CGH may also be performed with single-color labeling (as opposed to labeling the control and the possible tumor sample with two different dyes and mixing them prior to hybridization, which will yield a ratio due to competitive hybridization of probes on the arrays). In single color CGH, the control is labeled and hybridized to one array and absolute signals are read, and the possible tumor sample is labeled and hybridized to a second array (with identical content) and absolute signals are read. Copy number difference is calculated based on absolute signals from the two arrays. Methods of preparing immobilized chromosomes or arrays and performing comparative genomic hybridization are well known in the art (see, e.g., U.S. Pat. Nos. 6,335,167; 6,197,501; 5,830,645; and 5,665,549 and Albertson (1984) *EMBO J.* 3: 1227-1234; Pinkel (1988) *Proc. Natl. Acad. Sci. USA* 85: 9138-9142; EPO Pub. No. 430,402; *Methods in Molecular Biology*, Vol. 33: In situ Hybridization Protocols, Choo, ed., Humana Press, Totowa, N.J. (1994), etc.) In another embodiment, the hybridization protocol of Pinkel, et al. (1998) *Nature Genetics* 20: 207-211, or of Kallioniemi (1992) *Proc. Natl Acad Sci USA* 89:5321-5325 (1992) is used.

In still another embodiment, amplification-based assays can be used to measure copy number. In such amplification-based assays, the nucleic acid sequences act as a template in an amplification reaction (e.g., Polymerase Chain Reaction (PCR)). In a quantitative amplification, the amount of amplification product will be proportional to the amount of template in the original sample. Comparison to appropriate controls, e.g. healthy tissue, provides a measure of the copy number.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis, et al. (1990) PCR Protocols, *A Guide to Methods and Applications*, Academic Press, Inc. N.Y.). Measurement of DNA copy number at microsatellite loci using quantitative PCR analysis is described in Ginzonger, et al. (2000) *Cancer Research* 60:5405-5409. The known nucleic acid sequence for the genes is sufficient to enable one of skill in the art to routinely select primers to amplify any portion of the gene. Fluorogenic quantitative PCR may also be used in the methods of the invention. In fluorogenic quantitative PCR, quantitation is based on amount of fluorescence signals, e.g., TaqMan and SYBR green.

Other suitable amplification methods include, but are not limited to, ligase chain reaction (LCR) (see Wu and Wallace (1989) *Genomics* 4: 560, Landegren, et al. (1988) *Science* 241:1077, and Barringer et al. (1990) *Gene* 89: 117), transcription amplification (Kwoh, et al. (1989) *Proc. Natl. Acad. Sci. USA* 86: 1173), self-sustained sequence replication (Guatelli, et al. (1990) *Proc. Nat. Acad. Sci. USA* 87: 1874), dot PCR, and linker adapter PCR, etc.

Loss of heterozygosity (LOH) and major copy proportion (MCP) mapping (Wang, Z. C., et al. (2004) *Cancer Res* 64(1):64-71; Seymour, A. B., et al. (1994) *Cancer Res* 54, 2761-4; Hahn, S. A., et al. (1995) *Cancer Res* 55, 4670-5; Kimura, M., et al. (1996) *Genes Chromosomes Cancer* 17, 88-93; Li et al., (2008) *MBC Bioinform.* 9, 204-219) may also be used to identify regions of amplification or deletion.

c. Methods for Detection of Biomarker Nucleic Acid Expression

Biomarker expression may be assessed by any of a wide variety of well-known methods for detecting expression of a transcribed molecule or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In preferred embodiments, activity of a particular gene is characterized by a measure of gene transcript (e.g. mRNA), by a measure of the quantity of translated protein, or by a measure of gene product activity. Biomarker expression can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In another embodiment, detecting or determining expression levels of a biomarker and functionally similar homologs thereof, including a fragment or genetic alteration thereof (e.g., in regulatory or promoter regions thereof) comprises detecting or determining RNA levels for the marker of interest. In one embodiment, one or more cells from the subject to be tested are obtained and RNA is isolated from the cells. In a preferred embodiment, a sample of breast tissue cells is obtained from the subject.

In one embodiment, RNA is obtained from a single cell. For example, a cell can be isolated from a tissue sample by laser capture microdissection (LCM). Using this technique, a cell can be isolated from a tissue section, including a stained tissue section, thereby assuring that the desired cell is isolated (see, e.g., Bonner et al. (1997) *Science* 278: 1481; Emmert-Buck et al. (1996) *Science* 274:998; Fend et al. (1999) *Am. J. Path.* 154: 61 and Murakami et al. (2000) *Kidney Int.* 58:1346). For example, Murakami et al., supra, describe isolation of a cell from a previously immunostained tissue section.

It is also be possible to obtain cells from a subject and culture the cells in vitro, such as to obtain a larger population of cells from which RNA can be extracted. Methods for establishing cultures of non-transformed cells, i.e., primary cell cultures, are known in the art.

When isolating RNA from tissue samples or cells from individuals, it may be important to prevent any further changes in gene expression after the tissue or cells has been removed from the subject. Changes in expression levels are known to change rapidly following perturbations, e.g., heat shock or activation with lipopolysaccharide (LPS) or other reagents. In addition, the RNA in the tissue and cells may quickly become degraded. Accordingly, in a preferred embodiment, the tissue or cells obtained from a subject is snap frozen as soon as possible.

RNA can be extracted from the tissue sample by a variety of methods, e.g., the guanidium thiocyanate lysis followed by CsCl centrifugation (Chirgwin et al., 1979, Biochemistry 18:5294-5299). RNA from single cells can be obtained as described in methods for preparing cDNA libraries from single cells, such as those described in Dulac, C. (1998) Curr. Top. Dev. Biol. 36, 245 and Jena et al. (1996) J. Immunol. Methods 190:199. Care to avoid RNA degradation must be taken, e.g., by inclusion of RNAsin.

The RNA sample can then be enriched in particular species. In one embodiment, poly(A)+RNA is isolated from the RNA sample. In general, such purification takes advantage of the poly-A tails on mRNA. In particular and as noted above, poly-T oligonucleotides may be immobilized within on a solid support to serve as affinity ligands for mRNA. Kits for this purpose are commercially available, e.g., the MessageMaker kit (Life Technologies, Grand Island, N.Y.).

In a preferred embodiment, the RNA population is enriched in marker sequences. Enrichment can be undertaken, e.g., by primer-specific cDNA synthesis, or multiple rounds of linear amplification based on cDNA synthesis and template-directed in vitro transcription (see, e.g., Wang et al. (1989) PNAS 86, 9717; Dulac et al., supra, and Jena et al., supra).

The population of RNA, enriched or not in particular species or sequences, can further be amplified. As defined herein, an "amplification process" is designed to strengthen, increase, or augment a molecule within the RNA. For example, where RNA is mRNA, an amplification process such as RT-PCR can be utilized to amplify the mRNA, such that a signal is detectable or detection is enhanced. Such an amplification process is beneficial particularly when the biological, tissue, or tumor sample is of a small size or volume.

Various amplification and detection methods can be used. For example, it is within the scope of the present invention to reverse transcribe mRNA into cDNA followed by polymerase chain reaction (RT-PCR); or, to use a single enzyme for both steps as described in U.S. Pat. No. 5,322,770, or reverse transcribe mRNA into cDNA followed by symmetric gap ligase chain reaction (RT-AGLCR) as described by R. L. Marshall, et al., PCR Methods and Applications 4: 80-84 (1994). Real time PCR may also be used.

Other known amplification methods which can be utilized herein include but are not limited to the so-called "NASBA" or "3SR" technique described in PNAS USA 87: 1874-1878 (1990) and also described in Nature 350 (No. 6313): 91-92 (1991); Q-beta amplification as described in published European Patent Application (EPA) No. 4544610; strand displacement amplification (as described in G. T. Walker et al., Clin. Chem. 42: 9-13 (1996) and European Patent Application No. 684315; target mediated amplification, as described by PCT Publication WO9322461; PCR; ligase chain reaction (LCR) (see, e.g., Wu and Wallace, Genomics 4, 560 (1989), Landegren et al., Science 241, 1077 (1988)); self-sustained sequence replication (SSR) (see, e.g., Guatelli et al., Proc. Nat. Acad. Sci. USA, 87, 1874 (1990)); and transcription amplification (see, e.g., Kwoh et al., Proc. Natl. Acad. Sci. USA 86, 1173 (1989)).

Many techniques are known in the state of the art for determining absolute and relative levels of gene expression, commonly used techniques suitable for use in the present invention include Northern analysis, RNase protection assays (RPA), microarrays and PCR-based techniques, such as quantitative PCR and differential display PCR. For example, Northern blotting involves running a preparation of RNA on a denaturing agarose gel, and transferring it to a suitable support, such as activated cellulose, nitrocellulose or glass or nylon membranes. Radiolabeled cDNA or RNA is then hybridized to the preparation, washed and analyzed by autoradiography.

In situ hybridization visualization may also be employed, wherein a radioactively labeled antisense RNA probe is hybridized with a thin section of a biopsy sample, washed, cleaved with RNase and exposed to a sensitive emulsion for autoradiography. The samples may be stained with hematoxylin to demonstrate the histological composition of the sample, and dark field imaging with a suitable light filter shows the developed emulsion. Non-radioactive labels such as digoxigenin may also be used.

Alternatively, mRNA expression can be detected on a DNA array, chip or a microarray. Labeled nucleic acids of a test sample obtained from a subject may be hybridized to a solid surface comprising biomarker DNA. Positive hybridization signal is obtained with the sample containing biomarker transcripts. Methods of preparing DNA arrays and their use are well known in the art (see, e.g., U.S. Pat. Nos: 6,618,6796; 6,379,897; 6,664,377; 6,451,536; 548,257; U.S. 20030157485 and Schena et al. (1995) *Science* 20, 467-470; Gerhold et al. (1999) *Trends In Biochem. Sci.* 24, 168-173; and Lennon et al. (2000) *Drug Discovery Today* 5, 59-65, which are herein incorporated by reference in their entirety). Serial Analysis of Gene Expression (SAGE) can also be performed (See for example U.S. Patent Application 20030215858).

To monitor mRNA levels, for example, mRNA is extracted from the biological sample to be tested, reverse transcribed, and fluorescently-labeled cDNA probes are generated. The microarrays capable of hybridizing to marker cDNA are then probed with the labeled cDNA probes, the slides scanned and fluorescence intensity measured. This intensity correlates with the hybridization intensity and expression levels.

Types of probes that can be used in the methods described herein include cDNA, riboprobes, synthetic oligonucleotides and genomic probes. The type of probe used will generally be dictated by the particular situation, such as riboprobes for in situ hybridization, and cDNA for Northern blotting, for example. In one embodiment, the probe is directed to nucleotide regions unique to the RNA. The probes may be as short as is required to differentially recognize marker mRNA transcripts, and may be as short as, for example, 15 bases; however, probes of at least 17, 18, 19 or 20 or more bases can be used. In one embodiment, the primers and probes hybridize specifically under stringent conditions to a DNA fragment having the nucleotide sequence corresponding to the marker. As herein used, the term "stringent conditions" means hybridization will occur only if there is at least 95% identity in nucleotide sequences.

In another embodiment, hybridization under "stringent conditions" occurs when there is at least 97% identity between the sequences.

The form of labeling of the probes may be any that is appropriate, such as the use of radioisotopes, for example, $^{32}P$ and $^{35}S$. Labeling with radioisotopes may be achieved, whether the probe is synthesized chemically or biologically, by the use of suitably labeled bases.

In one embodiment, the biological sample contains polypeptide molecules from the test subject. Alternatively, the biological sample can contain mRNA molecules from the test subject or genomic DNA molecules from the test subject.

In another embodiment, the methods further involve obtaining a control biological sample from a control subject, contacting the control sample with a compound or agent capable of detecting marker polypeptide, mRNA, genomic DNA, or fragments thereof, such that the presence of the marker polypeptide, mRNA, genomic DNA, or fragments thereof, is detected in the biological sample, and comparing the presence of the marker polypeptide, mRNA, genomic DNA, or fragments thereof, in the control sample with the presence of the marker polypeptide, mRNA, genomic DNA, or fragments thereof in the test sample.

d. Methods for Detection of Biomarker Protein Expression

The activity or level of a biomarker protein can be detected and/or quantified by detecting or quantifying the expressed polypeptide. The polypeptide can be detected and quantified by any of a number of means well known to those of skill in the art. Aberrant levels of polypeptide expression of the polypeptides encoded by a biomarker nucleic acid and functionally similar homologs thereof, including a fragment or genetic alteration thereof (e.g., in regulatory or promoter regions thereof) are associated with the likelihood of response of an immune disorder to an anti-immune disorder therapy (e.g., multiple-variable dose IL-2 therapy alone or in combination with one or more other anti-immune disorder therapies). Any method known in the art for detecting polypeptides can be used. Such methods include, but are not limited to, immunodiffusion, immunoelectrophoresis, radioimmunoassay (RIA), enzyme-linked immunosorbent assays (ELISAs), immunofluorescent assays, Western blotting, binder-ligand assays, immunohistochemical techniques, agglutination, complement assays, high performance liquid chromatography (HPLC), thin layer chromatography (TLC), hyperdiffusion chromatography, and the like (e.g., Basic and Clinical Immunology, Sites and Ten, eds., Appleton and Lange, Norwalk, Conn. pp 217-262, 1991 which is incorporated by reference). Preferred are binder-ligand immunoassay methods including reacting antibodies with an epitope or epitopes and competitively displacing a labeled polypeptide or derivative thereof.

For example, ELISA and RIA procedures may be conducted such that a desired biomarker protein standard is labeled (with a radioisotope such as $^{125}I$ or $^{35}S$, or an assayable enzyme, such as horseradish peroxidase or alkaline phosphatase), and, together with the unlabelled sample, brought into contact with the corresponding antibody, whereon a second antibody is used to bind the first, and radioactivity or the immobilized enzyme assayed (competitive assay). Alternatively, the biomarker protein in the sample is allowed to react with the corresponding immobilized antibody, radioisotope- or enzyme-labeled anti-biomarker proteinantibody is allowed to react with the system, and radioactivity or the enzyme assayed (ELISA-sandwich assay). Other conventional methods may also be employed as suitable.

The above techniques may be conducted essentially as a "one-step" or "two-step" assay. A "one-step" assay involves contacting antigen with immobilized antibody and, without washing, contacting the mixture with labeled antibody. A "two-step" assay involves washing before contacting, the mixture with labeled antibody. Other conventional methods may also be employed as suitable.

In one embodiment, a method for measuring biomarker protein levels comprises the steps of: contacting a biological specimen with an antibody or variant (e.g., fragment) thereof which selectively binds the biomarker protein, and detecting whether said antibody or variant thereof is bound to said sample and thereby measuring the levels of the biomarker protein.

Enzymatic and radiolabeling of biomarker protein and/or the antibodies may be effected by conventional means. Such means will generally include covalent linking of the enzyme to the antigen or the antibody in question, such as by glutaraldehyde, specifically so as not to adversely affect the activity of the enzyme, by which is meant that the enzyme must still be capable of interacting with its substrate, although it is not necessary for all of the enzyme to be active, provided that enough remains active to permit the assay to be effected. Indeed, some techniques for binding enzyme are non-specific (such as using formaldehyde), and will only yield a proportion of active enzyme.

It is usually desirable to immobilize one component of the assay system on a support, thereby allowing other components of the system to be brought into contact with the component and readily removed without laborious and time-consuming labor. It is possible for a second phase to be immobilized away from the first, but one phase is usually sufficient.

It is possible to immobilize the enzyme itself on a support, but if solid-phase enzyme is required, then this is generally best achieved by binding to antibody and affixing the antibody to a support, models and systems for which are well-known in the art. Simple polyethylene may provide a suitable support.

Enzymes employable for labeling are not particularly limited, but may be selected from the members of the oxidase group, for example. These catalyze production of hydrogen peroxide by reaction with their substrates, and glucose oxidase is often used for its good stability, ease of availability and cheapness, as well as the ready availability of its substrate (glucose). Activity of the oxidase may be assayed by measuring the concentration of hydrogen peroxide formed after reaction of the enzyme-labeled antibody with the substrate under controlled conditions well-known in the art.

Other techniques may be used to detect biomarker protein according to a practitioner's preference based upon the present disclosure. One such technique is Western blotting (Towbin et at., Proc. Nat. Acad. Sci. 76:4350 (1979)), wherein a suitably treated sample is run on an SDS-PAGE gel before being transferred to a solid support, such as a nitrocellulose filter. Anti-biomarker protein antibodies (unlabeled) are then brought into contact with the support and assayed by a secondary immunological reagent, such as labeled protein A or anti-immunoglobulin (suitable labels including $^{125}$I, horseradish peroxidase and alkaline phosphatase). Chromatographic detection may also be used.

Immunohistochemistry may be used to detect expression of biomarker protein, e.g., in a biopsy sample. A suitable antibody is brought into contact with, for example, a thin layer of cells, washed, and then contacted with a second, labeled antibody. Labeling may be by fluorescent markers, enzymes, such as peroxidase, avidin, or radiolabelling. The assay is scored visually, using microscopy.

Anti-biomarker protein antibodies, such as intrabodies, may also be used for imaging purposes, for example, to detect the presence of biomarker protein in cells and tissues of a subject. Suitable labels include radioisotopes, iodine ($^{125}$I, $^{121}$I), carbon ($^{14}$C), sulphur ($^{35}$S), tritium ($^{3}$H), indium ($^{112}$In) and technetium ($^{99}$mTc), fluorescent labels, such as fluorescein and rhodamine, and biotin.

For in vivo imaging purposes, antibodies are not detectable, as such, from outside the body, and so must be labeled, or otherwise modified, to permit detection. Markers for this purpose may be any that do not substantially interfere with the antibody binding, but which allow external detection. Suitable markers may include those that may be detected by X-radiography, NMR or MRI. For X-radiographic techniques, suitable markers include any radioisotope that emits detectable radiation but that is not overtly harmful to the subject, such as barium or cesium, for example. Suitable markers for NMR and MRI generally include those with a detectable characteristic spin, such as deuterium, which may be incorporated into the antibody by suitable labeling of nutrients for the relevant hybridoma, for example.

The size of the subject, and the imaging system used, will determine the quantity of imaging moiety needed to produce diagnostic images. In the case of a radioisotope moiety, for a human subject, the quantity of radioactivity injected will normally range from about 5 to 20 millicuries of technetium-99. The labeled antibody or antibody fragment will then preferentially accumulate at the location of cells which contain biomarker protein. The labeled antibody or antibody fragment can then be detected using known techniques.

Antibodies that may be used to detect biomarker protein include any antibody, whether natural or synthetic, full length or a fragment thereof, monoclonal or polyclonal, that binds sufficiently strongly and specifically to the biomarker protein to be detected. An antibody may have a $K_d$ of at most about $10^{-6}$M, $10^{-7}$ M, $10^{-8}$ M, $10^{-9}$ M, $10^{-10}$ M, $10^{-11}$ M, or $10^{-12}$M. The phrase "specifically binds" refers to binding of, for example, an antibody to an epitope or antigen or antigenic determinant in such a manner that binding can be displaced or competed with a second preparation of identical or similar epitope, antigen or antigenic determinant. An antibody may bind preferentially to the biomarker protein relative to other proteins, such as related proteins.

Antibodies are commercially available or may be prepared according to methods known in the art.

Antibodies and derivatives thereof that may be used encompass polyclonal or monoclonal antibodies, chimeric, human, humanized, primatized (CDR-grafted), veneered or single-chain antibodies as well as functional fragments, i.e., biomarker protein binding fragments, of antibodies. For example, antibody fragments capable of binding to a biomarker protein or portions thereof, including, but not limited to, Fv, Fab, Fab' and F(ab') 2 fragments can be used. Such fragments can be produced by enzymatic cleavage or by recombinant techniques. For example, papain or pepsin cleavage can generate Fab or F(ab') 2 fragments, respectively. Other proteases with the requisite substrate specificity can also be used to generate Fab or F(ab') 2 fragments. Antibodies can also be produced in a variety of truncated forms using antibody genes in which one or more stop codons have been introduced upstream of the natural stop site. For example, a chimeric gene encoding a F(ab') 2 heavy chain portion can be designed to include DNA sequences encoding the CH, domain and hinge region of the heavy chain.

Synthetic and engineered antibodies are described in, e.g., Cabilly et al., U.S. Pat. No. 4,816,567 Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0451216 B1; and Padlan, E. A. et al., EP 0519596 A1. See also, Newman, R. et al., BioTechnology, 10: 1455-1460 (1992), regarding primatized antibody, and Ladner et al., U.S. Pat. No. 4,946,778 and Bird, R. E. et al., Science, 242: 423-426 (1988)) regarding single-chain antibodies. Antibodies produced from a library, e.g., phage display library, may also be used.

In some embodiments, agents that specifically bind to a biomarker protein other than antibodies are used, such as peptides. Peptides that specifically bind to a biomarker protein can be identified by any means known in the art. For example, specific peptide binders of a biomarker protein can be screened for using peptide phage display libraries.

e. Methods for Detection of Biomarker Structural Alterations

The following illustrative methods can be used to identify the presence of a structural alteration in a biomarker nucleic acid and/or biomarker polypeptide molecule in order to, for example, identify sequences or agents that affect Tregs, Tcons, and/or the Tregs:Tcons ratio.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. USA 91:360-364), the latter of which can be particularly useful for detecting point mutations in a biomarker nucleic acid such as a biomarker gene (see Abravaya et al. (1995) Nucleic Acids Res. 23:675-682). This method can include the steps of collecting a sample of cells from a subject, isolating nucleic acid (e.g., genomic, mRNA or both) from the cells of the sample, contacting the nucleic acid sample with one or more primers which specifically hybridize to a biomarker gene under conditions such that hybridization and amplification of the biomarker gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al. (1990) Proc. Natl. Acad. Sci. USA 87:1874-1878), transcriptional amplification system (Kwoh, D. Y. et al. (1989) Proc. Natl. Acad. Sci. USA 86:1173-1177), Q-Beta Replicase (Lizardi, P. M. et al. (1988) Bio-Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a biomarker nucleic acid from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in biomarker nucleic acid can be identified by hybridizing a sample and control nucleic acids, e.g., DNA or RNA, to high density arrays containing hundreds or thousands of oligonucleotide probes (Cronin, M. T. et al. (1996) Hum. Mutat. 7:244-255; Kozal, M. J. et al. (1996) Nat. Med. 2:753-759). For example, biomarker genetic mutations can be identified in two dimensional arrays containing light-generated DNA probes as described in Cronin et al. (1996) supra. Briefly, a first hybridization array of probes can be used to scan through long stretches of DNA in a sample and control to identify base changes between the sequences by making linear arrays of sequential, overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene. Such biomarker genetic mutations can be identified in a variety of contexts, including, for example, germline and somatic mutations.

In yet another embodiment, any of a variety of sequencing reactions known in the art can be used to directly sequence a biomarker gene and detect mutations by comparing the sequence of the sample biomarker with the corresponding wild-type (control) sequence. Examples of sequencing reactions include those based on techniques developed by Maxam and Gilbert (1977) *Proc. Natl. Acad. Sci. USA* 74:560 or Sanger (1977) *Proc. Natl. Acad Sci. USA* 74:5463. It is also contemplated that any of a variety of automated sequencing procedures can be utilized when performing the diagnostic assays (Naeve (1995) *Biotechniques* 19:448-53), including sequencing by mass spectrometry (see, e.g., PCT International Publication No. WO 94/16101; Cohen et al. (1996) *Adv. Chromatogr.* 36:127-162; and Griffin et al. (1993) *Appl. Biochem. Biotechnol.* 38:147-159).

Other methods for detecting mutations in a biomarker gene include methods in which protection from cleavage agents is used to detect mismatched bases in RNA/RNA or RNA/DNA heteroduplexes (Myers et al. (1985) Science 230:1242). In general, the art technique of "mismatch cleavage" starts by providing heteroduplexes formed by hybridizing (labeled) RNA or DNA containing the wild-type biomarker sequence with potentially mutant RNA or DNA obtained from a tissue sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with SI nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl. Acad. Sci. USA* 85:4397 and Saleeba et al. (1992) *Methods Enzymol.* 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in biomarker cDNAs obtained from samples of cells. For example, the mutY enzyme of *E. coli* cleaves A at G/A mismatches and the thymidine DNA glycosylase from HeLa cells cleaves Tat G/T mismatches (Hsu et al. (1994) *Carcinogenesis* 15:1657-1662). According to an exemplary embodiment, a probe based on a biomarker sequence, e.g., a wild-type biomarker treated with a DNA mismatch repair enzyme, and the cleavage products, if any, can be detected from electrophoresis protocols or the like (e.g., U.S. Pat. No. 5,459,039.)

In other embodiments, alterations in electrophoretic mobility can be used to identify mutations in biomarker genes. For example, single strand conformation polymorphism (SSCP) may be used to detect differences in electrophoretic mobility between mutant and wild type nucleic acids (Orita et al. (1989) *Proc Natl. Acad. Sci USA* 86:2766; see also Cotton (1993) *Mutat. Res.* 285:125-144 and Hayashi (1992) *Genet. Anal. Tech. Appl.* 9:73-79). Single-stranded DNA fragments of sample and control biomarker nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet.* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to ensure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163; Saiki et al. (1989) *Proc. Natl. Acad. Sci. USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The compositions described herein can be used in a variety of diagnostic, prognostic, and therapeutic applications regarding biomarkers described herein.

f. Predictive Medicine

The present invention also pertains to the field of predictive medicine in which diagnostic assays, prognostic assays, and monitoring clinical trials are used for prognostic (predictive) purposes to thereby treat an individual prophylactically and/or determine the likelihood of efficacy. Accordingly, one aspect of the present invention relates to diagnostic assays for determining the presence, absence, amount, and/or activity level of a biomarker described herein, such as those listed in Table 1, in the context of a biological sample (e.g., blood, serum, cells, or tissue) to thereby determine whether an individual afflicted with an immune disorder is likely to respond to anti-immune disorder therapy (e.g., multiple-variable dose IL-2 therapy alone or in combination with one or more other anti-immune disorder therapies), whether in an original or recurrent immune disorder. Such assays can be used for prognostic or predictive purpose to thereby prophylactically treat an individual prior to the onset or after recurrence of a disorder characterized by or associated with biomarker polypeptide, nucleic acid expression or activity. The skilled artisan will appreciate that any method can use one or more (e.g., combinations) of biomarkers described herein, such as those listed in Table 1.

Another aspect of the present invention pertains to monitoring the influence of agents (e.g., drugs, compounds, and small nucleic acid-based molecules) on the expression or activity of a biomarker, such as Tregs proliferation, Tregs numbers, Tregs activity, Tregs:Tcons ratio, and the like.

The skilled artisan will also appreciate that, in certain embodiments, the methods of the present invention implement a computer program and computer system. For example, a computer program can be used to perform the algorithms described herein. A computer system can also store and manipulate data generated by the methods of the present invention which comprises a plurality of biomarker signal changes/profiles which can be used by a computer system in implementing the methods of this invention. In certain embodiments, a computer system receives biomarker expression data; (ii) stores the data; and (iii) compares the data in any number of ways described herein (e.g., analysis relative to appropriate controls) to determine the state of informative biomarkers from tissue affected by an immune disorder. In other embodiments, a computer system (i) compares the determined expression biomarker level to a threshold value; and (ii) outputs an indication of whether said biomarker level is significantly modulated (e.g., above or below) the threshold value, or a phenotype based on said indication.

In certain embodiments, such computer systems are also considered part of the present invention. Numerous types of computer systems can be used to implement the analytic methods of this invention according to knowledge possessed by a skilled artisan in the bioinformatics and/or computer arts. Several software components can be loaded into memory during operation of such a computer system. The software components can comprise both software components that are standard in the art and components that are special to the present invention (e.g., dCHIP software described in Lin et al. (2004) *Bioinformatics* 20, 1233-1240; radial basis machine learning algorithms (RBM) known in the art).

The methods of the invention can also be programmed or modeled in mathematical software packages that allow symbolic entry of equations and high-level specification of processing, including specific algorithms to be used, thereby freeing a user of the need to procedurally program individual equations and algorithms. Such packages include, e.g., Matlab from Mathworks (Natick, Mass.), Mathematica from Wolfram Research (Champaign, Ill.) or S-Plus from MathSoft (Seattle, Wash.).

In certain embodiments, the computer comprises a database for storage of biomarker data. Such stored profiles can be accessed and used to perform comparisons of interest at a later point in time. For example, biomarker expression profiles of a sample derived from tissue of a subject not affected by an immune disorder and/or profiles generated from population-based distributions of informative loci of interest in relevant populations of the same species can be stored and later compared to that of a sample derived from the subject's tissue affected by an immune disorder or subject's tissue suspected of being affected by an immune disorder.

In addition to the exemplary program structures and computer systems described herein, other, alternative program structures and computer systems will be readily apparent to the skilled artisan. Such alternative systems, which do not depart from the above described computer system and programs structures either in spirit or in scope, are therefore intended to be comprehended within the accompanying claims.

c. Diagnostic Assays

The present invention provides, in part, methods, systems, and code for accurately classifying whether a biological sample is associated with an immune disorder that is likely to respond to anti-immune disorder therapy (e.g., multiple-variable dose IL-2 therapy alone or in combination with one or more other anti-immune disorder therapies). In some embodiments, the present invention is useful for classifying a sample (e.g., from a subject) as associated with or at risk for responding to or not responding to anti-immune disorder therapy (e.g., multiple-variable dose IL-2 therapy alone or in combination with one or more other anti-immune disorder therapies) using a statistical algorithm and/or empirical data (e.g., the amount or activity of a biomarker described herein).

An exemplary method for detecting the amount or activity of a biomarker, and thus useful for classifying whether a sample is likely or unlikely to respond to anti-immune disorder therapy (e.g., multiple-variable dose IL-2 therapy alone or in combination with one or more other anti-immune disorder therapies) involves obtaining a biological sample from a test subject and contacting the biological sample with an agent, such as a protein-binding agent like an antibody or antigen-binding fragment thereof, or a nucleic acid-binding agent like an oligonucleotide, capable of detecting the amount or activity of the biomarker in the biological sample. In some embodiments, at least one antibody or antigen-binding fragment thereof is used, wherein two, three, four, five, six, seven, eight, nine, ten, or more such antibodies or antibody fragments can be used in combination (e.g., in sandwich ELISAs) or in serial. In certain instances, the statistical algorithm is a single learning statistical classifier system. For example, a single learning statistical classifier system can be used to classify a sample as a based upon a prediction or probability value and the presence or level of the biomarker. The use of a single learning statistical classifier system typically classifies the sample as, for example, a likely anti-immune disorder therapy (e.g., multiple-variable dose IL-2 therapy alone or in combination with one or more other anti-immune disorder therapies) responder or progressor sample with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Other suitable statistical algorithms are well known to those of skill in the art. For example, learning statistical classifier systems include a machine learning algorithmic technique capable of adapting to complex data sets (e.g., panel of markers of interest) and making decisions based upon such data sets. In some embodiments, a single learning statistical classifier system such as a classification tree (e.g., random forest) is used. In other embodiments, a combination of 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as random forests, classification and regression trees (C&RT), boosted trees, etc.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naive learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ). In certain embodiments, the method of the present invention further comprises sending the sample classification results to a clinician, e.g., an oncologist.

In another embodiment, the diagnosis of a subject is followed by administering to the individual a therapeutically effective amount of a defined treatment based upon the diagnosis.

In one embodiment, the methods further involve obtaining a control biological sample (e.g., biological sample from a subject who does not have an immune disorder or whose immune disorder is susceptible to anti-immune disorder therapy (e.g., multiple-variable dose IL-2 therapy alone or in combination with one or more other anti-immune disorder therapies), a biological sample from the subject during remission, or a biological sample from the subject during treatment for developing a progressing immune disorder despite anti-immune disorder therapy (e.g., multiple-variable dose IL-2 therapy alone or in combination with one or more other anti-immune disorder therapies).

d. Prognostic Assays

The diagnostic methods described herein can furthermore be utilized to identify subjects having or at risk of developing an immune disorder that is likely or unlikely to be responsive to anti-immune disorder therapy (e.g., multiple-variable dose IL-2 therapy alone or in combination with one or more other anti-immune disorder therapies). The assays described herein, such as the preceding diagnostic assays or the following assays, can be utilized to identify a subject having or at risk of developing a disorder associated with a misregulation of the amount or activity of at least one biomarker of the present invention, such as in an immune disorder. Alternatively, the prognostic assays can be utilized to identify a subject having or at risk for developing a disorder associated with a misregulation of the at least one biomarker of the present invention, such as in an immune disorder. Furthermore, the prognostic assays described herein can be used to determine whether a subject can be administered an agent (e.g., an agonist, antagonist, peptidomimetic, polypeptide, peptide, nucleic acid, small molecule, or other drug candidate) to treat a disease or disorder associated with the aberrant biomarker expression or activity.

e. Treatment Methods

Another aspect of the invention pertains to methods of modulating the expression or activity of one or more biomarkers described herein (e.g., Treg proliferation, Treg numbers, Treg activity, Treg apoptosis, Tregs:Tcons ratio, biomarkers listed in Table 1 and the Examples or fragments thereof, and the like) for therapeutic purposes. The biomarkers of the present invention have been demonstrated to correlate with treatment of immune disorders. Accordingly, the activity and/or expression of the biomarker, as well as the interaction between one or more biomarkers or a fragment thereof and its natural binding partner(s) or a fragment(s) thereof, can be modulated in order to treat immune disorders.

Modulatory methods of the invention, as described above, involve contacting a cell with one or more biomarkers of the invention, including one or more biomarkers listed in Table 1 and the Examples or a fragment thereof or agent that modulates one or more of the activities of biomarker activity associated with the cell. An agent that modulates biomarker activity can be an agent as described herein, such as a nucleic acid or a polypeptide, a naturally-occurring binding partner of the biomarker, an antibody against the biomarker, a combination of antibodies against the biomarker and antibodies against other immune related targets, one or more biomarkers agonist or antagonist, a peptidomimetic of one or more biomarkers agonist or antagonist, one or more biomarkers peptidomimetic, other small molecule, or small RNA directed against or a mimic of one or more biomarkers nucleic acid gene expression product.

An agent that modulates the expression of one or more biomarkers of the present invention, including one or more biomarkers of the invention, including one or more biomarkers listed in Table 1 and the Examples or a fragment thereof is, e.g., an antisense nucleic acid molecule, RNAi molecule, shRNA, mature miRNA, pre-miRNA, pri-miRNA, miRNA*, anti-miRNA, or a miRNA binding site, or a variant thereof, or other small RNA molecule, triplex oligonucleotide, ribozyme, or recombinant vector for expression of one or more biomarkers polypeptide. For example, an oligonucleotide complementary to the area around one or more biomarkers polypeptide translation initiation site can be synthesized. One or more antisense oligonucleotides can be added to cell media, typically at 200 µg/ml, or administered to a patient to prevent the synthesis of one or more biomarkers polypeptide. The antisense oligonucleotide is taken up by cells and hybridizes to one or more biomarkers mRNA to prevent translation. Alternatively, an oligonucleotide which binds double-stranded DNA to form a triplex construct to prevent DNA unwinding and transcription can be used. As a result of either, synthesis of biomarker polypeptide is blocked. When biomarker expression is modulated, preferably, such modulation occurs by a means other than by knocking out the biomarker gene.

Agents which modulate expression, by virtue of the fact that they control the amount of biomarker in a cell, also modulate the total amount of biomarker activity in a cell.

In one embodiment, the agent stimulates one or more activities of one or more biomarkers of the invention, including one or more biomarkers listed in Table 1 and the Examples or a fragment thereof. Examples of such stimulatory agents include active biomarker polypeptide or a fragment thereof and a nucleic acid molecule encoding the biomarker or a fragment thereof that has been introduced into the cell (e.g., cDNA, mRNA, shRNAs, siRNAs, small RNAs, mature miRNA, pre-miRNA, pri-miRNA, miRNA*, anti-miRNA, or a miRNA binding site, or a variant thereof, or other functionally equivalent molecule known to a skilled artisan). In another embodiment, the agent inhibits one or more biomarker activities. In one embodiment, the agent inhibits or enhances the interaction of the biomarker with its natural binding partner(s). Examples of such inhibitory agents include antisense nucleic acid molecules, anti-biomarker antibodies, biomarker inhibitors, and compounds identified in the screening assays described herein.

These modulatory methods can be performed in vitro (e.g., by contacting the cell with the agent) or, alternatively, by contacting an agent with cells in vivo (e.g., by administering the agent to a subject). In one embodiment, the method involves administering an agent (e.g., an agent identified by a screening assay described herein), or combination of agents that modulates (e.g., upregulates or downregulates) biomarker expression or activity. In another embodiment, the method involves administering one or more biomarkers polypeptide or nucleic acid molecule as therapy to compensate for reduced, aberrant, or unwanted biomarker expression or activity.

Stimulation of biomarker activity is desirable in situations in which the biomarker is abnormally downregulated and/or in which increased biomarker activity is likely to have a beneficial effect. Likewise, inhibition of biomarker activity is desirable in situations in which biomarker is abnormally upregulated and/or in which decreased biomarker activity is likely to have a beneficial effect.

In addition, these modulatory agents can also be administered in combination therapy with, e.g., chemotherapeutic agents, hormones, antiangiogens, radiolabelled, compounds, or with surgery, cryotherapy, and/or radiotherapy. The preceding treatment methods can be administered in conjunction with other forms of conventional therapy (e.g., standard-of-care treatments for immune disorders well known to the skilled artisan), either consecutively with, pre- or post-conventional therapy. For example, these modulatory agents can be administered with a therapeutically effective dose of an immunosuppressive agent or therapy.

The present invention also encompasses kits for detecting and/or modulating biomarkers described herein. A kit of the present invention may also include instructional materials disclosing or describing the use of the kit or an antibody of the disclosed invention in a method of the disclosed invention as provided herein. A kit may also include additional components to facilitate the particular application for which the kit is designed. For example, a kit may additionally contain means of detecting the label (e.g., enzyme substrates for enzymatic labels, filter sets to detect fluorescent labels, appropriate secondary labels such as a sheep anti-mouse-HRP, etc.) and reagents necessary for controls (e.g., control biological samples or standards). A kit may additionally include buffers and other reagents recognized for use in a method of the disclosed invention. Non-limiting examples include agents to reduce non-specific binding, such as a carrier protein or a detergent.

Other embodiments of the present invention are described in the following Examples. The present invention is further illustrated by the following examples which should not be construed as further limiting.

EXAMPLES

Example 1: Low-Dose IL-2 Enhances Tregs and the Tregs:Tcons Ratio

Clinically, low-dose IL-2 can enhance Treg. In a phase 1 study of steroid-refractory cGVHD, 8-week daily subcutaneous IL-2 ($1\times10^6$ IU/m$^2$) therapy was safe and tolerable (dosing up to $3\times10$ IU/m$^2$) (Koreth et al. (2011) *N. Engl. J. Med.* 365:2055-2066). Eligibility included cGVHD that had not responded to at least 0.25 mg/kg prednisone for a 4 week period, the absence of infection, and stable doses of immune suppression for 4 weeks prior. The study had a Phase 1 dose escalation design with 3 dose levels (0.3-, 1-, and $3\times10^6$ IU/m$^2$/day for 8 weeks).

Figure 2:
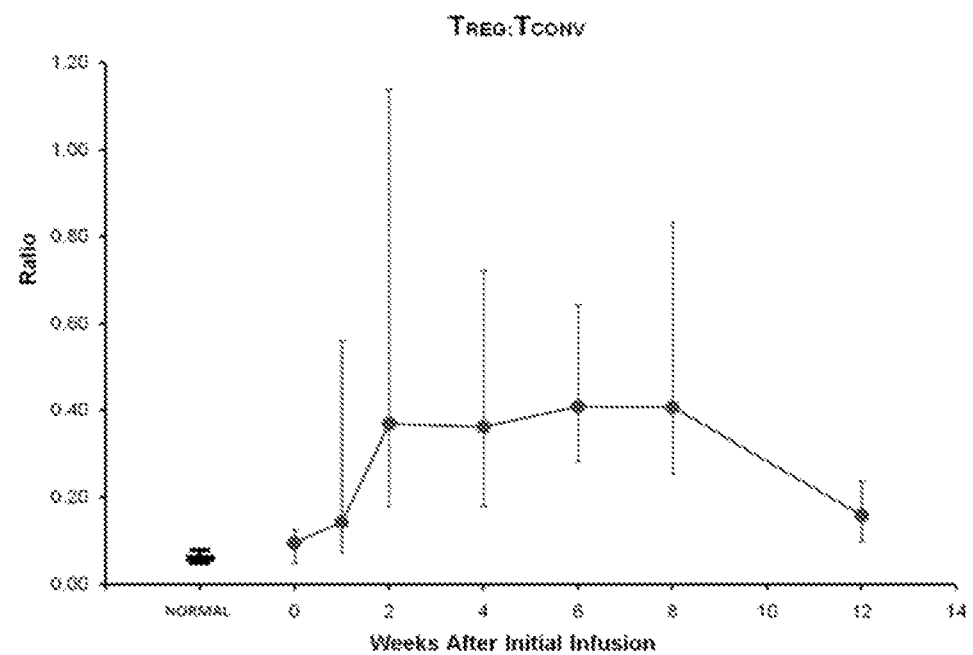
FIG. 2 shows the median Tregs:Tcons ratio on IL-2 therapy. There was a rapid rise and sustained plateau within a few weeks of starting IL-2, with a decline after stopping IL-2 at 8 weeks. Medians with inter-quartile range are shown.

Twenty-nine participants accrued: 28 evaluable for toxicity; 23 for response. IL-2 at $1\times10^6$ IU/m$^2$/day was determined to be MTD. Two participants developed dose-limiting-toxicity (thrombotic microangiopathy). None experienced GVHD flare. There was no malignant disease relapse. Twelve of 23 participants had objective clinical responses. Low-dose IL-2 selectively increased Treg counts in vivo (FIG. 1) without impacting conventional CD4+ T (Tcon) counts. The Tregs:Tcons ratio also rose (FIG. 2). NK cell counts rose to a lesser extent. Low-dose IL-2 did not impact CD8+ T, B, or NKT counts. Tregs count and Tregs:Tcons ratio remained elevated at 8 weeks of IL-2, then declined off IL-2. IL-2-induced Tregs expressed FOXP3+ and were functional in Tcons suppression assays. Importantly, clinical and immunologic responses were sustained in responders on extended-duration IL-2 therapy beyond 12 weeks, enabling a taper of concomitant immunosuppression.

However, only half of evaluable participants had a clinical response (partial response, PR) despite preferential in vivo Treg enhancement in all (Koreth et al. (2011) *N. Engl. J. Med.* 365:2055-2066). Even with daily subcutaneous (SC) low-dose IL-2 therapy, half of participants do not obtain clinical benefit (Koreth et al. (2011) *N. Engl. J. Med.* 365:2055-2066). These data indicate that low-dose IL-2 is safe in cGVHD and preferentially augments Treg.

Figure 3:
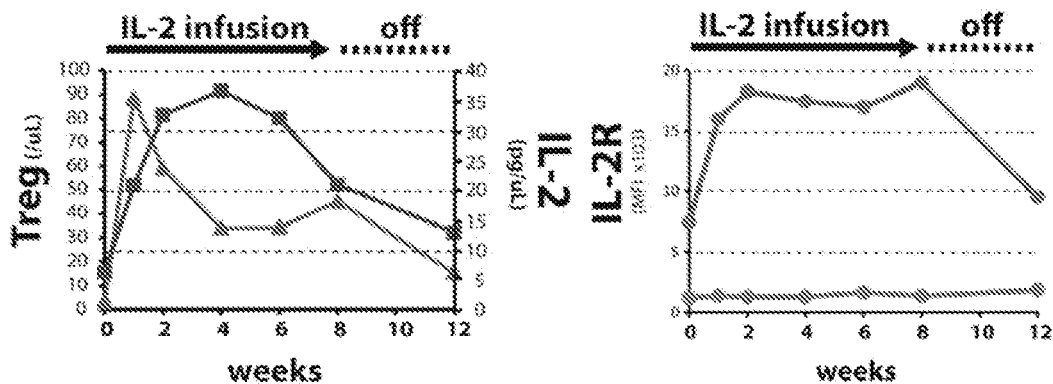
FIG. 3 shows that IL-2 levels fall as absolute numbers of Tregs increase. The left panel shows Treg cell count and IL-2 levels during IL-2 treatment. Treg count/μL (boxes) versus plasma IL-2 level in pg/μL (triangles) during an 8-week IL-2 treatment regimen is indicated. The right panel shows IL-2 receptor a (CD25; IL-2R) cell surface expression. Sustained increase of IL-2R expression was noted for Tregs (top line) but not Tcons (bottom line) during low-dose IL-2.

Plasma IL-2 levels rose rapidly (e.g., by week 1) during fixed-dose IL-2 therapy, then, despite daily IL-2 administration, declined while Tregs count rise (Matsuoka et al. (2013) *Sci. Transl. Med.* 5:179ra43) and it is believed that the result is due to increased IL-2 sequestration via binding to high affinity IL-2 receptors (CD25) constitutively expressed on Tregs. Thereafter, as the absolute number of Treg increase and there is a further increase in CD25 expression on Tregs during IL-2 therapy (Matsuoka et al. (2013) *Sci. Transl. Med.* 5:179ra43) (FIG. 3).

Similar analyses were previously performed to analyze low-dose IL-2 effects initiated earlier in the cGVHD course, before the onset of irreversible parenchymal, cutaneous, and musculoskeletal changes. In this phase 2 study, patients who previously received ≤2 lines of cGVHD therapy were treated with a 12 week course of daily SC IL-2 at $1\times10^6$ IU/m$^2$/day (i.e., the MTD described above). After a 4 week hiatus, patients experiencing clinical benefit could receive extended duration IL-2 therapy, during which taper of concomitant immunosuppression was permitted. The primary objective was to determine cGVHD clinical response rate. Patients underwent cGVHD assessment per NIH criteria (Filipovich et al. (2005) *Biol. Blood Marrow Transplant.* 11:945-956) at baseline, 6, 12, and 16 weeks on study, and at 1 year. Secondary objectives included assessment of toxicity; immunologic impact; correlation of immune effects with clinical response; and corticosteroid use at 1 year. Thirty-five patients with a median of 4 sites of cGVHD involvement and a median of 1 prior cGVHD therapies were enrolled. As described above, low-dose IL-2 treatment was generally well tolerated and no patient's malignancy relapsed. At week 12, cGVHD objective responses (PR) were documented in 20 of 33 evaluable patients and 2 patients had cGVHD progression. Sites of cGVHD response included skin (n=9); joint/fascia/muscle (n=3); liver (n=7); GI tract (n=3); GU tract (n=1); and lung (n=5). Twenty-three patients with clinical benefit (PR or SD with minor response) initiated extended IL-2 therapy after week 16, with a mean 50% steroid dose taper (range, 0-100) during a median 5.8 months (range, 0.4-26.1) of extended IL-2 therapy as of Dec. 31, 2013. 14 remain on extended IL-2 therapy.

Figure 4:
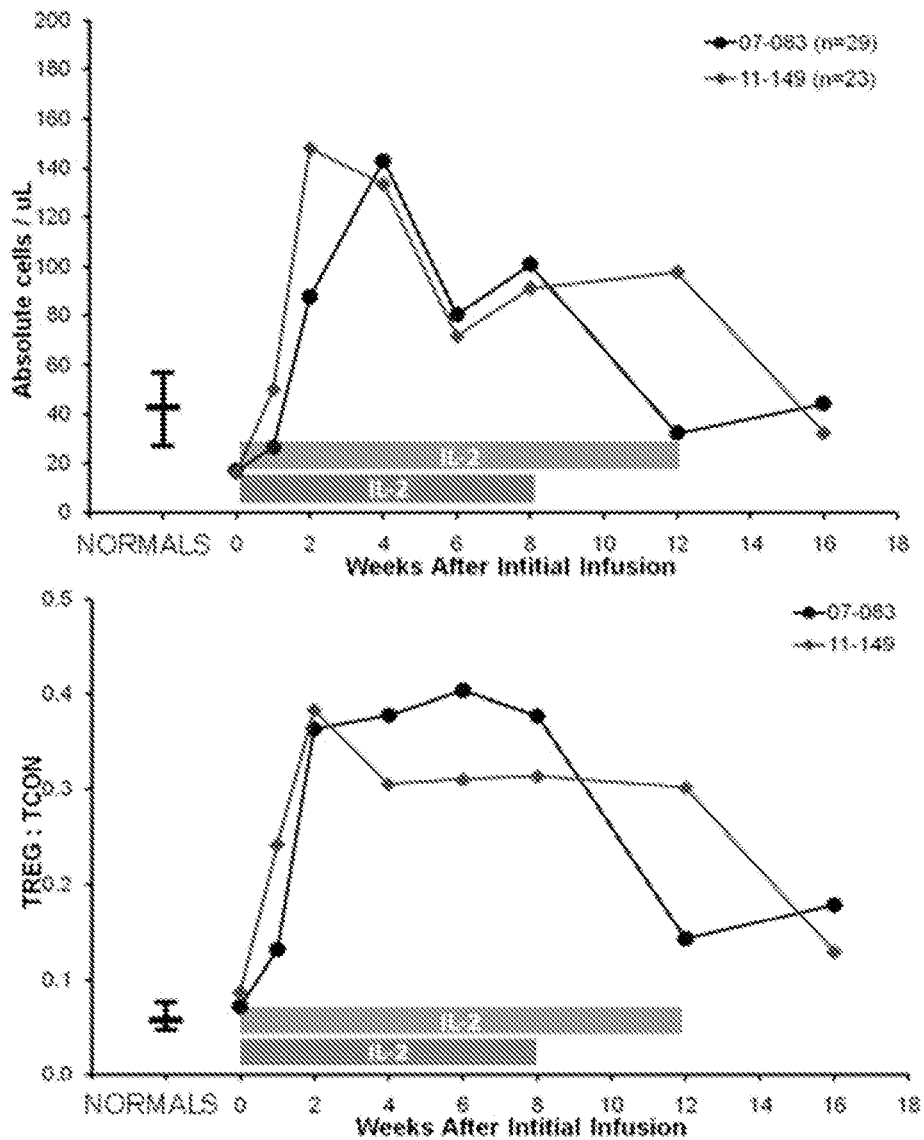
FIG. 4 shows the results of IL-2-mediated Treg effects in phase 1 versus phase 2 studies. The left panel shows $CD4^+CD25^+CD127^-$ Tregs count/μL in phase 1 (circles) vs. phase 2 trial (diamonds). The right panel shows the Tregs:Tcons ratio for phase 1 (circles) vs. phase 2 trial (diamonds). Bars indicate duration of IL-2 treatment in phase 1 (8 weeks, lower bar) vs. phase 2 (12 weeks, upper bar).

Immunologically, similar to the results described above, low-dose IL-2 induced a similar rise in Tregs count without affecting Tcons, and median Treg:Tcon ratio rose (FIG. 4). Treg count and Treg:Tcon ratio remained elevated at week 12 and declined after cessation of IL-2. This phase 2 trial confirms the clinical impact of low-dose IL-2 in cGVHD and its functional effect on Treg and Tcon homeostasis in vivo. Ongoing laboratory studies will determine whether immunologic effects can be correlated with clinical response and the extent to which they persist after low-dose IL-2 therapy.

Figure 5:
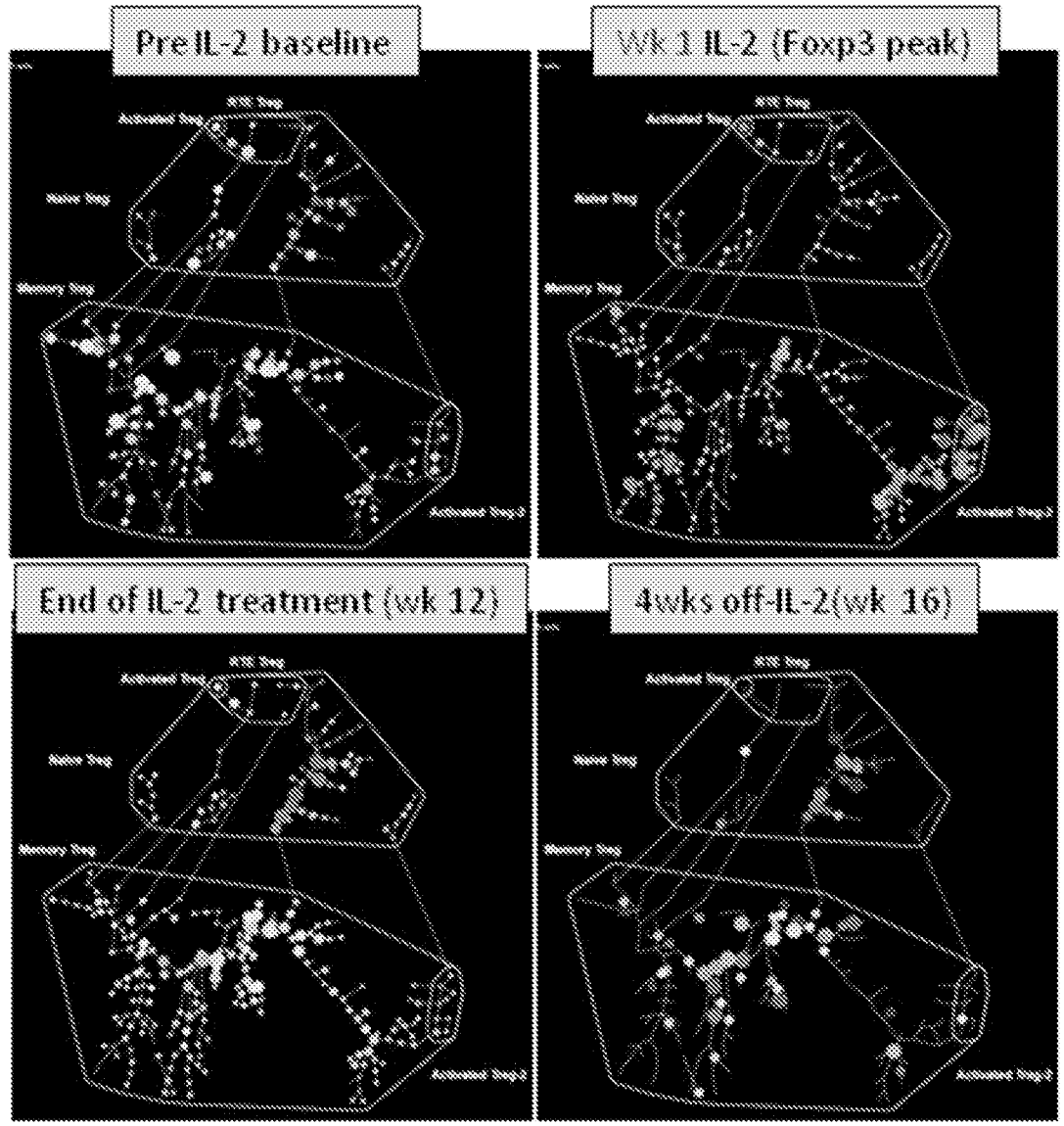
FIG. 5 shows the results of SPADE analysis of Treg subsets for FoxP3 expression using CyTOF. In a representative patient on the 12 week low-dose IL-2 study, RTE/naive and memory Treg populations cluster separately in the SPADE Tree diagram and activated Treg subpopulations are further delineated within each group. Bubble size reflects cell number and FoxP3 expression level intensities are shown. In the upper left panel, at pre-IL-2 baseline, memory Treg populations had greater FoxP3 expression. In the upper right panel, at 1 week, IL-2 induced FoxP3 in all Treg subsets. In the lower left panel, at 12 weeks of IL-2, memory Treg had greater FoxP3 expression. In the lower right panel, after IL-2 discontinuation, Treg populations were considerably depleted, with limited residual FoxP3 expression in memory Treg subsets.

It has further been determined herein that peak Tregs proliferation occurred by 1 week after start of an IL-2 induction regimen in all Treg subsets along with an increase in Tregs population size. Mass cytometry by time-of-flight (CyTOF) analysis using SPADE (spanning-tree progression analysis of density-normalized events) was chosen since CyTOF avoids background noise inherent in fluorescence cytometry due to spectral overlap and auto-fluorescence, and provides up to 37 lanthanide isotopes simultaneously for measuring antigen-bound antibodies or other probes with high sensitivity. Regarding Tregs proliferation, limited Ki-67 proliferation restricted to small subsets of activated memory and naive Treg was observed at baseline. Peak Treg proliferation occurred by 1 week after start of IL-2 in all Treg subsets along with an increase in Treg population size (FIG. 5). Tregs proliferation, however, subsided after week 2 with a fall in Ki-67 expression (proliferation) alongside the preservation of expanded Treg subpopulations at week 12 of IL-2 treatment. However, by 4 weeks after IL-2 discontinuation Ki-67 Treg proliferation levels and Treg populations were depleted. A similar temporal pattern of Tregs activation was observed using pSTAT5 and FoxP3 markers, with an initial early generalized enhancement across Treg subpopulations that later subsided during IL-2 treatment despite the continued preservation of enhanced Treg population size (FIG. 5). A fall in Treg activation marker expression and a considerable depletion of Treg populations was then observed by 4 weeks after IL-2 discontinuation.

Not all patients responded and benefit in responders was often partial. In phase 1 data, cGVHD clinical responses appeared linked to higher Treg:Tcon ratio at study entry, but not to rise in circulating Treg count or Treg:Tcon ratio. The lack of clinical response in some patients despite in vivo Treg enhancement is also consistent with our data documenting Treg cell-intrinsic defects (e.g., shortened telomeres) in advanced cGVHD (Kawano et al. (2011) *Blood* 118:5021-5030). Moreover, the enhancement of Treg was rapidly attenuated on stopping IL-2, indicating that additional interventions are necessary for advanced cGVHD patients with profound Treg deficiencies to further increase Treg numbers and function and to delay or prevent their decline.

Such additional interventions have been determined herein to comprise maintenance regimens involving individual patient IL-2 dose escalation after induced plasma IL-2 levels in order to more fully restore plasma IL-2 levels and further augment Treg proliferation, activation and neogenesis without inducing Tcon activation or excess adverse events. It is believed that since Treg cells constitutively express CD25, which contributes to the formation of the high affinity IL-2 receptor, there is an increase in IL-2 sequestration and plasma IL-2 levels drop despite continued daily IL-2 dosing. Additionally, IL-2 induces increased CD25 expression on Treg, further increasing IL-2 uptake. IL-2 induced Treg proliferation, pSTAT5 and FoxP3 Treg activation. Indeed, RTE Treg generation declined later in the course of IL-2 therapy coincident with a fall in plasma IL-2 level. In this manner, IL-2-induced Treg enhancement occurs in vivo and tachyphylaxis due to diminution of plasma IL-2 levels after binding by increased numbers of circulating Treg with higher CD25 expression is avoided. These methods overcome the partial clinical cGVHD responses noted despite in vivo Treg augmentation with low-dose IL-2. Individual patient IL-2 dose escalation at the time of anticipated fall in plasma IL-2 levels provides a mechanism to restore IL-2 levels and further augment Treg proliferation and activation without inducing Tcon activation or constitutional AEs.

Figure 6:
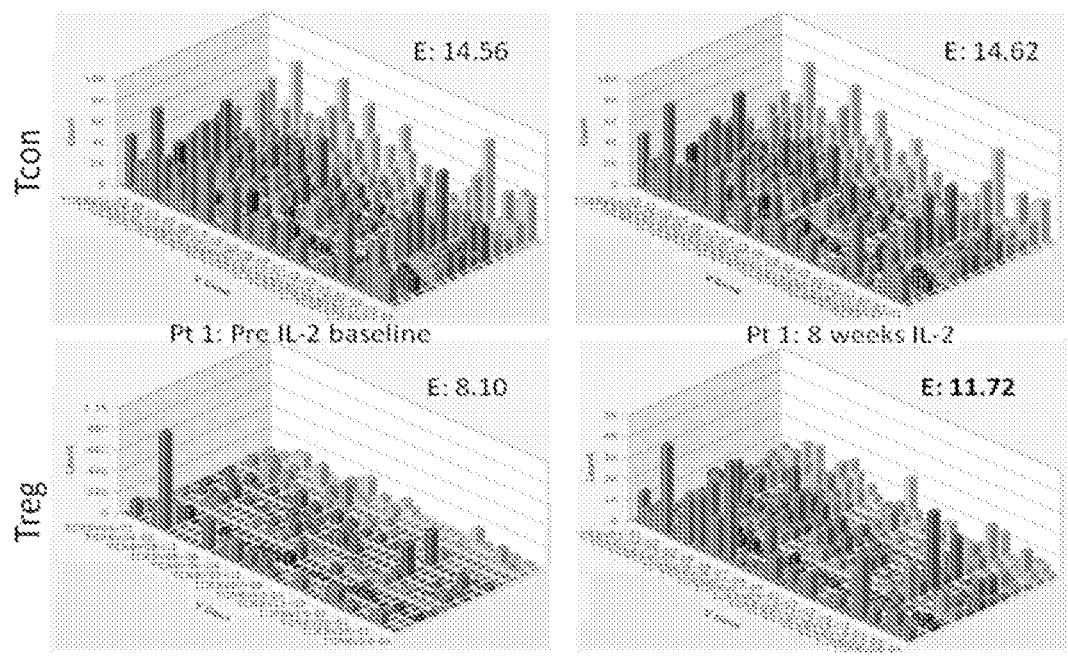
FIG. 6 shows the results of T cell receptor (TCR) sequence analysis of Tregs and Tcons repertoire diversity with low-dose IL-2. Treg entropy (E) increased in the cGVHD patient after 8 week IL-2, without change in Tcon entropy. Tcons are shown in the upper panels and Tregs are shown in the lower panels. Entropy (E) is indicated for each panel. Additional productive Treg TCR sequences were apparent in the lower right vs. left panel despite an increase in Y-axis scale (1K→5K).
Figure 7:
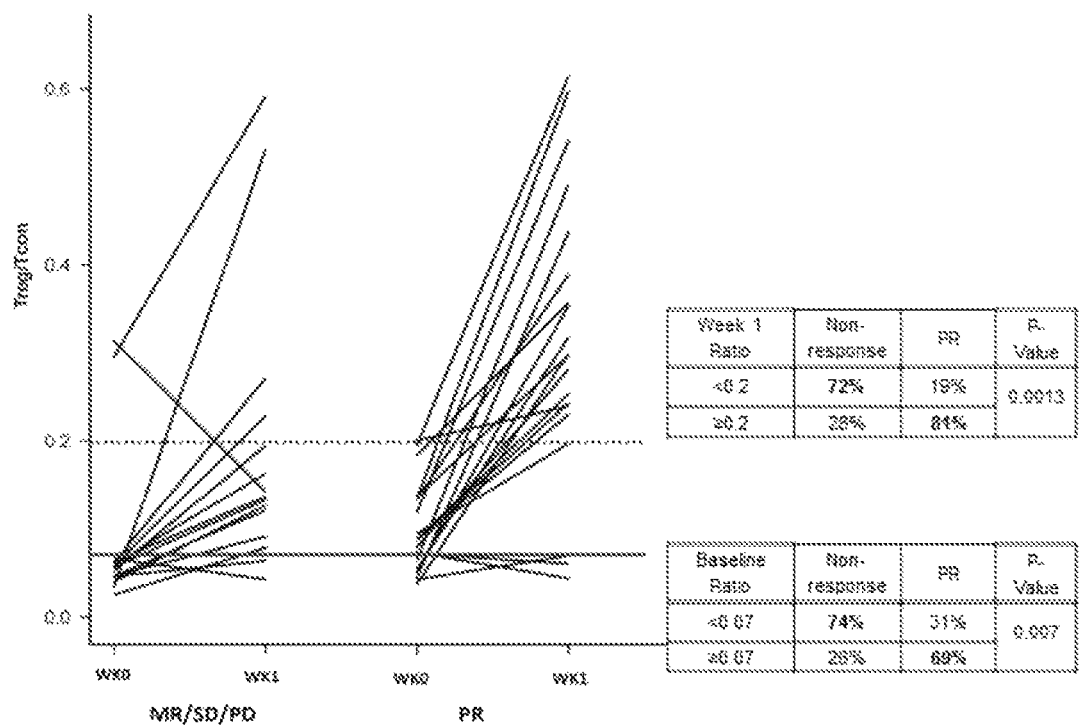
FIG. 7 shows response predictors to IL-2 therapy using Tregs:Tcons ratios. The Tregs:Tcons ratio at baseline and week 1 for clinical responders (PR) vs non responders (SD/MR/PD) is shown. All data are derived from fixed dose IL-2 administration.

Moreover, it has been determined herein that dramatic enhancement of the Treg repertoire is one of the mechanisms by which low-dose IL-2 enhances T cell tolerance and suppression of immune-mediated inflammation in vivo and further demonstrate the selective effects of low-dose IL-2 on Tregs in vivo. In particular, T cell receptor (TCR) sequencing (Adaptive Biotechnologies, Seattle, Wash.; available on the World Wide Web at immunoseq.com) was used to interrogate repertoire diversity (Robins et al. (2012) *J. Immunol.* Methods 375:14-19; Robins et al. (2009) *Blood* 114:4099-4107; Robins et al. (2010) *Sci. Transl. Med.* 2:47ra64). The assay utilizes primers to 45 VP and all 13 JP segments with multiplex PCR to amplify the rearranged CDR3 region of the TCR, spanning the variable region formed by the junction of the V, D, and J segments and their associated non-templated insertions. The number and frequency of TCR sequences was used to characterize the diversity of the T cell repertoire as measured by entropy, wherein higher entropy scores reflected greater log diversity within TCR frequencies for each sample. TCR sequence analysis also enabled tracking of individual T cell clones in serial patient samples over time. The results in cGVHD patients indicated a 2-3 log increase in Treg TCR diversity and no change in Tcon diversity after low-dose IL-2 therapy (FIG. 6). When combining the data, FIG. 7 shows response predictors whereby predicted response is stratified according to baseline or week 1 ratio of Tregs:Tcons.

It has also been determined herein that in BH-3 profiling analysis, IL-2 treatment restored extrinsic and intrinsic pathway apoptosis sensitivity of Tregs to more physiologic levels.

Example 2: Representative Multiple-Variable Dose IL-2 Therapeutic Regimen

The following provides a representative, non-limiting embodiment of the multiple-variable dose IL-2 therapeutic methods of the present invention.

The following patient population criteria are used: 1) adult and pediatric participants with chronic GVHD and inadequate response to systemic steroids; 2) persistent or recurrent chronic GVHD despite at least 2 prior systemic therapies (including steroids); 3) no uncontrolled active infection; 4) no malignant disease relapse; and 5) Karnofsky PS≥60.

Specific inclusion and exclusion criteria are detailed below:

1) Number of participants: 20 (10 adult; 10 pediatric);

2) Study design and methodology: Adult (n=10) and pediatric (n=10) patients with refractory cGVHD will receive daily SC IL-2 dose-escalated in each patient every 2 weeks for 3 dose-levels (in the absence of DLTs or severe non-DLT AEs), and maintained at their individual MTD for 6 weeks.

Figure 9:
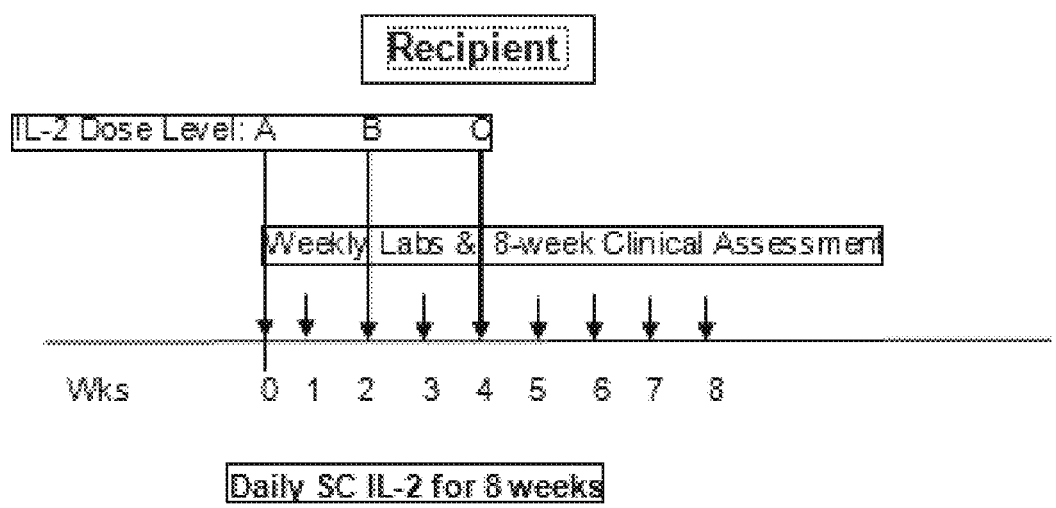
FIG. 9 shows a schematic diagram showing the Phase I dosing schedule for multiple-variable dose IL-2 therapeutic regimen.

3) Phase I (See FIG. 9 for a schematic diagram showing the dosing schedule)

Safety and efficacy analyses are as follows: The primary endpoint is the safety, toxicity, and MTD of individual patient dose-escalated IL-2. Secondary endpoints are the clinical and immunologic impact of individual patient dose-escalated IL-2, including 1) assessment of immunologic impact in refractory cGVHD; 2) assessment of clinical cGVHD response; and 3) correlation of immunologic effects with clinical response, and comparison with immunologic and clinical responses of fixed-dose IL-2 treated patients.

Evaluation (by 8 weeks) is as follows: 1) assessment of severe hematologic toxicity; 2) assessment of grade 3 or higher non-hematologic toxicities; 3) assessment of life-threatening infections; 4) assessment of immunologic impact; and 5) assessment of GVHD response or progression.

Participants can continue previously initiated cGVHD therapies during the 8-week study. The specific doses and schedule of these agent(s) are not important for the objectives of the study, and dose adjustments per institutional standards (e.g. adjustments based on drug levels) are permitted. While taper of concomitant cGVHD therapies during the 8-week study is not generally intended, such modifications, if clinically necessary per the treating physician, are permitted. The dose of steroids is documented at study entry and at week 8.

Peripheral blood samples obtained before, during, and after therapy are utilized to assess the immunologic effects of treatment. Such studies include:

1) Phenotypic analysis of lymphocyte subsets: Incubation of peripheral blood with monoclonal antibodies specific for lymphocyte markers is used to identify functionally distinct lymphocyte subsets. After incubation of peripheral blood cells with directly fluorochrome-conjugated monoclonal antibodies, individual subsets are enumerated by flow cytometry. Antibody panels have been developed for CD4+ Tregs, as well as other CD4 and CD8 T cell subsets, B cells and natural killer cells. This phenotypic analysis provides a quantitative way to assess thymic neogenesis, as well as proliferation and apoptosis-susceptibility of phenotypically well-defined T cell subsets. These allow measurement of the homeostatic balance of each T cell population in response to dose-escalated IL-2 therapy. In studies combining ECP, these changes are correlated with dose of ECP treated cells, determined by flow cytometric cell counts of the reinfused buffy coat from each ECP procedure.

2) Plasma cytokines: ELISA assays is used to measure levels of IL-2 in plasma samples. Other cytokines, such as IL-7, IL-10, and IL-15, which play a role in T cell homeostasis, can also be measured in these samples if needed.

3) Functional assays: To assess the functional capacity of Treg cells that expand in vivo in response to treatment, selected samples are used to assess their immune suppressive ability. In these experiments, Tregs are purified by high speed cell sorting and subsequently tested for their ability to suppress the proliferation of autologous T cells.

4) DNA analyses: Additional genetic analyses (e.g., TCR sequencing) can be considered to assess immune cell reconstitution, and banked DNA and cell samples can be be accessed for such analyses.

Taken together, these assays quantify the effects of individual patient IL-2 dose-escalation on participant immune cells.

Participants are selected according to the following eligibility criteria: 1) Recipient of 7-8/8 HLA-matched (HLA-A, -B, -C, -DRB1) allogeneic hematopoietic stem cell transplantation; and 2) Participants must have steroid-refractory cGVHD despite use of 2 or more therapies. Steroid-refractory cGVHD is defined as having persistent signs and symptoms of cGVHD (Tables 2 and 3) despite the use of prednisone at >0.25 mg/kg/day (or 0.5 mg/kg every other day) for at least 4 weeks (or equivalent dosing of alternate glucocorticoids) without complete resolution of signs and symptoms. Participants with either extensive or limited chronic GVHD requiring systemic therapy are eligible.

TABLE 2

Definite and Probable cGVHD Manifestations

| Organ System | Definite manifestations of chronic GVHD | Possible manifestations of chronic GVHD |
|---|---|---|
| Skin | Scleroderma (superficial or fasciitis), lichen planus, vitiligo, scarring alopecia, hyperkeratosis pilaris, contractures from skin immobility, nail bed dysplasia | Eczematoid rash, dry skin, maculopapular rash, hair loss, hyperpigmentation |
| Mucous membranes | Lichen planus, non-infectious ulcers, corneal erosions/non-infectious conjunctivitis | Xerostomia, keratoconjunctivitis sicca |
| GI tract | Esophageal strictures, steatorrhea | Anorexia, malabsorption, weight loss, diarrhea, abdominal pain |
| Liver | None | Elevation of alkaline phosphatase, transaminitis, cholangitis, hyperbilirubinemia |
| GU tract | Vaginal stricture, lichen planus | Non-infectious vaginitis, vaginal atrophy |
| Musculoskeletal/Serosa | Non-septic arthritis, myositis, myasthenia, polyserositis, contractures from joint immobilization | Arthralgia |
| Hematologic | None | Thrombocytopenia, eosinophilia, autoimmune cytopenias |
| Lung | Bronchiolitis obliterans | Bronchiolitis obliterans with organizing pneumonia, interstitial pneumonitis |

TABLE 3

Chronic GVHD Symptom Scoring Scale
Have you had any of the following problems in the past 2 weeks?

|  | Not at all | Slightly | Moderately | Quite a bit | Extremely |
|---|---|---|---|---|---|
| SKIN: |  |  |  |  |  |
| a. Abnormal skin color | 0 | 1 | 2 | 3 | 4 |
| b. Rashes | 0 | 1 | 2 | 3 | 4 |
| c. Thickened skin | 0 | 1 | 2 | 3 | 4 |
| d. Sores on skin | 0 | 1 | 2 | 3 | 4 |
| e. Itchy skin | 0 | 1 | 2 | 3 | 4 |
| EYES AND MOUTH: |  |  |  |  |  |
| f. Dry eyes | 0 | 1 | 2 | 3 | 4 |
| g. Need to use eyedrops frequently | 0 | 1 | 2 | 3 | 4 |

TABLE 3-continued

Chronic GVHD Symptom Scoring Scale
Have you had any of the following problems in the past 2 weeks?

|  | Not at all | Slightly | Moderately | Quite a bit | Extremely |
|---|---|---|---|---|---|
| h. Difficulty seeing clearly | 0 | 1 | 2 | 3 | 4 |
| i. Need to avoid certain foods due to mouth pain | 0 | 1 | 2 | 3 | 4 |
| j. Ulcers in mouth | 0 | 1 | 2 | 3 | 4 |
| k. Receiving nutrition from an intravenous line or feeding tube | 0 | 1 | 2 | 3 | 4 |
| BREATHING: | | | | | |
| l. Frequent cough | 0 | 1 | 2 | 3 | 4 |
| m. Colored sputum | 0 | 1 | 2 | 3 | 4 |
| n. Shortness of breath with exercise | 0 | 1 | 2 | 3 | 4 |
| o. Shortness of breath at rest | 0 | 1 | 2 | 3 | 4 |
| p. Need to use oxygen | 0 | 1 | 2 | 3 | 4 |
| EATING AND DIGESTION: | | | | | |
| q. Difficulty swallowing solid foods | 0 | 1 | 2 | 3 | 4 |
| r. Difficulty swallowing liquids | 0 | 1 | 2 | 3 | 4 |
| s. Vomiting | 0 | 1 | 2 | 3 | 4 |
| t. Weight loss | 0 | 1 | 2 | 3 | 4 |
| MUSCLES AND JOINTS: | | | | | |
| u. Joint and muscle aches | 0 | 1 | 2 | 3 | 4 |
| v. Limited joint movement | 0 | 1 | 2 | 3 | 4 |
| w. Muscle cramps | 0 | 1 | 2 | 3 | 4 |
| x. Weak muscles | 0 | 1 | 2 | 3 | 4 |
| ENERGY: | | | | | |
| y. Loss of eneng | 0 | 1 | 2 | 3 | 4 |
| z. Need to sleep more/take naps | 0 | 1 | 2 | 3 | 4 |
| Aa. Fevers | 0 | 1 | 2 | 3 | 4 |
| MENTAL AND EMOTIONAL: | | | | | |
| Bb. Depression | 0 | 1 | 2 | 3 | 4 |
| Cc. Anxiety | 0 | 1 | 2 | 3 | 4 |
| Dd. Difficulty sleeping | 0 | 1 | 2 | 3 | 4 |

Stable dose of glucocorticoids for 4 weeks prior to enrollment.

No addition or subtraction of other immunosuppressive medications (e.g., calcineurin-inhibitors, sirolimus, mycophenolate-mofetil) for 4 weeks prior to enrollment. The dose of immunosuppressive medicines may be adjusted based on the therapeutic range of that drug.

Participants must have adequate organ function as defined below:

1) Hepatic: Adequate hepatic function (total bilirubin≤2.0 mg/dl-exception permitted in participants with Gilbert's Syndrome; AST (SGOT)/ALT (SGPT)≤2× institutional ULN), unless hepatic dysfunction is a manifestation of presumed cGVHD. For participants with abnormal LFTs as the sole manifestation of cGVHD, documented GVHD on liver biopsy will be required prior to enrollment. Abnormal LFTs in the context of active cGVHD involving other organ systems may also be permitted if the treating physician documents the abnormal LFTs as being consistent with hepatic cGVHD, and a liver biopsy will not be mandated in this situation;

2) Pulmonary: FEV1≥50% or DLCO(Hb)≥40% of predicted, unless pulmonary dysfunction is deemed to be due to chronic GVHD;

3) Renal: Serum creatinine≤institutional ULN or creatinine clearance>60 mL/min/1.73 m$^2$ for participants with creatinine levels above institutional normal;

4) Pediatric patients must have creatinine clearance≥60 mL/min/1.73 m$^2$ regardless of serum creatinine level;

5) Adequate bone marrow function indicated by absolute neutrophil count (ANC)≥1000/mcL and platelets≥50,000/mcL without growth factors or transfusions;

6) Cardiac: No myocardial infarction within 6 months prior to enrollment or NYHA Class III or IV heart failure, uncontrolled angina, severe uncontrolled ventricular arrhythmias, or electrocardiographic evidence of acute ischemia or active conduction system abnormalities. Prior to study entry, any ECG abnormality at screening must be documented by the investigator as not medically relevant;

7) Karnofsky/Lansky performance status≥60% (Table 4);

TABLE 4

Performance Status Criteria
Karnofsky and Lansky performance scores are intended to be multiples of 10

| ECOG (Zubrod) | | Karnofsky | | Lansky* | |
|---|---|---|---|---|---|
| Score | Description | Score | Description | Score | Description |
| 0 | Fully active, able to carry on all pre-disease performance without restriction. | 100 | Normal, no complaints, no evidence of disease | 100 | Fully active, normal. |
| | | 90 | Able to carry on normal activity, minor signs or symptoms of disease. | 90 | Minor restrictions in physically strenuous activity. |
| 1 | Restricted in physically strenuous activity but ambulatory and able to carry out work of a light or sedentary nature, e.g., light housework, office work. | 80 | Normal activity with effort; some signs or symptoms of disease. | 80 | Active, but tires more quickly |
| | | 70 | Cares for self, unable to carry on normal activity or do active work. | 70 | Both greater restriction of and less time spent in play activity. |
| 2 | Ambulatory and capable of all self-care but unable to carry out any work activities. Up and about more than 50% of waking hours | 60 | Required occasional assistance, but is able to care for most of his/her needs. | 60 | Up and around, but minimal active play; keeps busy with quieter activities. |
| | | 50 | Requires considerable assistance and frequent medical care. | 50 | Gets dressed, but lies around much of the day; no active play, able to participate in all quiet play and activities. |
| 3 | Capable of only limited self-care, confined to bed or chair more than 50% of waking hours. | 40 | Disabled, requires special care and assistance. | 40 | Mostly in bed; participates in quiet activities. |
| | | 30 | Severely disabled, hospitalization indicated. Death not imminent. | 30 | In bed; needs assistance even for quiet play. |
| 4 | Completely disabled. Cannot carry on any self-care. Totally confined to bed or chair. | 20 | Very sick, hospitalization indicated. Death not imminent. | 20 | Often sleeping; play entirely limited to very passive activities. |
| | | 10 | Moribund, fatal processes progressing rapidly. | 10 | No play; does not get out of bed. |

*The conversion of the Lansky to ECOG scales is intended for NCI reporting purposes only.

The conversion of the Lansky to ECOG scales is intended for NCI reporting purposes only.

8) Age≥2 years. In institutional experience and according to published reports, the incidence of cGVHD in children aged less than 2 years is rare (Zecca et al. (2002) *Blood* 100:1192-1200). Daily SC injections of low-dose IL-2 have been used in pediatric post-HSCT patients as young as 2 years (Ladenstein et al. (2011) *J. Clin. Oncol.* 29:441-448). Prolonged daily SC injections of other drugs such as low molecular weight heparin and insulin are commonly administered and well tolerated in the young pediatric population with the use of the Insuflon® indwelling SC catheter;

9) The effects of IL-2 on the developing human fetus are unknown. For this reason and because chemotherapeutic agents are known to be teratogenic, participants of childbearing and child-fathering potential must agree to use adequate contraception (hormonal or barrier method of birth control; abstinence) prior to study entry and for the duration of study participation. Should a female become pregnant or suspect she is pregnant while she or her partner is participating in this study, she should inform her treating physician immediately. Males treated or enrolled on this protocol must also agree to use adequate contraception prior to the study, for the duration of study participation, and 4 months after completion of IL-2 administration; and 10) Ability to understand and/or the willingness of participant or their parent/legally authorized representative to sign a written informed consent document.

Participants are excluded according to the following exclusion criteria: 1) participants with ongoing prednisone (equivalent) dose requirement>1 mg/kg/day (or equivalent); 2) participants with concurrent use of calcineurin-inhibitor plus sirolimus (either agent alone is acceptable); 3) participants with new immunosuppressive medication, extra-corporeal photopheresis or rituximab therapy initiated in the 4 weeks prior; 4) participant with post-transplant exposure to donor lymphocyte infusion (DLI), or T-cell or IL-2 targeted medication (e.g., ATG, alemtuzumab, basiliximab, denileukin diftitox) within 100 days prior; 5) other investigational drugs within 4 weeks prior to enrollment, unless cleared by the principal investigator. Previous fixed-dose IL-2 therapy that was discontinued prior to 4 weeks is permitted; 6) participants with active malignant relapse or recrudescence of their prior hematologic disorder; 7) participants with inability to comply with IL-2 treatment regimen; 8) organ transplant (allograft) recipient; 9) HIV-positive individuals on combination antiretroviral therapy are ineligible because of the potential for pharmacokinetic interactions with the agents used after allogeneic HSCT. In addition, these individuals are at increased risk of lethal infections. Appropriate studies are undertaken in participants receiving combination antiretroviral therapy when indicated; 10) history of severe allergic reactions attributed to compounds of similar chemical or biologic composition to IL-2; 11) uncontrolled intercurrent illness including, but not limited to, ongoing or active infection, symptomatic congestive heart failure, unstable angina pectoris, cardiac arrhythmia, or psychiatric illness/social situations that would limit compliance with study requirements; 12) individuals with active uncontrolled hepatitis B or C are ineligible as they are at high risk of lethal treatment-related hepatotoxicity after HSCT; and 13) pregnant women are excluded from this study because of the potential for teratogenic or abortifacient effects. Because there is an unknown but potential risk of adverse events in nursing infants secondary to treatment of the mother, breast-feeding should be discontinued.

Subjects are treated according to the following treatment regimen:

Each participant receives daily subcutaneous IL-2 for self-administration for 8 weeks. Initial enrollment for each participant is at IL-2 dose-level A for either adult or pediatric dosing as appropriate. Each adult and pediatric participant (n=10 each) has daily SC IL-2 dose-escalated at week 2 (to dose-level B) and week 4 (to dose-level C), in the absence of DLTs or severe non-DLT AEs, and continues on MTD IL-2 for 4 weeks total, per the schema (Table 5) below. Children are expected to have increased IL-2 induced thymic Treg generation compared with adults, and consequently may require less IL-2. Serial patient PBMC samples are obtained at baseline and during IL-2 therapy to monitor the effects of treatment. Briefly, they include measurement of Treg, Tcon, CD8, B, NK and DC, as well as plasma cytokine levels (e.g., IL-2, IL-7, IL-10, IL-15). Detailed assessment of the immunologic impact of IL-2 focus on Treg and Tcon homeostasis. Aliquots of Treg-enriched product and patient PBMC undergo TCR sequencing.

TABLE 5

| Adult Cohort (n = 10) | IL-2 Dose Level (IU/m$^2$/day) |
|---|---|
| Dose-level A (starting dose) | $0.67 \times 10^6$ |
| Dose-level B | $1.35 \times 10^6$ |
| Dose-level C | $2 \times 10^6$ |
| Pediatric Cohort (n = 10) | IL-2 Dose Level (IU/m$^2$/day) |
| Dose-level A (starting dose) | $0.33 \times 10^6$ |
| Dose-level B | $0.67 \times 10^6$ |
| Dose-level C | $1 \times 10^6$ |

Prednisone (or equivalent steroid) and other cGVHD agents are continued concomitantly with IL-2, typically without dose taper. Taper of prednisone is, however, permitted at the discretion of the treating physician if deemed in the participant's interest (e.g. steroid toxicity). If prednisone must be tapered before Week 8, a 'Week 8 equivalent' cGVHD assessment is done at the time of taper to document response. Of note, progression of cGVHD prior to week 8, if during taper of other immunosuppressive therapy is not considered evidence of toxicity or lack of efficacy.

Extended-duration therapy: After completing the study period (8 week IL-2 study treatment), participants experiencing clinical benefit (complete or partial response; as well as minor response not meeting NIH criteria for partial response) with an acceptable toxicity profile are permitted to continue on extended-duration IL-2 treatment at the discretion of the treating physician. Participants are reassessed after every 6 months of extended IL-2 therapy to determine if IL-2 therapy should continue, at the discretion of the treating physician, who documents the rationale for continued IL-2 therapy.

Participants on extended-duration IL-2 therapy are evaluable for phase I toxicity endpoints. Taper of other immune suppression medications during extended-duration IL-2 are at the discretion of the treating physician. Addition of other cGVHD therapies to enhance response are permitted for participants continuing on extended-duration therapy, at the discretion of the treating physician. In the event of toxicity attributable to IL-2, dose modifications are permitted at the discretion of the treating physician. Participants are assessed on the following schedule while on extended-duration IL-2 therapy:

1) Clinic visits and labs (CBC, Creatinine, ALT, AST, Total bilirubin) for evaluation of toxicity and clinical benefit of IL-2 every 4 weeks (±2 weeks).

2) Immune assays every 8 weeks (±2 weeks) that include quantitative serum immune globulins; plasma banking; and storage of additional mononuclear cells.

3) cGVHD assessments (Section 11.1) and cGVHD symptom score sheet every 16 weeks (±4 weeks) until 1 year from the start of IL-2 treatment or the participant stops IL-2 therapy, whichever comes first.

Blood collection for research purposes in pediatric patients: For immunology studies in pediatric patients, the volume of blood collected at each blood draw does not exceed 30 ml or 3 mUkg, whichever is less. This volume is within the maximum allowable total blood draw volume for research purposes. Per institutional guidelines, blood draws for research purposes do not occur more frequently than 2 times per week. In addition, institutional guidelinesare followed for limits on the volume of blood that can be drawn for research purposes in a 28 day period, based on the weight of the patient.

The following evaluations are performed within two weeks prior to treatment for all participants: 1) medical history and documentation of the rationale for treatment of the patient's disease (including steroid dose); 2) physical examination, including vital signs, weight, performance status; 3) cGVHD assessment; 4) pregnancy test for females of childbearing potential; 5) infectious disease marker testing; 6) hematology: complete blood count (CBC) with differential; 7) serum chemistries: glucose, BUN, creatinine, total bilirubin, uric acid, alkaline phosphatase, LDH, total protein, albumin, AST, ALT, and calcium; 8) pediatric patients must have baseline creatinine clearance measured by either 24 hour urine collection or nuclear medicine glomerular filtration rate (GFR) study; 9) thyroid function tests (TSH, T4, free-T4); 10) CMV viral load; and 11) immunology: quantitative serum immune globulins; plasma banking; and storage of additional mononuclear cells.

The following evaluations are required within two weeks prior to treatment for participants with cGVHD involving specific organ systems, unless otherwise indicated: 1) ocular examination with a Schirmer's test, for participants with ocular cGVHD (optional); 2) dermatologic assessment (±biopsy for adults), for participants with cutaneous cGVHD; 3) oral examination (±biopsy for adults), for participants with oral cGVHD (optional); 4) pulmonary function tests, for participants with pulmonary manifestations of cGVHD; 5) flexion assessment of affected joints, for individuals with contractures or musculoskeletal involvement related to cGVHD; 6) evaluations during treatment (End of Week 1, 2, 3, 4, 5, 6, 8); 7) medical history and clinical examination; 8) toxicity assessment done on the same day as history and clinical examination; 9) hematology: CBC with differential; 10) serum chemistries: glucose, BUN, creatinine, uric acid, total bilirubin, alkaline phosphatase, LDH, total protein, albumin, AST, ALT, and calcium; 11) CMV viral load; 12) ommunology: quantitative immune globulins; plasma banking; and storage of additional mononuclear cells; and 13) thyroid function tests (TSH, T4, free-T4) (week 8).

For participants with cGVHD involving specific organs, the following assessments (in addition to cGVHD symptom score) are required at end of 8 weeks of study treatment, unless otherwise indicated, and at time of steroid taper (if earlier): 1) Steroid dose; 2) Ocular examination with a Schirmer's test, for participants with ocular cGVHD (optional); 3) Dermatologic assessment (±biopsy for adults), for participants with cutaneous cGVHD; 4) Oral examination (±biopsy for adults), for participants with oral cGVHD (optional); 5) Pulmonary function tests, for participants with pulmonary manifestations of cGVHD; and 6) Flexion assessment of affected joints, for individuals with contractures or musculoskeletal involvement related to cGVHD.

The following are details of IL-2 administration:

Recombinant human IL-2 (Aldesleukin) (PROLEUKIN®-Novartis Inc. & Prometheus Labs, Inc.) is supplied by Prometheus Laboratories, Inc. Recombinant human IL-2 (PROLEUKIN® (aldesleukin)) is supplied as a sterile, white to off-white, lyophilized cake in single-use vials containing 22 MIU of aldesleukin intended for intravenous (IV) administration. For the 22 million international unit (MIU) vial, when reconstituted with 1.2 mL Sterile Water for Injection (SWFI), each mL contains 18 MIU (1.1 mg) IL-2, 50 mg mannitol and ~180 mcg sodium dodecyl sulphate, buffered with ~170 mcg sodium phosphate monobasic and 890 mcg sodium phosphate dibasic to a pH of 7.5 (range: 7.2-7.8). After reconstitution, the resulting solution should be a clear, colorless to slightly yellow liquid. Reconstitution and dilution procedures other than those described may alter the deliver and/or pharmacology of IL-2 and are not recommended.

PROLEUKIN® (aldesleukin) is an unpreserved sterile product. Store vials of lyophilized IL-2 in a refrigerator at 2-8° C. (36-46° F.). Do not use beyond the expiration date printed on the label. Vials should be entered only once for reconstitution to minimize the chances of contamination. If not used immediately, in-use storage times should normally not be longer than 24 hours at 2-8° C., unless reconstitution has been performed under controlled and validated aseptic conditions in a laminar airflow hood. When reconstituted and diluted according to directions, IL-2 is stable for up to 48 hours in plastic bags (e.g., PVC bags) when stored at refrigerated and room temperatures [2-25° C. (36-77° F.)]. The reconstituted and diluted solutions should be stored in a refrigerator at 2-8° C. Do not freeze. The product should be inspected visually for particulate matter or discoloration and brought to room temperature before administration. Data support stability and sterility of reconstituted diluted IL-2 preparations (reconstituted with SWFI and further diluted with D5W); and the stability and sterility of product reconstituted with SWFI but not further diluted, for up to 14 days at 2-8° C. (36-46° F.) when single-use syringes for daily use are prepared by qualified health-care professionals under aseptic conditions (per PROLEUKIN® (aldesleukin) Investigator's Brochure (Chiron Corporation, 10 Sep. 2003, p. 113). Therefore, if reconstitution and dilution are performed under controlled and validated conditions using a laminar flow hood, the dose or doses thus prepared and stored at 2-8° C. (36-46° F.) need to be used within 14 days.

IL-2 should be reconstituted with sterile water for injection (SWFI) plus D5W. Reconstitution or dilution with Bacteriostatic Water for Injection or 0.9% Sodium Chloride for Injection should be avoided due to increased aggregates. The single-daily-use syringes containing reconstituted and diluted solutions should be stored in a refrigerator at 2-8° C. Do not freeze. The product should be inspected visually for particulate matter or discoloration and brought to room temperature before administration.

All IL-2 syringes for daily SC out-patient use should be prepared in the pharmacy at the same time, after diluting the 22 MIU IL-2 vial with 1.2 ml SWFI and 4.8 ml D5W (final IL-2 concentration=3.6 MIU/mL), and any remaining product should be immediately discarded. During reconstitution the SWFI should be directed at the sides of the vial to avoid foaming, and the contents of the vial should be gently swirled. The vial should not be shaken. After reconstitution, an up to 2-week IL-2 supply will be provided in single-use syringes (in a cool-pack if necessary), for home refrigerator storage at 2-8° C. One single-use syringe will be used each day during home SC self-administration, and discarded in the sharps' containers provided.

IL-2 may be self-administered in the home, out-patient or in-patient setting by daily subcutaneous injection. Participants will be recommended to rotate injection sites. The pharmacist (or designee under the supervision of a pharmacist) prepares the drug under aseptic conditions. The amount (in IU) of drug to be administered is determined based on body surface area (BSA). BSA is calculated based on body weight using the DuBois formula (Table 3), or an equivalent pediatric alternative. The dose should be calculated based on body weight at study entry. Subsequent dose modifications, if any, are described herein. An intravenous push or bolus are not administered. Pre-medications are not required prior to the first IL-2 dose or later doses.

TABLE 6

Body Surface Area (BSA) and Creatinine Clearance

Body surface area (BSA) should be calculated using Dubois formula that yields the following results in meters squared ($m^2$):
$BSA = (W^{0.425} \times H^{0.725}) \times 0.007184$ where the weight is in kilograms and the height is in centimeters.

Creatinine clearance (CrCl) can be calculated using the Cockroft-Gault equation as follows:

$$CrCl \text{ (ml/min)} = \frac{(140 - \text{age})(\text{actual wt in kg})}{72 \times \text{serum creatinine (mg/}dl\text{)}}$$

For females, use 85% of calculated CrCl value.
Note: In markedly obese participants, the Cockroft-Gault formula will tend to overestimate the creatinine clearance. (Adipose tissue tends to contribute little creatinine requiring renal clearance.)
For Pediatric use, alternate formulas for BSA (Mosteller) and CrCl (Schwartz) are permitted.

Antiviral, antifungal and antibacterial prophylaxis and monitoring should follow institutional practice for cGVHD management, as per the HSCT standard operating protocol (SOP). These typically include: daily acyclovir (or equivalent) for HSV prophylaxis, bactrim (or equivalent) for PCP prophylaxis, IV gammaglobulin for hypo-gammaglobulinemia, azole use for fungal prophylaxis in higher risk participants; as well as monitoring of beta-glucan and galactomannan levels in higher risk participants.

The duration of therapy is per the schema described above. In the absence of treatment delays due to adverse events, treatment may continue until one of the following criteria applies: 1) the subject withdraws consent; 2) non-compliance; 3) administrative reasons; 4) unacceptable adverse event; 5) life threatening anaphylactic reaction; 6) other grade 4 toxic event; 7) recurrent or non-resolving grade 3 toxic event; 8) severe hematologic toxicity that persists or recurs (section 6.2); 9) life threatening infection on IL-2, at the discretion of the treating physician; 10) hematologic malignancy relapse; 11) clinical worsening of GVHD requiring the addition of a new immunosuppressive medication prior to week 8, per the judgment of the treating physician. An increase in the corticosteroid dose will be considered evidence of worsening GVHD. Changes in other immunosuppressive medication doses to maintain a therapeutic level alone are not be criteria for removal; or 12) general or specific changes in the participant's condition render the participant unacceptable for further treatment in the opinion of the treating investigator.

Participants are followed for 1 year from the start of therapy, or till death, whichever occurs first. Participants removed for unacceptable adverse events are followed until resolution or stabilization of the adverse event. Participants are also asked to allow for long-term follow up so that late toxicities, should they occur, can also be identified. Follow-up (including adverse events) for participants benefiting on extended-duration therapy can continue beyond 1 year. Follow up is at DFCI if participants live locally or with their local oncology providers if they live remotely. For participants living remotely, phone calls to their local oncology providers can be made on a 6 monthly basis.

Participants are removed when any of the criteria listed applies. The reason for study removal and the date the participant was removed are documented in the study-specific case report form (CRF). Alternative care options are discussed with the participant. The reason for taking a participant off study, and the date the participant was removed, are documented in the case report form (CRF). A QACT Treatment Ended/Off Study Form is filled out when a participant is removed.

Dose delays and modifications during the 8-week IL-2 study therapy are made using the following recommendations. Toxicity assessments are done using the CTEP Version 4.0 of the NCI Common Terminology Criteria for Adverse Events (CTCAE) which is identified and located on the CTEP website on the World Wide Web at ctep.cancer.gov/protocolDevelopment/electronic_applications/ctc.htm. If possible, symptoms are managed symptomatically. In the case of toxicity, appropriate medical treatment is used (including anti-emetics, anti-diarrheals, etc.). All CTCAE grade 3 and higher adverse events experienced by participants are collected from the time of the first dose of study treatment, through the study and until the final study visit. Participants continuing to experience toxicity at the off study visit are contacted for additional assessments until the toxicity has resolved or is deemed irreversible. The dose modifications are recommended but not mandatory for participants on extended-duration IL-2.

A list of the adverse events and potential risks associated with the agents administered appear below and determine whether dose delays and modifications are made or whether the event requires expedited reporting in addition to routine reporting. IL-2 (PROLEUKIN® (aldesleukin)) is a commercial agent. The relevant side effects of low-dose IL-2 in HSCT participants are described below. Additional detailed toxicity information that relates primarily to high-dose IL-2 may be found in the PROLEUKIN® (aldesleukin) package insert.

Local Reaction: Most HSCT participants receiving SC low-dose IL-2 reported injection site reactions, typically focal erythema that resolved in a few days; and in duration that resolves after 2-3 weeks. Dose interruptions were occasionally required in participants with more marked induration (CTC grade 3). Lengthy dose interruptions may result in participants being unevaluable for response.

Constitutional symptoms: Some HSCT participants on low-dose IL-2 developed fever, nausea, fatigue and arthralgia within 72 hours of starting IL-2. Interruption of therapy resulted in symptom resolution with 3 days. Participants tolerated re-introduction of IL-2 at lower dose. Lengthy dose interruptions may result in participants being unevaluable for response.

Thyroid dysfunction: Thyroid function test abnormalities were noted in some HSCT participants on low-dose IL-2. Two participants developed clinical hypothyroidism necessitating therapy while on IL-2. After cessation of IL-2, thyroid function returned to normal. Hence, a thyroid panel (TSH, T4, free T4) levels will be checked at study entry and week 8 of study. Participants with evidence for hypothyroidism will be worked up (antimicrosomal, antithyroglobulin antibodies) and given replacement thyroxine as clinically indicated.

Hematopoiesis: Early post-HSCT, low-dose IL-2 caused an initial decrease in the absolute lymphocyte count in most participants after 1 week of therapy. Thereafter, with continued infusion, a steady increase in lymphocyte count occurred in all participants. Low dose IL-2 also caused an initial increase in eosinophil counts (peak at 3 weeks) followed by a gradual decline. No changes in monocyte or neutrophil counts were observed. The platelet count decreased by >20% in some HSCT participants on low-dose IL-2. This decrease was noted within the first 2 weeks on IL-2, and continued treatment was not associated with further declines in platelet count. No participants required platelet transfusions or had bleeding episodes. No significant impact of low-dose IL-2 on hemoglobin levels or reticulocyte counts was noted.

Thrombotic Microangiopathy (TMA): Two participants on daily SC low-dose IL-2 developed SAE of thrombotic microangiopathy (thrombocytopenia, microangiopathic hemolytic anemia with schistocytosis, renal dysfunction) that was thought possibly related to IL-2. TMA is also a known complication of calcineurin-inhibitor (CNI) and of sirolimus (both of which both the participants were on), but IL-2 may have contributed. One patient has required long-term hemodialysis. No patient subsequently developed TMA after combination CNI plus sirolimus use was disallowed.

There is toxicity related to cGVHD and to the immune suppressive medications used in its treatment. These toxicities are routinely managed by investigators. For a comprehensive list of adverse effects, refer to the package inserts of the individual immune suppressive agents.

Toxicities are to be assessed according to the NCI Common Toxicity Criteria for Adverse Events (CTCAE), Version 4.0.

Participants are removed and IL-2 therapy should be abandoned for any of the following circumstances:

Anaphylaxis: Life threatening anaphylaxis related to IL-2 requires discontinuation of IL-2, and is considered a DLT;

Thrombotic microangiopathy (TMA): TMA with CNS dysfunction, renal dysfunction requiring hemodialysis/CVVH, or need for hospitalization requires discontinuation of IL-2, and is considered a DLT;

CTC Grade 4 toxicity: Grade 4 non-hematologic toxicity related to IL-2 requires discontinuation of IL-2, and is considered a DLT, unless it solely represents an asymptomatic correctable laboratory value (e.g., uric acid);

CTC Grade 3 toxicity: IL-2 is withheld for unexpected non-hematologic toxicities that are grade 3, unless it solely represents an asymptomatic correctable laboratory value (e.g., uric acid). If the toxicity resolves to grade 1 or below within 2 weeks, IL-2 can be restarted at 50% dose (if toxicity during dose-level A) or prior lower dose level (if toxicity during dose-level B or C) that will not be re-escalated. If the toxicity does not resolve to grade 1 or below within 2 weeks, or recurs to grade 3 or above after restarting IL-2 at the lower dose, it will be discontinued, and considered a DLT;

Severe hematologic toxicity: IL-2 is withheld for severe declines in peripheral counts (ANC<500, Plts<10,000) not related to malignant disease relapse, infection or other etiologies. If counts improve (ANC>1000, Plts>20,000) within 2 weeks, IL-2 is restarted at 50% dose (if toxicity during dose-level A) or prior lower dose level (if toxicity during dose-level B or C) that will not be re-escalated. If peripheral counts do not improve within 2 weeks, or drop again (ANC<500, Plts<10,000) after restarting IL-2, IL-2 is discontinued, and considered a DLT;

Death: Treatment-related death is considered a DLT.

The following are additional considerations:

Infection: Of note, infection is not considered treatment related, since both cGVHD and concurrent immune suppression medications are known risk factors for infection. Infection is considered an expected complication of cGVHD. However, participants who develop CTC grade 3 or higher infection prior to completing week 8 of IL-2 therapy may have IL-2 withheld. If IL-2 is withheld, they can be considered for restarting IL-2 after control of infection, at the discretion of the treating physician. The IL-2 dose is: For treatment interruption≤1 week or dose-level A: restart at same dose; For treatment interruption>1 week and dose-level B or C: re-start at one dose-level below, and escalate q 2 week per schema);

Relapse: Similarly, hematologic malignancy relapse is also not considered treatment related since cGVHD patients have a known incidence of relapse. However, all cases of relapse will be documented, and will have IL-2 withheld;

Treatment Interruption: A >4 week interruption of IL-2 therapy results in the participant being considered unevaluable for response, unless objective improvement of cGVHD is documented with a shorter course of IL-2 therapy;

Expected non-hematologic toxicity: IL-2 may be withheld and/or restarted at 50% dose (if toxicity during dose-level A) or prior dose-level (if toxicity during dose-level B or C) that will not be dose-escalated, for less than CTCAE grade 3 toxicity (e.g., persistent constitutional symptoms) in the interest of patient tolerability and at the discretion of the treating physician;

Worsening of cGVHD: Worsening of GVHD during 8-week IL-2 therapy that requires addition of a new immunosuppressive medication (at the discretion of the treating physician), is a criterion for IL-2 discontinuation. An increase in the corticosteroid dose above baseline prior to week 8 is considered evidence of worsening cGVHD. Changes in other immunosuppressive medication doses to maintain a therapeutic level alone is not a criterion for discontinuation of IL-2 or considered evidence of cGHVD worsening.

The following table is a summary of data for recordation:

TABLE 7

| | Within 2 weeks prior to IL-2 | During IL-2 Therapy (End of Wks 1 2, 3, 4, 5, 6) (A) | End of Wk 8 (A) |
|---|---|---|---|
| Medical History | X | X | X |
| Physical Exam | X | X | X |
| Toxicity Assessment | | X | X |
| cGVHD Symptom Score | X | | X |
| Infectious Disease Markers | X | | |
| EKG | X | | |
| Pregnancy Test (¶) | X | | |
| Pulmonary Function | ○ | | ○ |
| Dermatologic Assessment (B) | ○ | | ○ |
| Oral Assessment | ○ | | ○ |
| Flexion Assessment | ○ | | ○ |
| Ocular Assessment | ○ | | ○ |
| CBC with Diff | X | X* | X |
| Serum Chemistry | X | X* | X |
| 24 hr CrCl or nuclear medince GFR (#) | X | | |
| Immunology (1) | X | X | X |
| Steroid Assessment (2) | X | | X |
| CMV Viral Load | X | X | X |
| Thyroid Function | X | | X |
| Drug Diary (+) | | X | X |

X—Required Evaluation
○—Required for participants with clinical involvement of these organ systems (oral and ocular assessments are optional).
(1) Immunology: quantitative immune globulins; plasma banking; storage of additional mononuclear cells
(2) Systemic steroids should not be tapered prior to week 8 unless deemed medically necessary (e.g. steroid toxicity), and if tapered early, 'week 8 equivalent' cGVHD assessments undertaken at taper, to document response
(A) Testing for weeks 1, 2, 3, 4, 5, 6, 8 will be performed ±4 days, to allow for scheduling and administrative flexibility around weekends, holidays etc.
(B) skin biopsies are optional but strongly encouraged for adult participants.
*Additional laboratory testing of CBC/manual diff, serum creatinine and LDH will also be performed 4 days (±1 day) after IL-2 initiation, to assess for anemia, thrombocytopenia, schistocytes and/or renal dysfunction associated with thrombotic microangiopathy.
(¶) For females of child-bearing potential.
(#) For pediatric patients only
(+) To be completed and returned to clinic at least every 2 weeks for the first 8 weeks of IL-2; and at least every 8 weeks for extended-duration IL-2.

Both toxicity and responses are assessed. Participants who receive IL-2 are evaluable for toxicity. Participants who have received at least 4 weeks of IL-2 are considered evaluable for lack of response. Participants undergo standardized cGVHD assessment per NIH guidelines (available on the World Wide Web at asbmt.affiniscape.com/associations/11741/files/ResponseCriteriaAPPENDIXAFormA.pdf) at baseline and week 8 on study (and at time of early steroid taper prior to week 8, if necessary) (Flipovich et al. (2005) Biol. Blood Marrow Transplant. 11:945-956). cGVHD response are assessed per NIH consensus criteria (Pavletic et al. (2006) Biol. Blood Marrow Transplant. 12:252-266). Oral and ocular sites are not be included in determination of response, as additional topical therapy is permitted for those sites. Participants have their response classified according to the following definitions:

Complete Response: Organ response: resolution of all reversible manifestations related to cGVHD in a specific organ; Overall response: resolution of all reversible manifestations in each organ or site of cGVHD involvement. Depending on relevant organ system involvement, participants undergo repeat detailed assessment of ocular, oral, cutaneous, musculoskeletal and pulmonary systems;

Partial Response: Organ response: at least 50% improvement in the scale used to measure disease manifestations related to cGVHD (e.g., a 50% decrease in skin rash from 80% BSA to 40% BSA), with a minimum of 25% improvement in the full scale as opposed solely to a percentage of the starting value (Table 8); Overall response: improvement in measure at least one organ or site, without progression in measures at any other organ or site. Of note, for global ratings and categorical scales, a 1-point change in a 3- or 7-point scale or a 2- to 3-change on a 0- to 10-point scale (0.5 SD change) is considered clinically meaningful. Additionally, the hallmark for response to therapy for bronchiolitis obliteraans syndrome (BOS) is stabilization of lung function with no further decrease in FEV1 during a 3-month period. Non-responders (e.g., minor response, stable disease) do not have changes in cGVHD meeting NIH criteria for partial response or disease progression.

mous with progressive cGVHD per NIH criteria, as participants may experience worsening symptoms that do not meet objective NIH criteria for progression. If so, they still have the option of discontinuation of IL-2 and initiating additional immunosuppression for lack of IL-2 efficacy; at the judgment of the treatment physician

TABLE 9

NYHA Classification of Heart Disease
The following table presents the New York Heart Association classification of cardiac disease.

| Class | Functional Capacity | Objective Assessment |
|---|---|---|
| I | Patients with cardiac disease but without resulting limitations of physical activity. Ordinary physical activity does not cause undue fatigue, palpitation, dyspnea, or anginal pain. | No objective evidence or cardiovascular disease. |
| II | Patients with cardiac disease resulting in slight limitation of physical activity. They are comfortable at rest. Ordinary physical activity results in fatigue, palpitation, dyspnea, or anginal pain. | Objective evidence of minimal cardiovascular disease. |
| III | Patients with cardiac disease resulting in marked limitation of physical activity. They are comfortable at rest. Less than ordinary activity causes fatigue, palpitation, dyspnea, or anginal pain. | Objective evidence of moderately severe cardiovascular disease. |
| IV | Patients with cardiac disease resulting in inability to carry on any physical activity without discomfort. Symptoms of heart failure or the anginal syndrome may be present even at rest. If any physical activity is undertaken, discomfort is increased. | Objective evidence of severe cardiovascular disease. |

Source: The Criteria Committee of New York Heart Association. Nomenclature and Criteria for Diagnosis of Diseases of the Heart and Great Vessels. 9th Ed. Boston, MA: Little, Brown & Co; 1994: 253-256.

TABLE 8 cGVHD Response Criteria
Suggested calculations for partial organ response in cGVHD. Alternatively, categorical organ-specific and global scores may be used to determine response.

| Organ and Starting Score or Value | Partial Response Criterion* |
|---|---|
| Skin (percent of body surface) | |
| >50% | e/s ≤ 0.5 and e > 0 |
| 25-50% | s − e ≥ 25 and e > 0 |
| <25% | only CR; no PR possible |
| Platelet count | e − s ≥ 100,000/uL and e < LLN |
| Gastrointestinal (and other 0-3 scales) | |
| 3 | e = 1 or 2 |
| 2 | e = 1 |
| 1 | only CR; no PR possible |
| Liver function tests (ALT, alkaline phosphatase and bilirubin) | |
| ≥3 × ULN | e/s ≤ 0.5 and e > ULN |
| <3 × ULN | only CR; no PR possible |

*s, starting score or value;
e, ending score or value;
ULN, upper limit of normal;
LLN, lower limit of normal
Examples
1. Skin: start score = 85, end score = 30; e/s = 30/85 = 0.35 = PR
2. Skin: start score = 65, end score = 45; e/s = 45/65 = 0.75 = not PR
3. Skin: start score = 45, end score = 15; s − e = 30 = PR
4. Skin: start score = 30, end score = 15; s − e = 15 = not PR Progressive Disease: Organ progression: an absolute increase of at least 25% in the scale used to measure disease manifestations related to cGVHD (Table 9). Of note, for global ratings and categorical scales, a 1-point change in a 3- or 7-point scale or a 2- to 3-change on a 0- to 10-point scale (0.5 SD change) is considered clinically meaningful. Additionally, 'clinical worsening of cGVHD' is not synony- Participants self-report symptoms and signs of cGVHD using the validated chronic GVHD Symptom Scale (Table 10). Self-reported symptom scales are obtained at baseline and end of week 8 (and at time of early steroid taper prior to week 8, if necessary).

TABLE 10 cGVHD Progression Criteria
Suggested calculations for organ proression in cGVHD

| Organ and Starting Score or Value | Progression Criterion* |
|---|---|
| Skin (percent of body surface) | e − s ≥ 25 |
| Platelet count | s − e ≥ 50,000/uL and e < LLN |
| Gastrointestinal (and other 0-3 scales) | e − s ≥ 1 |
| Liver (ALT, alkaline phosphatase and bilirubin) | |
| s ≥ 3 × ULN | e − s ≥ 3 × ULN |
| s < 3 × ULN | e − s ≥ 2 × ULN |
| Lungs (12-point Lung Function Scale)¶ | e − s ≥ 3† |

*s, starting score or value;
e, ending score or value;
ULN, upper limit of normal
¶The lung function scale is the sum of the FEV1 and DLCO (corrected for Hb) scores, each computed as: >80% of predicted = 1; 70-79% = 2; 60-69% = 3; 50-59% = 4; 40-49% = 5; <40% = 6.
†If the starting lung function score is ≥10, progression is defined as ≥5% decrease of FEV1 in two tests measured at least 2 weeks apart. This time interval is selected because these syndromes can progress rapidly.

| | Acute GVHD Staging | | |
|---|---|---|---|
| | SKIN* | LIVER¹ | GUT² |
| ORGAN STAGE | | | |
| 1 | Rash < 25% | Bilirubin 2-3 mg/dl | Diarrhea 500-999 ml/d or biopsy-proven upper GI involvement |

-continued

Acute GVHD Staging

| | SKIN* | LIVER[1] | GUT[2] |
|---|---|---|---|
| 2 | Rash 25-50% | Bilirubin 3.1-6 mg/dl | Diarrhea 1000-1499 ml/d |
| 3 | Rash > 50% | Bilirubin 6.1-15 mg/dl | Diarrhea ≥ 1500 ml/d |
| 4 | Generalized erythrodema with bullae | Bilirubin > 15 mg/dl | Severe abdominal pain with or without ileus |
| OVERALL GRADE | | | |
| I | Stage 1-2 | None | None |
| II | Stage 3 or | Stage 1 or | Stage 1 |
| III | — | Stage 2-3 or | Stage 2-4 |
| IV | Stage 4 or | Stage 4 | — |

*Use "rule of nines" to determine body surface area.
[1]Range given as total bilirubin. Downgrade by one stage if an additional cause of elevated bilirubin has been documented.
[2]Downgrade by one stage if an additional cause of diarrhea has been documented. (Adapted from Thomas et al., NEJM, 1975, pp. 895-90).

Participants have their total daily dose of corticosteroids recorded at baseline, and at the end of 8 weeks of IL-2. In the case of alternate daily dosing of corticosteroids, the average daily dose is recorded for study purposes. Participants also undergo testing for immunologic function, performed prior to start of IL-2, and at end of weeks 1, 2, 3, 4, 6, and 8. Testing includes quantitative immune globulins, plasma banking, and storage of additional mononuclear cells.

In a previous study of low dose IL2, it was observed that with a fixed dose given to a cohort of patients, despite daily IL-2 administration, the plasma IL-2 level declined after peaking at 1 week of therapy, while the Treg count rose. Further investigation revealed that Treg proliferation and activation levels also subsided after week 2. The reduction in plasma IL-2 level, believed herein to be due to its uptake and sequestration by increased high-affinity IL-2 receptors (CD25) expressed on the IL-2-expanded Treg, can reduce the subsequent availability of IL-2 to the expanded Treg, pool. Intra-patient dose escalation is believed to maximize IL-2 induced Treg enhancement in vivo and avoid tachyphylaxis due to diminution of plasma IL-2 levels after binding by increased numbers of circulating Treg with higher CD25 expression. Moreover, toxicity/DLT rate is believed to be lower with the sequential increase of dose within each patient, as a larger Treg pool would be available for IL-2 uptake and sequestration at the time of dose escalation.

As described above, three escalating doses of IL-2 are considered to determine MTD in each patient: $0.67 \times 10^6$ (dose level A), $1.35 \times 10^6$ (dose level B), and $2 \times 10^6$ IU/m²/d (dose level C) for adult patients and $0.33 \times 10^6$ (dose level A), $0.67 \times 10^6$ (dose level B), and $1 \times 10^6$ IU/m²/d (dose level C) for pediatric patients. Initial enrollment for each participant is at dose-level A. Each adult or pediatric participant is dose-escalated at week 2 (to dose-level B) and week 4 (to dose-level C), in the absence of DLTs or severe non-DLT AEs, and continues on MTD IL-2 for 4 weeks total. If a patient experiences a DLT at any dose level, the patient is removed from the study. If a patient experiences unacceptable IL-2 related AE (non-DLT) upon dose escalation, the patient can be de-escalated to the previously tolerated dose. MTD is defined as the maximum dose level in the absence of DLT in each patient. Table 11 below shows the probability of individual dose escalation under various DLT rates. For example, if the true but unknown DLT rate for an individual is 10%, then the probability of dose escalation is 90%, which is a complementary probability of DLT rate.

TABLE 11

| Probability of dose escalation in each subject | | | | | | | | | | |
|---|---|---|---|---|---|---|---|---|---|---|
| True but unknown DLT rate in each subject | 0.05 | 0.1 | 0.15 | 0.2 | 0.25 | 0.3 | 0.35 | 0.4 | 0.45 | 0.5 |
| Probability of dose escalation | 0.95 | 0.9 | 0.85 | 0.8 | 0.75 | 0.7 | 0.65 | 0.6 | 0.55 | 0.5 |

A total of 20 patients (10 adult and 10 pediatric patients) are enrolled and the feasibility of the study design are evaluated. In a previous study of IL-2 in adult patients, IL-2 at $1 \times 10^6$ IU/m²/day was determined to be MTD. With the current design of intra patient dose escalation, however, it is believed that patients experience less toxicity and thus the MTD dose level is higher. If in the 20 patients, 15 or more patients declare either dose level B or C as their MTD, the current study design is considered feasible. With this decision rule, the probability of concluding the study design feasible is 0.93 if the true but unknown feasibility rate is 85%, 0.8 if the rate is 80%, and 0.06 if the rate is 55%.

Based on prior studies, it is believed that at least 7 patients in each cohort will achieve their MTD without experiencing DLT, and the probability of observing at least 7 patients completing their MTD without DLT will be 0.88 if the true but unknown DLT rate is 0.2 and 0.65 if the rate is 0.3. In correlative studies, the relationship between IL-2 dose, plasma IL-2 level and Treg and clinical response for adult and pediatric patients, combined as well as separately, are analyzed.

Gender of subjects is not be used as a criterion for inclusion or exclusion and there are no restrictions on the accrual of minorities. In 2013, 41% of all transplanted patients were women and approximately 10% of patients were minorities. Based on this self-reported ethnicity and gender in our transplant program in 2013, the anticipated accrual in subgroups defined by gender and race is summarized in Table 12 below.

TABLE 12

Accrual Targets

|  | Sex/Gender | | |
| --- | --- | --- | --- |
|  | Females | Males | Total |
| Ethnic Category | | | |
| Hispanic or Latino | 0 + | 1 = | 2 |
| Not Hispanic or Latino | 8 + | 11 = | 18 |
| Ethnic Category: Total of all subjects | 8 (A1) + | 12 (B1) = | 20 |
| Racial Category | | | |
| American Indian or Alaskan Native | 0 + | 0 = | 0 |
| Asian | 0 + | 1 = | 1 |
| Black or African American | 0 + | 1 = | 1 |
| Native Hawaiian or other Pacific Islander | 0 + | 0 = | |
| White | 8 + | 10 = | 20 |
| Racial Category: Total of all subjects | 8 (A2) (A1 = A2) + | 12 (B2) (B1 = B2) = | 20 (C1 = C2) |

Secondary endpoints include chronic GVHD response rate by week 8, overall survival and relapse by 1 year after study entry and immunologic assessment during the 8-week treatment. Secondary endpoints are analyzed descriptively and graphically. In correlative studies, the relationship between IL-2 dose, plasma IL-2 level and Treg proliferation and activation and clinical response for adult and pediatric patients combined, as well as separately, is investigated.

Example 3: Representative Low-Dose IL-2 Therapeutic Regimen in Combination with Regulatory T-Cell Administration The following provides a representative, non-limiting embodiment of a low dose IL-2 therapeutic regimen in combination with regulatory T-cell administration. In other embodiments, the low-dose IL-2 therapeutic regimen can be replaced with the multiple-variable dose IL-2 therapeutic regimen of Example 1 and/or the methods described herein, including any combination from any Example. For example and unless otherwise stated, criteria from Example 2 can be used in full or in part with those described in Example 3 below.

Figure 8:
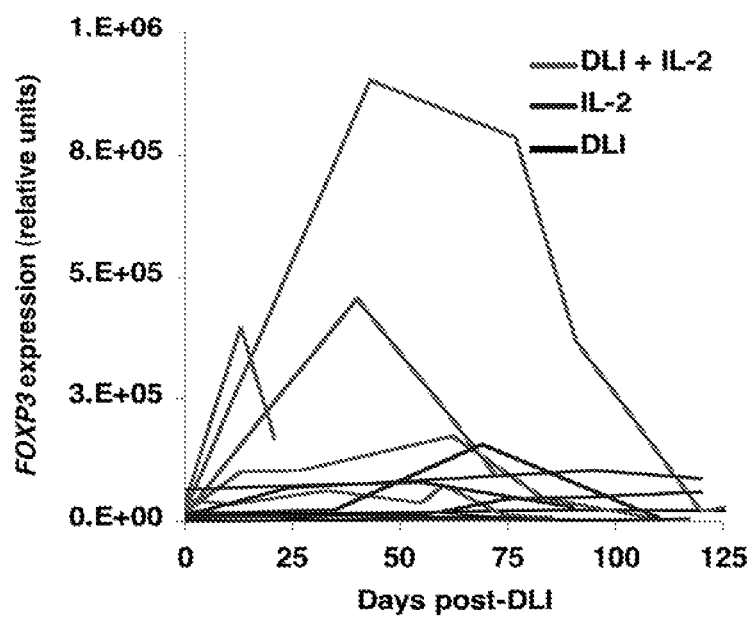
FIG. 8 shows the results of FOXP3 expression after CD4+DLI±IL-2. FOXP3 expression assessed by real time PCR in PBMC from patients who received CD4+DLI (bottom lines), low-dose IL-2 (middle lines) or CD4+DLI+low-dose IL-2 (top lines). Adapted from Zorn et al. (2009) *Biol. Blood Marrow Transplant.* 15:382-388.

Although low-dose IL-2 can preferentially augment Tregs in vivo, the durable clinical response is only ~50% of cGVHD patients. Moreover, in a trial looking for enhancement of graft-versus-leukemia (GVL) response in patients with malignant relapse post-HSCT, CD4+ enriched donor lymphocyte infusion (CLINIMACS® (cell processing platform) CD8+ depletion; dose 3-10×10$^7$ CD4+ cell/kg) plus 12-week low-dose IL-2 (0.6×10$^6$ IU/m$^2$/d) induced greater in vivo FOXP3+ Treg expansion compared to low-dose IL-2 or CD4+ enriched cell infusion alone, without inducing GVHD (Zorn et al. (2009) *Biol. Blood Marrow Transplant.* 15:382-388) (FIG. 8). Patients who received the CD4-enriched DLI concomitantly with low-dose IL-2 had greater in vivo expansion of Tregs compared to patients who received low-dose IL-2 (p=0.03) or CD4 enriched DLI alone (p=0.001) (FIG. 8). These CD4+CD25+ T cells displayed normal suppressive function and CD4 enriched DLI and IL-2 treatment was not associated with GVHD. In a trial of 28 patients who underwent CD34 selected haploidentical HSCT in Italy, peri-transplant infusion of donor Treg-enriched cells followed by donor Tcon infusion, prevented GVHD even in the absence of post-transplantation immunosuppression (Di Ianni et al. (2011) *Blood* 117:3921-3928).

Based on the results described herein, it is believed that combining low-dose IL-2 and adoptive Treg-enriched cell therapy yields additional clinical benefit. A first participant has received donor Tregs-enriched cell infusion plus low-dose IL-2 without any ill effects. Moreover, data from 5 independent leukapheresis confirms feasibility of 2-step CLINIMACS® (cell processing platform) CD8/CD19 co-depletion followed by CD25+ Treg-enrichment (Table 13. Starting from leukapheresis products with 1.6-4.07×10$^{10}$ viable total nucleated cells (TNC) comprising 6.5-9.7% CD20+B cells, 11.4-28.3% CD8+ T cells, and 5.9-16.7% CD4+CD25+CD127− Treg cells, Treg-enriched products with 0.58-1.76×10$^8$ viable TNC comprising 0-0.4% CD20+B cells, 0.01-1.2% CD8+ T cells, 83.1-92% CD4+CD25+ Treg-enriched cells and 72.8-93.9% CD4+CD25+CD127− Treg cells were achieved. Canonical FOXP3+ Treg comprised 41.3-69.6% of the product, also above the 1:2 Treg:Tcon ratio for suppression.

TABLE 13

Leukapheresis Validation

| Leukapheresis | #1 | #2 | #3 | #4 | #5 |
| --- | --- | --- | --- | --- | --- |
| Starting Product | | | | | |
| Viability | 100% | 100% | 100% | 100% | 99% |
| TNC | 2.60E+10 | 2.97E+10 | 3.16E+10 | 1.60E+10 | 4.07E+10 |
| Total CD3+ T cells | 1.51E+10 | 1.28E+10 | 6.92E+09 | 7.92E+09 | 2.47E+10 |
| CD3+ T cells/kg (100 kg recipient) | 1.51E+08 | 2.97E+08 | 3.16E+08 | 1.60E+08 | 4.07E+08 |
| % CD20+ B cells | 6.50% | 9.70% | 6.90% | 7.10% | 8.40% |
| % CD8 T cells | 28.30% | 14.40% | 11.40% | 20.80% | 23.10% |
| % CD4+ CD25+ Treg-enriched cells | 7.30% | 12.80% | 8.00% | 11.90% | 18.00% |
| % CD4+ CD25+ CD127− Treg cells | 5.9% | 6.7% | 16.7% | 5.9% | 11.4% |
| Treg-enriched Product | | | | | |
| Sterility | neg | neg | neg | neg | neg |
| Endotoxin | neg | neg | neg | neg | neg |
| Viability | 98% | 82% | 100% | 90% | 83% |
| TNC | 1.76E+08 | 5.85E+07 | 1.31E+08 | 6.51E+07 | 1.28E+08 |
| TNC/kg (100 kg recipient) | 1.76E+06 | 0.59E+06 | 1.31E+06 | 0.65E+06 | 1.28E+06 |
| TNC/kg (60 kg recipient) | 2.93E+06 | 0.98E+06 | 2.18E+06 | 1.09E+06 | 2.13E+06 |
| % CD20+ B cells | 0.10% | 0.40% | 0.10% | 0.30% | 0% |

TABLE 13-continued

| | Leukapheresis Validation | | | | |
|---|---|---|---|---|---|
| Leukapheresis | #1 | #2 | #3 | #4 | #5 |
| % CD8+ T cells | 1.20% | 0.01 | 0.20% | 0.50% | 0.10% |
| % CD4+CD25+ Treg-enriched cells | 91.90% | 91.50% | 95.50% | 83.10% | 92% |
| % CD4+CD25+CD127− Treg cells | 93.10% | 93.90% | 72.80% | 85.70% | 88.70% |

The following patient population criteria are used: 1) participants with chronic GVHD requiring systemic therapy (either extensive or limited chronic GVHD requiring systemic therapy); 2) active cGVHD despite 2 or more therapies; that includes at least 4 weeks of prednisone at a dose of ≥0.25 mg/kg/day (or equivalent); 3) no uncontrolled active infection; and 4) no malignant disease relapse.

Figure 10:
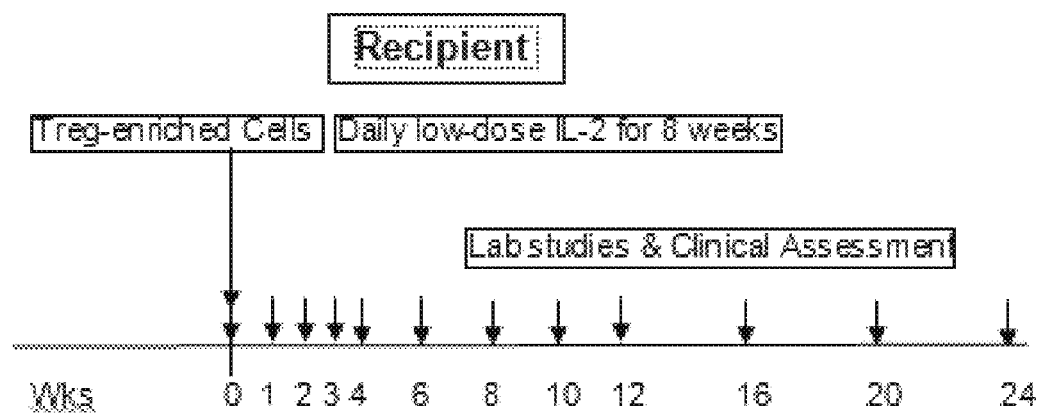
FIG. 10 shows a schematic diagram showing the Phase I dosing schedule for low-dose IL-2 therapeutic regimen in combination with regulatory T-cell administration.

Specific inclusion and exclusion criteria are detailed below:

1) Number of participants: 2-25;
2) Study design and methodology: Assess the safety and maximum tolerated dose-level (MTD) of regulatory T-cell (Treg) enriched cells plus 8-week low-dose daily interleukin-2 (IL-2) in steroid-refractory chronic graft vs host disease (cGVHD).
3) Phase I (See FIG. 10 for a schematic diagram showing the dosing schedule)

Treg-enriched cell target dose:
Dose-Level A: $0.1 \times 10^6$ cell/kg (starting dose level)
Dose-Level B: $0.3 \times 10^6$ cell/kg
Dose-Level C: $1 \times 10^6$ cell/kg Safety and efficacy analyses are as follows: The primary endpoint is the toxicity and MTD of Treg-enriched donor cell infusion plus low-dose daily SC IL-2 ($1 \times 10^6$ U/m$^2$/d). Secondary endpoints are 1) the feasibility of Treg-enriched infusion plus 8-week low-dose IL-2; 2) clinical response of Treg-enriched infusion plus 8-week low-dose IL-2; 3) immunologic effects of Treg-enriched infusion plus 8-week low-dose IL-2; and 4) predictors of clinical response.

Evaluation (by 8 weeks) is as follows: 1) assessment of feasibility of Treg-enriched cell infusion; 2) assessment of infusional toxicity of Treg-enriched cell infusion; 3) assessment of grade 3 or higher hematologic toxicity not related to malignancy; 4) assessment of grade 3 or higher non-hematologic toxicities unrelated to GVHD; 5) assessment of life-threatening infections; 6) assessment of chronic GVHD response or progression; and 7) assessment of immunologic impact.

In addition, global T cell repertoire diversity of Treg and Tcon populations in donor-derived Treg-enriched cell products and in the study patients at baseline and after 8 weeks of IL-2 treatment are assessed. The resulting sequence data can be used to track individual T cell clones across serial patient samples, enabling a following of in vivo expansion and survival of T cell clones unique to the adoptive Treg cell product during low-dose IL-2 therapy. The extent to which TCR repertoire is shared between Treg and Tcon and how it changes after combination adoptive Treg cell infusion plus low-dose IL-2 treatment as a parameter for re-establishment of Treg homeostasis is also determined.

Sample component isolation and cryopreservation: For isolation of mononuclear cells, anticoagulated samples are diluted with Hank's Balanced Salt Solution (HBSS), layered on Ficoll-Paque™ PLUS and then centrifuged at 1,000×g for 20 min at 17° C. After centrifugation, cells at the interface between ficoll and media are harvested, washed twice in HBSS and counted. Cryovials are barcode-labeled with coded CM numbers and stored in vapor phase liquid nitrogen, and location information is recorded in freezerworks. For storage of plasma, the primary anticoagulated sample is gently spun and plasma is removed prior to diluting the cell pellet with media as described above. When non-cryopreserved samples are required (e.g., whole blood for flow cytometry), samples are distributed without further processing. Samples are logged in and out in accordance with lab SOPs. Double stranded DNA (dsDNA) is isolated for TCR sequencing from between $2.5 \times 10^4$ to $10 \times 10^6$ cells using Qiagen Blood Mini and Micro columns (depending on cell amounts) using the manufacturer's recommended protocol. Samples are eluted into 100 elution buffer. Eluted dsDNA is quantified after the addition of Quant-iT™ PicoGreen™ reagent (Invitrogen), generation of a standard DNA curve, and measurement on a microplate fluorescence reader, as per the manufacturer's instructions.

Immunologic Methods: Phenotypic analysis: Immune reconstitution is evaluated by enumeration of defined lymphocyte subsets in peripheral blood. Whole blood collected with 15% EDTA is analyzed. Fluorochrome-conjugated antibodies (Beckman Coulter, BD Biosciences, Invitrogen or Miltenyi) are added to each reaction tube followed by addition of 100 μL whole blood. After 10 min incubation, 1 mL BD FACSLyse™ (cell lysis solution) is added and the sample is vortexed and incubated for 15 minutes. The antibody-labeled cells are analyzed using a BD FACSCanto® (benchtop analyzer) II flow cytometer and FACSDiva® (flow cytometry data analyzer) software. Although these assays are routinely done on fresh whole blood within 24 hours of collection, they can also be used for cryopreserved PBMC. The panel of directly conjugated reagents and fluorochromes is shown in Table 14 below. The simultaneous analysis of 7-8 colors in each tube provides a comprehensive survey of different subsets within the T, B, and NL cells with a 3-tube panel.

TABLE 14

| | | Reagent/fluorochrome panel for analysis of lymphocyte subsets | | | | | | | |
|---|---|---|---|---|---|---|---|---|---|
| Tube | Subset | FITC | PE | PE-Cy5 | PE-Cy7 | APC | APC-Cy7 | Pac Blue | Pac Orange |
| 1 | T cells/Treg | CD45RO | PD-1 | CD127 | CD25 | | CD62L | CD4 CD3 | CD8 |
| 2 | B cells | BAFF-R | IgD | CD27 | CD38 | | CD19 | CD45 CD5 | CD20 |
| 3 | NK cells | CD16 | CD56 | | CD8 | | NKG2D | CD45 CD3 | CD4 |

TABLE 14-continued

Reagent/fluorochrome panel for analysis of lymphocyte subsets

| Tube | Subset | FITC | PE | PE-Cy5 | PE-Cy7 | APC | APC-Cy7 | Pac Blue | Pac Orange |
|---|---|---|---|---|---|---|---|---|---|
| 4 | Dendritic cells | CD123 | CD141 | CD11c | LINEAGE | CD86 | CD45 | CD14 | HLA-DR |

Only 400 μL whole blood is used and 200,000 cells are analyzed in each tube. Additional tubes can be added to this standard panel to provide a more detailed analysis of specific subsets or to add markers for new subsets. The use of whole blood facilitates accurate enumeration of absolute numbers of specific cells in each sample since the variability associated with ficoll-hypaque density sedimentation cryopreservation and thawing is eliminated.

Treg and Tcon homeostasis: The analysis of Treg and Tcon subsets utilizes phenotypic and functional assays previously developed (Matsuoka et al. (2010) *J. Clin. Invest.* 120:1479-1493). The phenotypic panel of markers is summarized in Table 15 below.

TABLE 15

Multi-parameter monoclonal antibody panel for analysis of Treg and Tcon homeostasis

| Tube | V450 | Pac Orange | APC-H7 | PE-Cy7 | APC | PerCP | PE | FITC |
|---|---|---|---|---|---|---|---|---|
| 1 | CD3 | CD8 | CD4 | CD45RA | CD62L | FOXP3 | CD31 | Ki67 |
| 2 | CD3 | CD8 | CD4 | CD45RA | CD62L | FOXP3 | CD95 | BCL2 |

These assays provide a quantitative way to assess thymic genesis proliferation, and apoptosis-susceptibility of phenotypically well-defined T cell subsets. Focusing on distinct measures of T cell neogenesis (e.g., CD45RA+CD31+), proliferation (e.g., Ki-67), activation (e.g., pSTAT5), and survival (e.g., Bcl-2), they provide a detailed assessment of homeostatic balance of each T cell population. Flow-sorted cell populations are also available for in vitro functional assays (e.g., apoptosis resistance via Fas-induction assay; Tcon inhibition via CFSE dilution, thymidine incorporation, or IFN-γ assays). The internal cross-comparison of Treg and Tcon subsets in the same sample provides a unique way of assessing differential effects and responses to a common in vivo environment. Comparison of results at defined intervals identifies changes in homeostatic balance over time.

Measurement of plasma cytokines: Plasma is isolated by whole blood centrifugation at 1000×g for 15 min, and repository aliquots are stored at −70° C. ELISA is used to measure homeostatic cytokine levels at various time points. Results are correlated with flow cytometry, functional assays and clinical outcomes. Commercially available highly sensitive and reproducible kits are currently used: Human IL-2 chemiluminescent ELISA (Pierce: Product #84772); QUANTIKINE® (enzyme-linked immunosorbent assay kit) Immunoassay Human IL-7 HS (R&D: Product # HS750); and QUANTIGLO® (luminol substrate)Chemiluminescent Immunoassay Human IL-15 (R&D: Product # Q1500B). Recommended procedures are followed, including using samples in duplicate with appropriate standard dilutions and controls. Three samples of known concentration are included on each 96-well test plate to assess inter-assay precision. A Spectra 180 plate reader (Molecular Devices, Sunnyvale, Calif.) is used to measure assay results.

TCR sequence analysis: CD3+CD4+ $CD25^{med-high}CD127^{low}$ Treg and CD3+CD4+ $CD25^{neg-low}CD127^{med-high}$ Tcon from adoptive Treg-enriched cell product and from serial PBMC samples of patients at baseline and after low-dose IL-2 are analyzed. Treg and Tcon (>25,000 cells each) are purified by cell sorting based on the above immunophenotypic profile, with 400-1200 ng of extracted dsDNA plated for each sample prior to shipment for ImmunoSeq analysis.

Correlative Analyses: In exploratory statistical analyses, an association of clinical (e.g., cGVHD characteristics and/or concomitant agents) or immunologic variables measured over time (e.g., Treg count, Treg/Tcon ratio, Treg expansion pre- and post-IL-2) and treatment response is determined.

Participants are selected according to the following eligibility criteria:

1) recipient of 7-8/8 HLA-matched (HLA-A, -B, -C, -DRB1) allogeneic hematopoietic stem cell transplantation;

2) participants must have steroid-refractory cGVHD despite use of 2 or more therapies. Steroid-refractory cGVHD is defined as having persistent signs and symptoms of cGVHD (Tables 2 and 3) despite the use of prednisone at ≥0.25 mg/kg/day (or 0.5 mg/kg every other day) for at least 4 weeks (or equivalent dosing of alternate glucocorticoids) without complete resolution of signs and symptoms. Participants with either extensive chronic GVHD or limited chronic GVHD requiring systemic therapy are eligible;

3) stable dose of glucocorticoids for 4 weeks prior to enrollment;

4) no addition or subtraction of other immunosuppressive medications (e.g., calcineurin-inhibitors, sirolimus, mycophenolate-mofetil) for 4 weeks prior to enrollment. The dose of immunosuppressive medicines may be adjusted based on the therapeutic range of that drug;

5) patient age≥18 years old. Because no dosing or adverse event data are currently available on the use of IL-2 in participants<18 years of age, children are excluded from this study;

6) ECOG performance status 0-2 (Table 4);

7) Participants must have adequate organ function as defined as: a) hepatic:

adequate hepatic function (total bilirubin<2.0 mg/dl-exception permitted in participants with Gilbert's Syndrome; AST (SGOT)/ALT (SGPT)≤2×ULN), unless hepatic dysfunction is a manifestation of presumed cGVHD. For participants with abnormal LFTs as the sole manifestation of cGVHD, documented GVHD on liver biopsy will be required prior to enrollment. Abnormal LFTs in the context of active cGVHD involving other organ systems may also be permitted if the treating physician documents the abnormal LFTs as being consistent with hepatic cGVHD, and a liver biopsy will not be mandated in this situation; b) pulmonary: FEV1≥50% or DLCO(Hb)≥40% of predicted, unless pulmonary dysfunction is deemed to be due to chronic GVHD; c) renal: serum creatinine less than upper limit of normal institutional limits or creatinine clearance≥60 mL/min/1.73 m² for participants with creatinine levels above institutional normal; d) adequate bone marrow function indicated by ANC>1000/mm³ and platelets>50,000/mm³ without growth factors or transfusions; and e) cardiac: no myocardial infarction within 6 months prior to enrollment or NYHA Class III or IV heart failure, uncontrolled angina, severe uncontrolled ventricular arrhythmias, or electrocardiographic evidence of acute ischemia or active conduction system abnormalities. Prior to study entry, any ECG abnormality at screening must be documented by the investigator as not medically relevant;

8) The effects of IL-2 on the developing human fetus are unknown. For this reason and because chemotherapeutic agents are known to be teratogenic, women of child-bearing potential and men must agree to use adequate contraception (hormonal or barrier method of birth control; abstinence) prior to study entry and for the duration of study participation. Should a woman become pregnant or suspect she is pregnant while participating in this study, she should inform her treating physician immediately; and 9) Ability to understand and the willingness to sign a written informed consent document.

Participants are excluded according to the following exclusion criteria: 1) ongoing prednisone requirement>1 mg/kg/day (or equivalent); 2) concurrent use of calcineurin-inhibitor plus sirolimus (either agent alone is acceptable); 3) history of thrombotic microangiopathy, hemolytic-uremic syndrome or thrombotic thrombocytopenic purpura; 4) new chronic GVHD therapies (e.g., gleevec, extracorporeal photopheresis, rituximab, immunosuppressive medications) in the 4 weeks prior; 5) low-dose IL-2 therapy in the 4 weeks prior; 6) post-transplant exposure to T-cell or alternative IL-2 targeted medication (e.g., ATG, alemtuzumab, basiliximab, denileukin diftitox) within 100 days prior; 7) donor lymphocyte infusion within 100 days prior; 8) active malignant relapse; 9) active uncontrolled infection; 10) inability to comply with IL-2 treatment regimen; 11) organ transplant (allograft) recipient; 12) HIV-positive individuals on combination antiretroviral therapy are ineligible because of the potential for pharmacokinetic interactions with the agents used after allogeneic HSCT. In addition, these individuals are at increased risk of lethal infections. Appropriate studies is undertaken in participants receiving combination antiretroviral therapy when indicated; 13) individuals with active uncontrolled hepatitis B or C are ineligible as they are at high risk of lethal treatment-related hepatotoxicity after HSCT; 14) other investigational drugs within 4 weeks prior to enrollment, unless cleared by the principal investigator; and 15) pregnant women are excluded from this study because of the potential for teratogenic or abortifacient effects. Because there is an unknown but potential risk of adverse events in nursing infants secondary to treatment of the mother, breastfeeding should be discontinued.

Subjects are treated according to the following treatment regimen:

Donor leukapheresis: Apheresis for this study does not entail any added risk to the donor compared with usual unmodified leukapheresis. The same original hematopoietic stem cell donors will undergo apheresis to obtain donor lymphocytes. When possible, this is performed via peripheral intravenous access. Donor evaluation and apheresis may be performed at other centers (including international sites), and requires completion of appropriate consents and medical evaluations, per each donor center's standard operating procedures. All donors are assessed following Part C of 21 CFR 1271 and handled in compliance with those regulations for transplant recipients and their respective donors. Donor lymphocytes are preferably collected from a single apheresis. After apheresis, an aliquot of the product undergoes analysis to determine the baseline cell counts, viability and microbiologic/sterility testing. The products, if adequate per CMCF, are processed as detailed below and infused within 36 hours of completion of processing.

Figure 11:
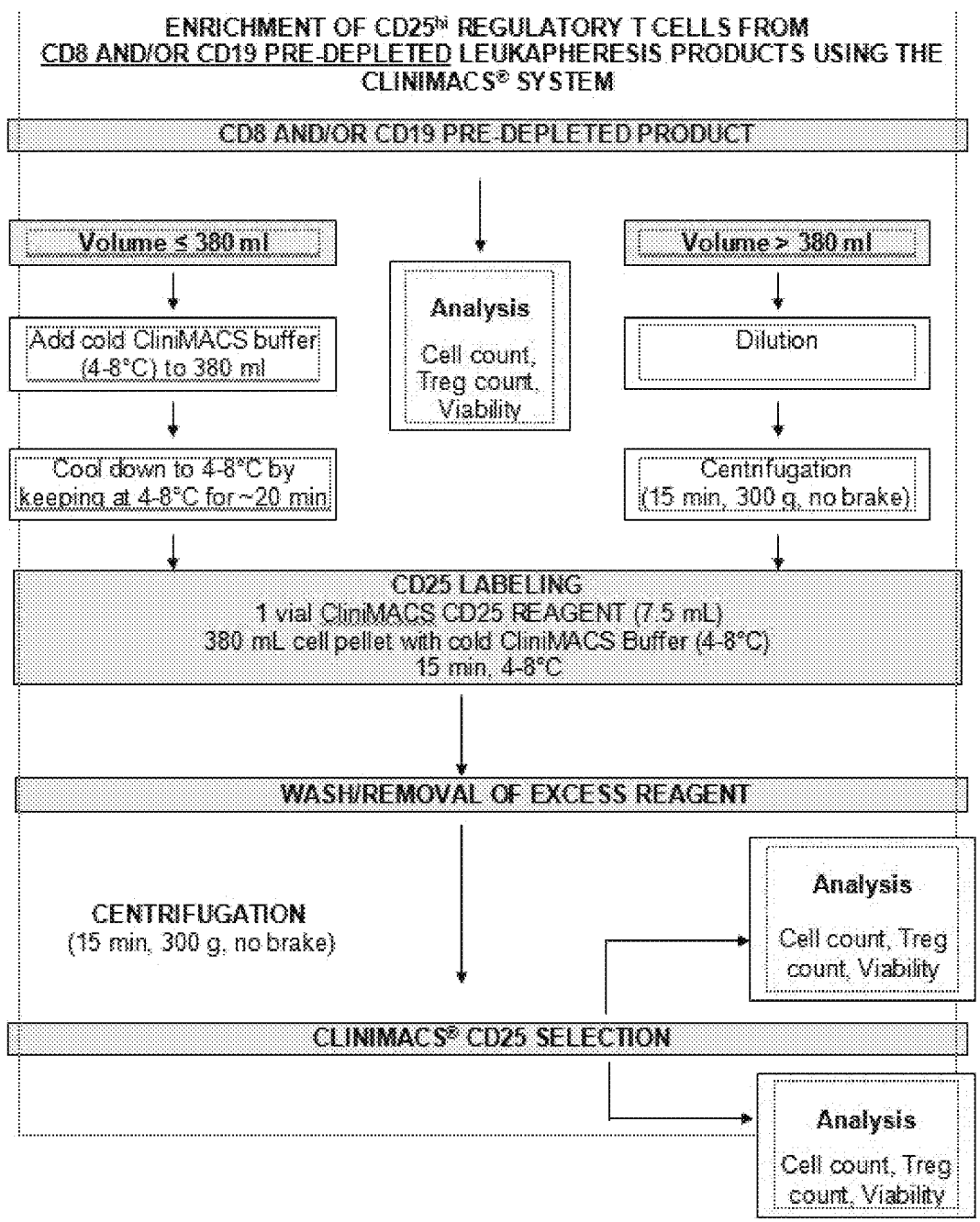
FIG. 11 shows a schematic diagram showing the enrichment of CD25+ regulatory T cells from CD8 and/or CD19 pre-depleted leukapheresis products using the CLINIMACS® system.

Study therapy: Treg-enriched Cell Product: Upon receipt of donor leukapheresis product, it undergoes sequential 2-step Treg-cell enrichment using clinical-grade CLINIMACS® (cell processing platform) Reagent System according to manufacturer's instructions (Miltenyi Biotec): i) CD8+/CD19+co-depletion (2.1 depletion program, CLINIMACS® (cell processing platform)); followed by ii) CD25+ positive selection (3.1 enrichment program, CLINIMACS® (cell processing platform)). The detailed protocol for the preparation and use of the CLINIMACS® (cell processing platform) reagent system is as per the CLINIMACS® (cell processing platform) User Manual (FIG. 11). For example, prior stem cell donors for a subject can undergo apheresis to obtain donor lymphocytes for the subject. The products, if adequate (minimum dose≥3×10⁷ CD3+ cells/kg), are processed as described below and infused within the stated product expiration time. Upon receipt of donor leukapheresis product, it undergoes sequential 2-step Treg-cell enrichment with CD8+/CD19+co-depletion followed by CD25+ positive selection using clinical-grade CLINIMACS® (cell processing platform) Reagent System according to manufacturer's instructions (Miltenyi Biotec). Samples removed prior to processing and after completion of the Treg-enrichment are used to determine cell viability and enumerate CD3+, CD4+, CD8+, CD25+, CD127+, and FoxP3+ cells. The product is denoted as "Treg-enriched cells". Release criteria include: >70% cell viability, negative gram stain; ≥90% CD4+CD25+; and ≥50% FoxP3+ cells in the product.

Cell Product Evaluation: Samples are removed prior to processing and after completion of the Treg-enrichment. These are used to determine cell viability and enumerate CD3+, CD4+, CD8+, CD25+, CD127+, and FOXP3+ cells (in combination as necessary, e.g. CD4+CD25+FOXP3+ cells) before and/or after processing. Gram stain, endotoxin and sterility testing are also performed. The product is denoted as 'Treg-enriched cells'. Release criteria include: >70% cell viability by trypan blue, negative gram stain/endotoxin, ≥70% CD4+CD25+ and >50% CD4+CD25+CD127− cells in the product (Table 16).

TABLE 16

| A. Post-ClinMACS selection/Pre-infusion tests for release criteria | | | |
|---|---|---|---|
| Samples | Test Performed | Test Facility | Release Criteria |
| Post-selection/Pre-infusion | Total Cell Dose* | CMCF | Dose A: 0.1 × 10⁶ cells/kg (start level)<br>Dose B: 0.3 × 10⁶ cells/kg<br>Dose C: 1 × 10⁶ cells/kg |

TABLE 16-continued

| | | |
|---|---|---|
| Cell Viability | CMCF | ≥70% by trypan blue |
| Gram Stain | CMCF | No organisms |
| Endotoxin | CMCF | <5 EU/ml |
| Immuno-phenotyping | CMCF | ≥70% CD4+CD25+ cells |
| Immuno-phenotyping | CMCF | ≥50% CD25+CD127− cells |

*target dose, however product with lower cell dose can also be infused.

B. Post-infusion tests for documentation

| Samples | Test Performed | Test Facility | Criteria |
|---|---|---|---|
| Post-infusion | Sterility | CMCF | No growth for 14 days |

| Assay | Pre-processing | Treg-enriched Product | Release Criteria |
|---|---|---|---|
| Gram Stain | | X | X |
| Endotoxin | | X | X |
| Total Nucleated Cells | X | X | X* |
| Immuno-phenotyping | X | X | X* |
| Viability | X | X | X |
| Sterility | X | X | |

*Required to determine CD3, CD4, CD25, CD127 count

Of note, the target Treg-enriched cell dose/kg is not a release criterion. Product is infused even if the cell dose/kg is below target at the maximum number of cells available after requisite QC samples obtained.

Treg-enriched Cell Dose: Participants are targeted to a defined dose of donor Treg-enriched total nucleated cells. Initial enrollment is at target dose-level A. Subsequent cohorts will be dose escalated per the schema below

| Cohort | Treg-enriched Cell Dose (Viable Cells/kg*) |
|---|---|
| Dose-level A (starting dose) | $0.1 \times 10^6$ |
| Dose-level B | $0.3 \times 10^6$ |
| Dose-level C | $1 \times 10^6$ |

*Recipient weight

This is a phase I dose-finding design: 5 participants accrue at a given dose-level (with a mandatory 28 day hiatus after the initial 4 participants accrued). If ≤1 of 5 has a DLT by Day 28, then a dose escalation takes place. If this is dose-level C, then this dose is the MTD. If ≥2 participants in a cohort experience DLT, then the MTD is considered exceeded. If this is dose-level A, accrual stops. If this is dose-level B, then dose-level A is the MTD. If this is dose-level C, then dose-level B is the MTD. A further 10 participants is then accrued at presumptive MTD to further assess toxicity and efficacy.

Treg-enriched Cell Infusion: The CLINIMACS® (cell processing platform) cell product is not be administered until it has passed the release criteria (Table 16). If release criteria are not met, the product is not infused, and the patient is not unevaluable for DLT assessment, but product is assessable for feasibility. The feasibility of generating a suitable Treg-enriched product is determined as described herein.

Once release criteria have been met, the product is infused into the recipient through a central or peripheral venous catheter. The cells are infused over ~5-10 minutes through an intravenous catheter. TYLENOL® (acetaminophen) 650 mg PO and BENADRYL® (diphenhydramine) 25 mg IV premedication are usual (but not required) prior to the infusion. Participants are monitored for development of infusion reactions for ~1 hour after the end of the infusion.

Aliquots of Treg-enriched cells in excess of dose infused are utilized for phenotypic, functional, and/or DNA, RNA, and protein studies. Any remaining Treg-enriched cells are cryopreserved per standard operating procedure for future quality control use and correlative analysis.

Interleukin-2: Starting the day of Treg-enriched cell infusion, each participant receives daily subcutaneous IL-2 for self-administration for 8 weeks, followed by a 4-week hiatus (unless a multiple-variable dose IL-2 regimen according to the methods of the present invention are applied). IL-2 is administered on an outpatient basis. Expected toxicities and potential risks as well as dose modifications are described in Example 2

Prednisone (or equivalent steroid) and other agents are continued concomitantly with IL-2 without dose modification. Taper of prednisone is not be permitted during the initial 6 weeks of the study, but can be reduced thereafter in responders (after documentation of response per NIH cGVHD criteria) at the discretion of the treating physician (e.g., steroid toxicity). Of note, clinically stable cGVHD during taper of other immune suppression medications is considered evidence of efficacy; and progression of cGVHD during taper of other immunosuppressive therapy is not considered evidence of toxicity or lack of efficacy.

Extended-duration therapy: After completing study period (8 week IL-2 study treatment and 4 weeks off IL-2), participants experiencing clinical benefit (complete or partial response; as well as minor response not meeting NIH criteria for partial response) with an acceptable toxicity profile are permitted to continue on extended-duration IL-2 treatment at the discretion of the treating physician. Participants are reassessed after every 6 months of extended IL-2 therapy to determine if IL-2 therapy should continue, at the discretion of the treating physician, who documents the rationale for continued IL-2 therapy.

Participants on extended-duration IL-2 therapy are not be evaluable for phase I toxicity endpoints (e.g., for cell dose escalation/de-escalation purposes). Taper of other immune suppression medications during extended-duration IL-2 is at the discretion of the treating physician. Addition of other cGVHD therapies to enhance response is permitted for participants continuing on extended-duration therapy, at the discretion of the treating physician. In the event of toxicity attributable to IL-2, dose modifications per guidelines are permitted, at the discretion of the treating physician. Participants are assessed on the following suggested schedule while on extended-duration IL-2 therapy: 1) clinic visits and labs (CBC, Creatinine, ALT, AST, Total bilirubin) for evaluation of toxicity and clinical benefit of IL-2 every 4 weeks (±2 weeks); 2) immune assays every 8 weeks (±2 weeks) that include quantitative serum immune globulins; plasma banking; and storage of additional mononuclear cells; and 3) cGVHD Assessments and cGVHD symptom score sheet every 16 weeks (±4 weeks) until 1 year from the start of IL-2 treatment or the participant stops IL-2 therapy, whichever comes first.

The following evaluations are performed within two weeks prior to treatment for all participants: 1) medical history and documentation of the rationale for treatment of the patient's disease (including steroid dose); 2) physical examination, including vital signs, weight, performance status; 3) cGVHD assessment; 4) pregnancy test for women of childbearing potential; 5) infectious disease marker testing; 6) pulmonary function test (within 4 weeks prior); 7) hematology: complete blood count (CBC) with differential; 8) serum chemistries: glucose, BUN, creatinine, uric acid, total bilirubin, alkaline phosphatase, LDH, total protein, albumin, AST, ALT, and calcium; 9) thyroid function tests (TSH, T4, free-T4); 10) CMV viral load; and 11) immunology: quantitative serum immune globulins; plasma banking; and storage of additional mononuclear cells.

The following evaluations are required within two weeks prior to treatment for participants with cGVHD involving specific organ systems, unless otherwise indicated: 1) ocular examination with a Schirmer's test, for participants with ocular cGVHD (optional); 2) dermatologic assessment, for participants with cutaneous cGVHD; 3) oral examination (±biopsy), for participants with oral cGVHD (optional); and 4) flexion assessment of affected joints, for individuals with contractures or musculoskeletal involvement related to cGVHD.

Evaluations during treatment (End of Weeks 1, 2, 3, 4, 6, 8), off-IL-2 (End of Weeks 10, 12), and extended observation (End of Weeks 16, 20, 24) include: 1) medical history and clinical examination; 2) toxicity assessment done on the same day as history and clinical examination; 3) hematology: CBC with differential; 4) serum chemistries: glucose, BUN, creatinine, uric acid, total bilirubin, alkaline phosphatase, LDH, total protein, albumin, AST, ALT, and calcium.; 5) CMV viral load; 6) immunology: quantitative immune globulins; plasma banking; and storage of additional mononuclear cells; and 7) thyroid function tests (TSH, T4, free-T4) (week 8, 16, 24).

For participants with cGVHD involving specific organs, the following assessments (in addition to cGVHD symptom score) are required at end of 8 weeks of study treatment, unless otherwise indicated, and at time of steroid taper (if earlier): 1) steroid dose; 2) ocular examination with a Schirmer's test, for participants with ocular cGVHD (optional); 3) dermatologic assessment, for participants with cutaneous cGVHD; 4) oral examination (±biopsy), for participants with oral cGVHD (optional); 5) pulmonary function tests, for participants with pulmonary manifestations of cGVHD; and 6) flexion assessment of affected joints, for individuals with contractures or musculoskeletal involvement related to cGVHD.

Adverse event lists for Treg-enriched cell infusion: Unselected donor lymphocyte infusion for treatment of malignant disease relapse has been associated with Tcon-mediated GVHD flare, and with myelosuppression primarily in cases of significant leukemia/lymphoma involving the bone marrow. However, Treg are dominant suppressors of Tcon, and the CLINIMACS® (cell processing platform) Treg-enriched product is suppressive in vitro even at Treg:Tcon ratio of 1:2, with no toxicities reported after infusion of up to $4\times10^6$ cell/kg in HSCT recipients without active GVHD or malignant disease relapse (Di Ianni et al. (2011) *Blood* 117:3921-3928). Infusion of Treg-enriched product at a starting dose-level of $0.5\times10^6$ cells/kg containing ≥50% CD4+CD25+ CD127− Treg (above the 1:2 Treg:Tcon ratio of suppressive effect) is therefore believed to be safe. GVHD progression and myelosuppression are monitored to confirm safety of Treg-enriched cell infusion in active cGVHD.

The following table is a summary of data for recordation:

TABLE 17

| | Within 2 weeks prior to IL-2 | During IL-2 Therapy (End of Wks 1, 2, 3, 4, 6) [a] | End of Wk 8 [a] | End of Wk 10, 12 [a] | End of Wk 16, 20, 24 [b] |
|---|---|---|---|---|---|
| Medical History | X | X | X | X | X |
| Physical Exam | X | X | X | X | X |
| Toxicity Assessment | | X | X | X | X |
| cGVHD Symptom Score | X | | X | X | |
| Infectious Disease Markers | X | | | | |
| EKG | X | | | | |
| Pregnancy Test[¶] | X | | | | |
| Pulmonary Function | X[d] | | ○ | | |
| Dermatologic Assessment | ○ | | ○ | | |
| Oral Assessment | ○ | | ○ | | |
| Flexion Assessment | ○ | | ○ | | |
| Ocular Assessment | ○ | | ○ | | |
| CBC with Diff | X | X* | X | X | X |
| Serum Chemistry | X | X* | X | X | X |
| Immunology[1] | X | X | X | X | X |
| Steroid Assessment[2] | X | | X | | |
| CMV Viral Load | X | X | X | X | X |
| Thyroid Function | X | | X | | X[c] |
| Drug Diary[+] | | X | X | | |

X—Required Evaluation
○—Required for participants with clinical involvement of these organ systems
[1]Immunology: quantitative immune globulins; plasma banking; storage of additional mononuclear cells
[2] Systemic steroids should not be tapered prior to week 8 unless medically necessary (e.g. steroid toxicity), and if tapered early, 'week 8 equivalent' cGVHD assessments undertaken to document response
[a]Testing on weeks 1, 2, 3, 4, 6, 8, 10, 12 will be performed ±4 days, to allow for scheduling and administrative flexibility around weekends, holidays etc.
[b] Testing on weeks 16, 20, 24 will be performed ±7 days, for scheduling and administrative flexibility. For participants receiving extended-duration IL-2, please also refer to the relevant protocol section for additional follow up requirements.
[c]Weeks 16, 24
[d]Testing can be scheduled up to 4 weeks prior, to allow for scheduling flexibility
*Additional laboratory testing of CBC/manual diff, serum creatinine and LDH will also be performed 4 days (+/−1 day) after IL-2 initiation, to assess for anemia, thrombocytopenia, schistocytes and/or renal dysfunction associated with thrombotic microangiopathy.
[¶]For women of child-bearing potential.
[+]To be completed and returned to clinic at least every 2 weeks for the first 8 weeks of IL-2; and at least every 8 weeks for extended-duration IL-2.

Both toxicity and responses are assessed. Participants who receive Treg-enriched cell infusion are evaluable for toxicity. Participants who have received Treg-enriched cell infusion plus at least 6 weeks of IL-2 are considered evaluable for lack of response. These participants have their response classified according to definitions stated herein. For example and in addition to definitions in Example 2, Chronic GVHD Symptom Score refers to participants self-reports symptoms and signs of cGVHD using the validated chronic GVHD Symptom Scale. Self-Reported symptom Scales are obtained at baseline and end of weeks 8, 10, 12

(and at time of early steroid taper prior to week 8, if necessary). Steroid Use for Chronic GVHD refers to participants having their total daily dose of corticosteroids recorded at baseline, and at end of 8 weeks of IL-2. In the case of alternate daily dosing of corticosteroids, the average daily dose will be recorded for study purposes. Immune Assessment refers to participants undergoing testing for immunologic function, performed prior to start of IL-2, and at end of weeks 1, 2, 3, 4, 6, 8, 10, 12, 16 and 24. Testing includes quantitative immune globulins, plasma banking, and storage of additional mononuclear cells.

The primary endpoint of this phase I study is to determine the MTD of Treg-enriched cells given in conjunction with $1 \times 10^6$ $IU/m^2$/day subcutaneous IL-2 to participants who have steroid-refractory chronic GVHD requiring systemic therapy. MTD is assessed after 8 weeks of IL2 treatment, by DLT. Three escalating doses of Treg-enriched cells are considered to determine the MTD: $0.1 \times 10^6$ cells/kg (Dose-level A); $0.3 \times 10^6$ cells/kg (dose-level B); $1 \times 10^6$ cells/kg (dose-level C). A dose of up to $4 \times 10^6$ Treg-enriched cells/kg was well tolerated per the literature, but $0.1 \times 10^6$ Treg-enriched cells/kg will be the initial dose-level in this study to provide an analysis buffer. A cohort of 5 evaluable participants who receive product meeting the release criteria enter at each target dose level (with a 28 day hiatus after the initial 4 participants are accrued). Participants are considered unevaluable for the determination of MTD if they require early removal from the study without developing a DLT. Additional participants are enrolled at a specific dose cohort to substitute for any participants within the cohort who are removed from the study. If ≤1 DLTs are observed within a cohort of 5 participants, then a dose escalation takes place. If this is Dose level C, this dose is the MTD. If ≥2 DLTs are observed in a cohort, then the MTD is considered exceeded. If this is Dose level A, accrual stops. If this is Dose level B, then Dose level A is the MTD. If this is Dose level C, then Dose level B is the MTD.

With this design, the probability of dose escalation is 0.92 if the true but unknown rate of DLT is 10%; 0.74 if the rate is 20%, but 0.34 if the rate is 40%. Table 18 below provides the operating characteristics of dose escalation.

TABLE 18

Operating Characteristics

| True but Unknown DLT Rate | 10% | 20% | 30% | 40% | 50% | 60% |
|---|---|---|---|---|---|---|
| Probability of Dose Escalation (≤1 in 5) | 0.92 | 0.74 | 0.53 | 0.34 | 0.19 | 0.09 |

Once the MTD is established, an additional 10 evaluable participants are treated at the MTD. With 10 evaluable participants, the maximum width of 90% confidence interval for toxicity is within ±28%. The sample size will approximately range from 2-25 evaluable participants, depending on the number of dose levels tested.

Secondary endpoints are also analyzed. For example, CLINIMACS® (cell processing platform) assessment is performed. The feasibility of achieving a successful Treg-enriched infusion product using the CLINIMACS® (cell processing platform) device is assessed. Leukapheresis product is considered eligible for determination of feasibility of CLINIMACS® (cell processing platform) selection if it contains ≥70% cell viability, negative microbiology. Infused CLINIMACS® (cell processing platform) product contains ≥70% cell viability, negative gram stain/endotoxin, ≥70% CD4+CD25+ cells and ≥50% CD4+CD25+CD127− Treg after processing, and is eligible for MTD assessment. The CLINIMACS® (cell processing platform) system is considered feasible if the rate of eligible products for the determination of MTD (feasibility rate) is 80% or higher and infeasible if 50% or lower. In the first 10 products, if 6 or fewer products meet these criteria, the system is considered infeasible. Conversely, if ≥7 in the first 10 products meet the criteria, the study proceeds. With this decision rule, the probability of stopping early is 0.83 if the true but unknown feasibility rate is 50% and 0.12 if the rate is 80%. The feasibility of manufacturing Treg-enriched product meeting the targeted cell dose-level is also assessed. If the actual achieved cell doses are lower than the targeted dose-level, the actual cell doses administered inform the presumptive MTD chosen for the 10 patient expanded cohort.

Secondary endpoints also include clinical response, as summarized by simple descriptive summary statistics delineating complete and partial response, stable and progressive disease, as well as immunologic effects of Treg-enriched infusion plus 8-week low-dose IL-2. Secondary endpoints are primarily analyzed descriptively and graphically. In particular, the immunologic effects of Treg-enriched infusion plus 8-week low-dose IL-2 on B cells, NK, cells, or dendritic cells, both in terms of pre and post treatment changes in cell numbers and cytokine production are characterized. In addition, if the sample size permits, clinical (patient and transplant-related) and biological (e.g. numbers of Treg, Tcon, Treg:Tcon ratio and Treg function) predictors of response are explored.

Responses are also monitored. Participants who receive at least 6 weeks of IL-2 are evaluable for lack of response, even if there are major protocol treatment deviations or if they are ineligible. Each participant is assigned one of the following categories: 1) complete cGVHD response per NIH criteria, 2) partial cGVHD response per NIH criteria, 3) non-response (includes stable disease) per NIH criteria, 4) progressive cGVHD per NIH criteria, 5) malignant disease relapse, 6) early death from toxicity, 7) early death because of other cause, or 9) unknown (not assessable, insufficient data). By arbitrary convention, category 9 usually designates the "unknown" status of any type of data in a clinical database.

Toxicity is also monitored. All participants who receive Treg-enriched cell product are evaluable for toxicity. Progression of cGVHD (per NIH criteria) is considered a DLT. In a previous study, no patient experienced cGVHD progression during 8-week IL-2 such that they needed additional therapy or increased steroids per the judgment of the treating physician. Participants are also assessed for malignant disease relapse and infection.

Example 4: Representative Low-Dose IL-2 Therapeutic Regimen in Combination with Extra-Corporeal Photopheresis (ECP)

The following provides a representative, non-limiting embodiment of a low dose IL-2 therapeutic regimen in combination with ECP. In other embodiments, the low-dose IL-2 therapeutic regimen can be replaced with the multiple-variable dose IL-2 therapeutic regimen of Example 1 and/or the methods described herein, including any combination from any Example. For example and unless otherwise stated, criteria from Example 2 can be used in full or in part with those described in Example 4 below.

The most common indication for ECP is glucocorticoid-refractory cGVHD after allogeneic HSCT. Initial studies in mouse models of acute GVHD indicate that the therapeutic mechanism of ECP is dependent on CD4+CD25+FOXP3+ regulatory T cells ($T_{reg}$), which act to control auto- and alloimmune responses mediated by conventional T cells ($T_{con}$). However, human data in support of the ECP $T_{reg}$ hypothesis are scant. In parallel, human trials of low-dose interleukin-2 (IL-2) for glucocorticoid-refractory cGVHD show clinical responses alongside in vivo increases in $T_{reg}$ number and function. However, half of treated patients do not have a clinical response and taper of immune suppressants during extended ECP is slow and often incomplete (Dignan et al. (2012) Br. J. Haematol. 58:62-78; Flowers et al. (2008) Blood 112:2667-2674). There are no studies in ECP patients that 1) report quantitative Treg and DC subset data, 2) report relevant cytokine changes, or 3) correlate any of these changes with ECP dose or degree of lymphocyte apoptosis. Both ECP and low-dose IL-2 have measurable clinical efficacy in cGVHD.

Based on the results described herein, the combined intervention strategy is believed to significantly modulate $T_{reg}$ expansion in order to better suppress cGVHD, as well as other conditions in which suppression of immune responses is desired. IL-2 delivers a proliferative and survival signal to Treg both in vitro and in vivo.

Indeed, 4 subjects have already received IL-2 and ECP as described herein for refractory cutaneous cGVHD with no side effects. All had objective cGVHD responses at 3 months with increased skin suppleness and all elected to continue IL-2 and ECP. Importantly, 2 of 2 subjects tested had an in vivo Treg rise with IL-2 and ECP compared to monotherapy. One patient with a PR to IL-2 initiated ECP during extended IL-2 therapy, with enhanced cGVHD clinical response and a 1.7-fold rise in Treg compared to IL-2 alone. In another patient with inadequate response to ECP, the addition of low-dose IL-2 induced cGVHD response along with a 33-fold rise in Treg compared to ECP alone.

The study is expanded to a a 16 week trial of twice-weekly ECP in weeks 1-16, with the sequential addition of daily low-dose IL-2 dosed at $1 \times 10^6$ IU/m²/day during weeks 8-16, with the goal of optimizing ECP treatment for cGVHD. In some embodiments, the study is a 12 week study in which patients with steroid refractory cGVHD will receive ECP for weeks 1-12, with the sequential addition of low-dose IL-2 for weeks 6-12.

The following patient population criteria are used: 1) patients with cGVHD requiring systemic therapy. Patients with either extensive cGVHD or limited cGVHD requiring systemic therapy are eligible; and 2) inadequate response to at least 4 weeks of prednisone at a dose of ≥0.25 mg/kg/day (or equivalent).

Figure 12:
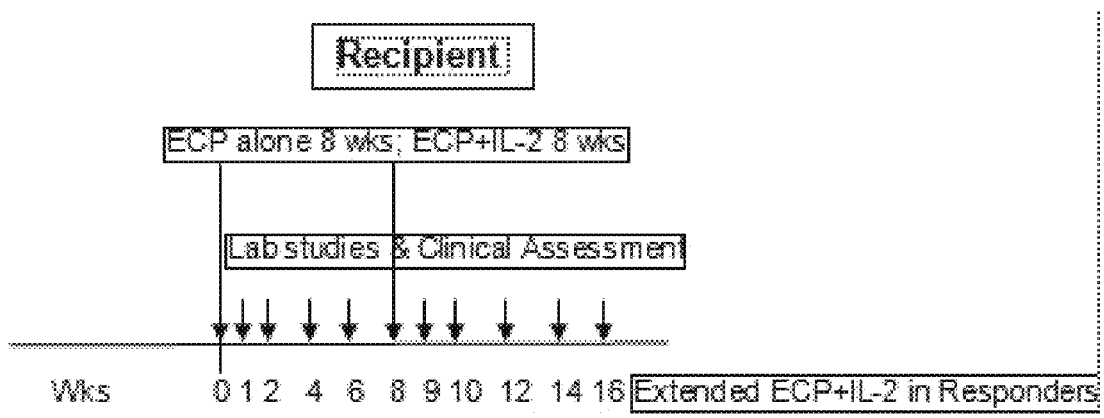
FIG. 12 shows a schematic diagram showing Phase II dosing schedule for low-dose IL-2 therapeutic regimen in combination with extra-corporeal photopheresis (ECP).

Specific inclusion and exclusion criteria are detailed below:
1) Number of participants: 25-34;
2) Study design and methodology:
Phase II (See FIG. 12 for a schematic diagram showing the dosing schedule)
Safety and efficacy analyses are as follows: The primary endpoint is determining the overall clinical response rate of ECP plus low-dose daily SC IL-2 in steroid-refractory cGVHD. For example, overall cGVHD response rate at week 16, toxicity of 8 week daily IL-2 added to ECP, immunologic effects of ECP plus low-dose IL-2, prednisone use during ECP plus low-dose IL-2, and overall and progression-free survival, non-relapse mortality, and relapse at 1 year after study entry, can be assessed. Secondary endpoints are 1) determining toxicity of ECP plus low-dose SC IL-2 therapy; 2) assessing the immunologic effects of ECP plus low-dose daily SC IL-2; 3) determining ongoing prednisone use with ECP plus low-dose IL-2 therapy; and 4) assessing overall survival, progression-free survival, non-relapse mortality and relapse at 1 year after start of ECP plus low-dose IL-2.

Participants are selected according to the following eligibility criteria:
1) recipients of 7-8/8 HLA matched adult donor allogeneic stem cell transplantation with myeloablative or non-myeloablative conditioning regimens;
2) participants must have steroid-refractory cGVHD. Steroid-refractory cGVHD is defined as having persistent signs and symptoms of cGVHD (Tables 2 and 3) despite the use of prednisone at ≥0.25 mg/kg/day (or 0.5 mg/kg every other day) for at least 4 weeks (or equivalent dosing of alternate corticosteroids) without complete resolution of signs and symptoms. Patients with either extensive chronic GVHD or limited chronic GVHD requiring systemic therapy are eligible;
3) stable dose of corticosteroids for 4 weeks prior to enrollment;
4) no addition or subtraction of other immunosuppressive medications (e.g., calcineurin-inhibitors, sirolimus, mycophenolate-mofetil) for 4 weeks prior to enrollment. The dose of immunosuppressive medicines may be adjusted based on the therapeutic range of that drug;
5) patient age≥18 years old. Because no dosing or adverse event data are currently available on the use of IL-2 in participants<18 years of age, children are excluded from this study;
6) estimated life expectancy greater than 3 months;
7) ECOG performance status 0-2 (Table 4);
8) Participants must have adequate organ function as defined as: a) hepatic: adequate hepatic function (total bilirubin<2.0 mg/dl-exception permitted in patients with Gilbert's Syndrome; AST (SGOT)/ALT (SGPT)≤2×ULN), unless hepatic dysfunction is a manifestation of presumed cGVHD. For patients with abnormal LFTs as the sole manifestation of cGVHD, documented GVHD on liver biopsy will be required prior to enrollment. Abnormal LFTs in the context of active cGVHD involving other organ systems may also be permitted if the treating physician documents the abnormal LFTs as being consistent with hepatic cGVHD, and a liver biopsy will not be mandated in this situation; b) renal: serum creatinine within normal institutional limits or creatinine clearance>60 mL/min/1.73 m² for participants with creatinine levels above institutional normal; c) adequate bone marrow function indicated by ANC>1000/mm³ and platelets>50,000/mm³ without growth factors or transfusions; and d) cardiac: no myocardial infarction within 6 months prior to enrollment or NYHA Class III or IV heart failure, uncontrolled angina, severe uncontrolled ventricular arrhythmias, or electrocardiographic evidence of acute ischemia or active conduction system abnormalities. Prior to study entry, any ECG abnormality at screening must be documented by the investigator as not medically relevant;
9) The effects of IL-2 on the developing human fetus are unknown. For this reason and because chemotherapeutic agents are known to be teratogenic, women of child-bearing potential and men must agree to use adequate contraception (hormonal or barrier method of birth control; abstinence)

prior to study entry and for the duration of study participation. Should a woman become pregnant or suspect she is pregnant while participating in this study, she should inform her treating physician immediately; and 10) ability to understand and the willingness to sign a written informed consent document.

Participants are excluded according to the following exclusion criteria: 1) ongoing prednisone requirement>1 mg/kg/day (or equivalent); 2) concurrent use of calcineurin-inhibitors plus sirolimus. Either agent alone is acceptable; 3) history of thrombotic microangiopathy, hemolytic-uremic syndrome or thrombotic thrombocytopenic purpura; 4) exposure to any new immunosuppressive medication in the 4 weeks prior to enrollment; 5) extra-corporeal photopheresis (ECP) or rituximab therapy within 4 weeks prior to enrollment; 6) any contraindication to ECP, i.e. contraindication to heparin or 8-MOP; 7) post-transplant exposure to any novel immunosuppressive medication (e.g., alemtuzumab) within 100 days prior to enrollment; 8) donor lymphocyte infusion within 100 days prior to enrollment; 9) active malignant relapse; 10) active uncontrolled infection; 11) inability to comply with IL-2 treatment regimen; 12) uncontrolled cardiac angina or symptomatic congestive heart failure (NYHA Class III or IV; Table 9); 13) organ transplant (allograft) recipient; 14) HIV-positive individuals on combination antiretroviral therapy are ineligible because of the potential for pharmacokinetic interactions with the agents used after allogeneic HSCT. In addition, these individuals are at increased risk of lethal infections. Appropriate studies are undertaken in participants receiving combination antiretroviral therapy when indicated; 15) individuals with active hepatitis B or C are ineligible as they are at high risk of lethal treatment-related hepatotoxicity after HSCT; 16) other investigational drugs within 4 weeks prior to enrollment, unless cleared by the principal investigator; and 17) pregnant women are excluded because of the potential for teratogenic or abortifacient effects. Because there is an unknown but potential risk of adverse events in nursing infants secondary to treatment of the mother, breastfeeding should be discontinued.

Subjects are treated according to the following treatment regimen:

Each study participant receives standard-of-care twice-weekly ECP for 16 weeks as per the transfusion medicine SOP. Briefly, ECP is performed with the Therakos UVAR XTS system. The blood volume processed and 8-MOP dosing is determined by subject hematocrit and blood volume per manufacturer guidelines. A 5004. buffy coat aliquot from the ECP recirculation bag can also be collected before photoactivation and characterized for absolute numbers of WBC subsets. A detailed assessment of the immunologic impact of ECP and ECP plus IL-2 can be performed on peripheral blood Treg, Tcon, CD8, B, NK and DC cell subsets, including apoptotic populations. Cytokines are measured after each ECP cycle. Associations of response with immunologic variables over time are also determined including analysis of prednisone use, overall survival, progression-free survival, non-relapse mortality, and relapse. Apheresis physicians can evaluate for ECP-related toxicities, including hemorrhage, cytopenias, and procedure intolerance (i.e., constitutional symptoms or cardiovascular instability). Treatment toxicity in participants who receive any ECP or ECP plus IL-2 are also monitored. Predictors for response are also determined, such as using univariable analysie, including the impact of number of prior cGVHD therapies.

Clinical responders continue ECP as standard-of-care after week 16, with or without extended-duration IL-2 therapy. If participants on ECP experience worsening of cGVHD requiring additional therapy prior to week 8, they may initiate low-dose IL-2 early, in consultation with the study PI. After week 8, participants initiate daily low-dose SC IL-2 ($1 \times 10^6$ IU/m$^2$/day) for self-administration for the remaining 8 weeks of ECP, i.e., from end of week 8-16. IL-2 is typically administered on an outpatient basis. Expected toxicities and potential risks as well as dose modifications are described in Example 2. Prednisone (or equivalent steroid) is continued concomitantly with IL-2 without dose modification. Taper of prednisone is permitted at the discretion of the treating physician if deemed in the participant's interest (e.g., steroid toxicity). Of note, clinically stable cGVHD during taper of other immune suppression medications is considered evidence of IL-2 efficacy and progression of cGVHD during taper of other immunosuppressive therapy is not considered evidence of IL-2 toxicity or lack of efficacy.

In other embodiments, a one stage single arm trial of twice-weekly ECP for 12 weeks and 6 weeks of IL-2 at $1 \times 10^6$ IU/m$^2$/day during weeks 6-12 is administered to cGVHD subjects, such as those with an inadequate response to at least 4 weeks of prednisone or its equivalent at a dose of 0.25/mg/kg/day; total leukocyte count≥1000/mm$^3$, platelets≥25,000/mm$^3$; and no prior ECP or IL-2 therapy.

Extended-duration therapy: After completing the 16 week study, patients experiencing clinical benefit (complete or partial response; as well as minor response not meeting NIH criteria for partial response) with an acceptable toxicity profile are permitted to continue extended-duration IL-2 treatment indefinitely at the discretion of the treating physician. Restarting on extended-duration treatment can be delayed for only up to 2 weeks for justifiable clinical or administrative reasons. Longer delays in restarting treatment must be approved by the principal investigator. While on extended-duration IL-2, patients are reassessed every 4 weeks to determine if IL-2 therapy should continue, at the discretion of the treating physician, who documents the rationale for the continued IL-2 therapy.

Toxicity data for extended-duration IL-2 is collected on an ongoing basis and all treatment-related SAEs are reported to the principal investigator and the IRB. Taper of other immune suppression medications during extended-duration IL-2 is at the discretion of the treating physician. In the event of toxicity attributable to IL-2, dose modifications as described herein are permitted at the discretion of the treating physician.

The required assessments for patients on extended-duration IL-2 therapy include: 1) clinic visits locally or at study center for evaluation of toxicity and clinical benefit of IL-2 every 4 weeks (±2 weeks). Required laboratory tests are CBC with differential and serum chemistries-glucose, BUN, creatinine, total bilirubin, alkaline phosphatase, AST, ALT, calcium. 2) clinic visits at study center every 8 weeks (±4 weeks). Required laboratory tests (in addition to above) include immune assays that include quantitative serum immune globulins, plasma banking, and storage of additional mononuclear cells.

The following evaluations are performed within two weeks prior to ECP for all participants: 1) medical history and documentation of the rationale for treatment of the patient's disease (including steroid dose); 2) physical examination, including vital signs, weight, performance status; 3) cGVHD assessment; 4) pregnancy test for women of child-bearing potential; 5) hematology: complete blood count (CBC) with differential; 6) serum chemistries: glucose, BUN, creatinine, uric acid, total bilirubin, alkaline phosphatase, LDH, total protein, albumin, AST, ALT, and calcium; 7) thyroid function tests (TSH, T4, free T4); 8) CMV viral load; 9) quantitative serum immune globulins; and 10) immunology: plasma banking and storage of additional mononuclear cells.

The following evaluations are required (except where indicated) within two weeks prior to ECP for patients with cGVHD involving specific organ systems: 1) ocular examination with a Schirmer's test, for patients with ocular cGVHD (optional); 2) dermatologic assessment (±biopsy), for patients with cutaneous cGVHD; 3) oral examination (±biopsy), for patients with oral cGVHD (optional); 4) pulmonary function tests, for patients with pulmonary manifestations of cGVHD (within 4 weeks prior to treatment to 1 week after); and 5) flexion assessment of affected joints, for individuals with contractures or musculoskeletal involvement related to cGVHD.

The following are evaluations during ECP and IL-2 treatment (end of weeks 1, 2, 4, 6, 8, 9, 10, 12, 14), and off-study (end of week 16): 1) medical history and clinical examination (including steroid dose, weeks 8 & 16); 2) drug diary review with member of study team (starting with IL-2 treatment); 3) toxicity assessment will be done on the same day as history and clinical examination; 4) hematology: CBC with differential; 5) serum chemistries: glucose, BUN, creatinine, uric acid, total bilirubin, alkaline phosphatase, LDH, total protein, albumin, AST, ALT, and calcium; 6) CMV Viral load (or per institutional practice); 7) quantitative serum immune globulins (weeks 4, 8, 12, 16); 8) immunology: plasma banking and storage of additional mononuclear cells (weeks 1, 2, 4, 6, 8, 9, 10, 12, 14, 16); and 9) thyroid function tests (TSH, T4, free-T4) (week 16).

The following are assessments required (except where indicated) at end of week 8 and 16 of study (in addition to cGVHD symptom score) for patients with cGVHD involving specific organs: 1) cGVHD assessment; 2) ocular examination with a Schirmer's test, for patients with ocular cGVHD (optional); 3) dermatologic assessment (±biopsy), for patients with cutaneous cGVHD; 4) oral examination (±biopsy), for patients with oral cGVHD (optional); 5) pulmonary function tests, for patients with pulmonary manifestations of cGVHD; and 6) flexion assessment of affected joints, for individuals with contractures or musculoskeletal involvement related to cGVHD.

The following table is a summary of data for recordation:

TABLE 19

|  | Within 2 Wks prior (baseline) | During Therapy (End of Wks 1, 2, 4, 6, 8, 9, 10, 12, 14)[a] | End of Wk 16[a] | Extended duration IL-2 (4 Wkly)[c] |
| --- | --- | --- | --- | --- |
| Medical History | X | X | X | X |
| Physical Exam | X | X | X | X |
| Toxicity Assessment |  | X | X | X |
| cGVHD Symptom Score | X | X[b] | X | X[#] |
| Pregnancy Test[¶] | X |  |  |  |
| Pulmonary Function | ○ | ○[b] | ○ | ○[#] |
| Dermatologic Assessment | ○ | ○[b] | ○ | ○[#] |
| Oral Assessment | ○ | ○[b] | ○ | ○[#] |
| Flexion Assessment | ○ | ○[b] | ○ | ○[#] |
| Ocular Assessment | ○ | ○[b] | ○ | ○[#] |

TABLE 19-continued

|  | Within 2 Wks prior (baseline) | During Therapy (End of Wks 1, 2, 4, 6, 8, 9, 10, 12, 14)[a] | End of Wk 16[a] | Extended duration IL-2 (4 Wkly)[c] |
| --- | --- | --- | --- | --- |
| CDC with Diff | X | X* | X | X |
| Serum Chemistry | X | X* | X | X |
| Quantitative Immune Globulins | X | X[d] | X | X[б] |
| Immunology[1] | X | X | X | X[б] |
| Steroid Assessment[2] | X | X[b] | X | X[б] |
| CMV Viral Load | X | X | X | X |
| Thyroid Function | X |  | X | X[б] |
| Drug Diary[+] |  | X | X | X |

X—Required Evaluation
○—Required for patients with clinical involvement of these organ systems (oral and ocular assessments are optional). Baseline pulmonary function tests can be scheduled up to 4 weeks prior to start of treatment to 1 week after for scheduling flexibility.
[1]Immunology: plasma banking; storage of additional mononuclear cells.
[2]Systemic steroids should not be tapered unless there is toxicity, e.g. severe hyperglycemia (with permission of study PI).
[a]Testing at end of weeks 1, 2, 4, 6, 8, 9, 10, 12, 14 will be performed ±4 days, to allow for scheduling and administrative flexibility around weekends, holidays etc.
[b]Week 8 for steroid dose and cGVHD assessments,
[c]Testing during extended-duration therapy will be performed ±2 weeks, to allow for scheduling and administrative flexibility around patient travel, work, holidays etc.
[d]Week 4, 8, 12.
*Laboratory testing of CBC/manual diff, serum creatinine and LDH will also be performed 4 ± 2 days after IL-2 initiation, to assess for anemia, thrombocytopenia, schistocytes and/or renal dysfunction associated with thrombotic microangiopathy.
[б]Every 8 weeks (±4 weeks) at time of mandatory study-center follow-up.
[#]Every 16 weeks (+/−4 weeks) during year 1 at time of mandatory study-center follow-up.
[¶]For women of child-bearing potential.
[+]To be completed and returned to clinic at least every 2 weeks during study IL-2 treatment. To be completed at and returned to clinic at least every 8 weeks for extended-duration IL-2.

Both toxicity and responses are assessed. Participants who receive at least one dose of IL-2 are evaluable for toxicity of IL-2 treatment. Participants who receive at least 4 weeks of IL-2 and have had their disease re-assessed are considered evaluable for combination IL-2 plus ECP response. These participants have their response classified according to the definitions provided herein and stated below. For example and in addition to definitions in Example 2, Chronic GVHD Symptom Score refers to participants self-reports symptoms and signs of cGVHD using the validated chronic GVHD Symptom Scale. Self-Reported symptom Scales are obtained at baseline and weeks 8 and 16. Steroid Use for Chronic GVHD refers to participants having their total daily dose of corticosteroids recorded at baseline, and at 8 and 16 weeks. In the case of alternate daily dosing of corticosteroids, the average daily dose will be recorded for study purposes. Immune Assessment refers to participants undergoing testing for immunologic function, performed at baseline, and at weeks 1, 2, 4, 6, 8, 9, 10, 12, 14 and 16. Testing includes plasma banking, and storage of additional mononuclear cells. Quantiative immune globulins are tested at baseline and weeks 4, 8, 12, and 16.

For a one-stage Phase II trial to assess the efficacy of 12 weeks extracorporeal photopheresis (ECP) with the addition of daily low-dose subcutaneous (SC) interleukin-2 (IL-2) for weeks 6-12 in patients with steroid-refractory chronic graft-versus-host disease (cGVHD), the primary endpoint is overall response as evaluated at 12 weeks of treatment. Based on a randomized phase 2 trial of ECP vs. placebo (40% response rate of skin cGVHD and 33% response rate of non-skin cGVHD) (Flowers et al. (2008) *Blood* 112:2667-2674), IL-2 plus ECP is efficacious if the overall response rate is >60% and unworthy if <40%. With this design the probability of concluding the treatment efficacious is 0.84 if the true but unknown response rate is 60% and 0.09 if the true rate is 40%. In a previous phase 1 IL-2 study in the same patient population the median baseline Treg count was 16.8 cells/μL. Assuming a similar baseline Treg count, in 34 patients there will be >99% power to detect a Treg count increase to 33.6 cells/μL at week 6 of ECP if the effect size (i.e., mean difference divided by its standard deviation) is 1 and 90% power if the effect size is 0.6. A synergistic effect on Treg count with ECP plus IL-2 is also believed. Of 34 patients, if 30 complete week 12 treatment and Treg rises from 33.6 at week 6 to 200 at week 12, there will be >99% power to detect this difference if the effect size is 1 and 87% power if the effect size is 0.6. Longitudinal data analysis evaluates Treg increase over time and determines whether this is associated with ECP alone or ECP plus IL-2. Associations between immunologic and clinical response are also performed.

Gender of subjects is not used as a criterion for inclusion or exclusion in this study and there are no restrictions on the accrual of minorities. In 2013, 41% of all transplanted patients were women and approximately 10% of patients were minorities. Based on this self-reported ethnicity and gender in our transplant program in 2013, the anticipated accrual in subgroups defined by gender and race is summarized in Table 20 below.

TABLE 20

Accrual Targets

| Ethnic Category | Sex/Gender | | | | | |
|---|---|---|---|---|---|---|
| | Females | | Males | | Total | |
| Hispanic or Latino | 1 | + | 1 | = | 2 | |
| Not Hispanic or Latino | 9 | + | 14 | = | 23 | |
| Ethnic Category: Total of all subjects | 10 (A1) | + | 15 (B1) | = | 25 (C1) | |
| Racial Category | | | | | | |
| American Indian or Alaskan Native | 0 | + | 0 | = | 0 | |
| Asian | 1 | + | 1 | = | 2 | |

TABLE 20-continued

Accrual Targets

| Ethnic Category | Sex/Gender | | | | | |
|---|---|---|---|---|---|---|
| | Females | | Males | | Total | |
| Black or African American | 1 | + | 1 | = | 2 | |
| Native Hawaiian or other Pacific Islander | 0 | + | 0 | = | | |
| White | 8 | + | 13 | = | 21 | |
| Racial Category: Total of all subjects | 10 (A2) | + | 15 (B2) | = | 25 (C2) | |

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the World Wide Web and/or the National Center for Biotechnology Information (NCBI) on the World Wide Web.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of treating a subject afflicted with graft-versus-host disease (GVHD) comprising:
   a) administering to the subject an induction regimen comprising administering to the subject interleukin-2 (IL-2) at a dose that increases the subject's plasma IL-2 level and increases the subject's ratio of regulatory T lymphocytes (Tregs) to conventional T lymphocytes (Tcons) (Tregs:Tcons), wherein the induction regimen dose is less than about $6.0 \times 10^6$ IU/m$^2$/day; and
   b) subsequently administering to the subject a maintenance regimen comprising administering to the subject an IL-2 maintenance dose that is higher than the induction regimen dose and that i) further increases the subject's plasma IL-2 level and ii) further increases the ratio of Tregs to Tcons, thereby treating the subject.

2. The method of claim 1, wherein the IL-2 maintenance regimen increases the subject's plasma IL-2 level beyond the peak plasma IL-2 level induced by the induction regimen.

3. The method of claim 1, wherein the induction regimen dose is about $0.3 \times 10^6$ IU/m$^2$/day to about $3.0 \times 10^6$ IU/m$^2$/day.

4. The method of claim 1, wherein the administration of the induction regimen comprises administration once per day.

5. The method of claim 1, wherein the Tregs:Tcons in the maintenance regimen is increased by and maintained at a level at least 20% over the maximal Tregs:Tcons during the induction regimen.

6. The method of claim 1, wherein the maintenance regimen dose is
   i) at least about 20% higher than the induction regimen dose;
   ii) about $0.3 \times 10^6$ IU/m$^2$/day to about $3.0 \times 10^6$ IU/m$^2$/day; and/or
   iii) less than about $6.0 \times 10^6$ IU/m$^2$/day.

7. The method of claim 1, wherein the administration of the maintenance regimen comprises administration once per day for 1 day, 2 consecutive days, 3 consecutive days, 4 consecutive days, 5 consecutive days, 6 consecutive days, 7 consecutive days, 8 consecutive days, 9 consecutive days, 10 consecutive days, 11 consecutive days, 12 consecutive days, 13 consecutive days, or at least 14 consecutive days.

8. The method of claim 1, wherein the IL-2
   i) is administered in a pharmaceutically acceptable formulation; and/or
   ii) is administered by an administration route selected from the group consisting of subcutaneous, intravenous, intraperitoneal, and intramuscular.

9. The method of claim 1, wherein the IL-2 is administered subcutaneously.

10. The method of claim 1, wherein the subject
    i) has had an inadequate response to systemic steroids;
    ii) has persistent or recurrent chronic GVHD despite at least 2 prior systemic therapies including steroids; and/or
    iii) has had extra-corporeal photopheresis (ECP) prior to IL-2 administration.

11. The method of claim 1, wherein the subject is a mammal, an animal model of an immune disorder or a human.

12. The method of claim 1, wherein the subject is a pediatric subject or wherein GVHD is chronic GVHD.

13. The method of claim 1, wherein the induction regimen and/or the maintenance regimen further comprises administration of one or more additional therapies to treat the immune disorder.

14. The method of claim 13, wherein the one or more additional therapies is administration of Tregs and the Tregs are administered
    i) with T cells other than Tregs; and/or
    ii) at between about $0.1 \times 10^6$ cells/kg body weight to $1.0 \times 10^6$ cells/kg body weight.

15. The method of claim 14, wherein the one or more additional therapies
  i) has a Tregs:Tcons ratio of at least 1:2;
  ii) is obtained from T cells that are CD8−, CD9−, and CD25+; and/or
  iii) has >70% total cell viability, a negative gram stain, ≥90% CD4+CD25+ cells, and/or ≥50% FoxP3+ cells.

16. The method of claim 13, wherein the one or more additional therapies is administration of Tregs, and
  i) the subject's own Tregs are administered to the subject; and/or
  ii) Tregs from the same hematopoietic stem cell donor from which hematopoietic stem cell transplantation was obtained are used.

17. The method of claim 13, wherein the one or more additional therapies is administration of Tregs and the Tregs are administered
  i) as an infusion; and/or
  ii) before, concurrently with, or after IL-2 administration.

18. The method of claim 13, wherein the one or more additional therapies is extra-corporeal photopheresis (ECP).

* * * * *